US012503424B2

(12) United States Patent
Stoessel et al.

(10) Patent No.: US 12,503,424 B2
(45) Date of Patent: Dec. 23, 2025

(54) MATERIALS FOR ELECTRONIC DEVICES

(71) Applicant: Merck Patent GmbH, Darmstadt (DE)

(72) Inventors: Philipp Stoessel, Frankfurt am Main (DE); Dominik Joosten, Frankfurt am Main (DE); Teresa Mujica-Fernaud, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 883 days.

(21) Appl. No.: 16/482,502

(22) PCT Filed: Jan. 30, 2018

(86) PCT No.: PCT/EP2018/052196

§ 371 (c)(1),
(2) Date: Jul. 31, 2019

(87) PCT Pub. No.: WO2018/141706

PCT Pub. Date: Aug. 9, 2018

(65) Prior Publication Data

US 2020/0013960 A1 Jan. 9, 2020

(30) Foreign Application Priority Data

Feb. 2, 2017 (EP) .................................... 17154481

(51) Int. Cl.

| | |
|---|---|
| ***C07C 211/61*** | (2006.01) |
| ***C07D 307/91*** | (2006.01) |
| ***C07D 405/04*** | (2006.01) |
| ***C07D 405/12*** | (2006.01) |
| ***C07D 407/12*** | (2006.01) |
| ***C07F 5/02*** | (2006.01) |
| ***H10K 50/15*** | (2023.01) |
| ***H10K 50/155*** | (2023.01) |
| ***H10K 50/165*** | (2023.01) |
| ***H10K 85/60*** | (2023.01) |
| *H10K 50/18* | (2023.01) |

(52) U.S. Cl.

CPC .......... *C07C 211/61* (2013.01); *C07D 307/91* (2013.01); *C07D 405/04* (2013.01); *C07D 405/12* (2013.01); *C07D 407/12* (2013.01); *C07F 5/025* (2013.01); *H10K 85/624* (2023.02); *H10K 85/633* (2023.02); *H10K 85/654* (2023.02); *H10K 85/6574* (2023.02); *H10K 50/155* (2023.02); *H10K 50/156* (2023.02); *H10K 50/165* (2023.02); *H10K 50/18* (2023.02)

(58) Field of Classification Search

CPC ............... C07C 211/61; C07C 2603/18; C07C 2603/56; C07D 307/91; C07D 405/04; C07D 405/12; C07D 407/12; C07D 471/04; C07F 5/025; C09K 11/025; C09K 11/06; H01L 51/0056; H01L 51/006; H01L 51/0067; H01L 51/0071; H01L 51/0072; H01L 51/0073; H01L 51/0074; H01L 51/5016; H01L 51/5056; H01L 51/506; H01L 51/5064; H01L 51/5072; H01L 51/5076; H01L 51/5096; Y02E 10/549; H10K 85/624; H10K 85/633; H10K 85/654; H10K 85/657; H10K 85/6572; H10K 85/6574; H10K 85/6576; H10K 50/11; H10K 50/15; H10K 50/155; H10K 50/156; H10K 50/16; H10K 50/165; H10K 50/18

See application file for complete search history.

(56) References Cited

U.S. PATENT DOCUMENTS

| | | | |
|---|---|---|---|
| 6,416,887 B1 | 7/2002 | Tokito et al. | |
| 8,932,732 B2 | 1/2015 | Buesing et al. | |
| 10,158,083 B2 | 12/2018 | Stoessel et al. | |
| 2006/0063031 A1 * | 3/2006 | Brown | ................ H01L 51/5016 313/506 |
| 2016/0254457 A1 | 9/2016 | Ma et al. | |

FOREIGN PATENT DOCUMENTS

| | | |
|---|---|---|
| DE | 102006025846 A1 | 12/2007 |
| WO | 00/27946 A1 | 5/2000 |
| WO | 02/43449 A1 | 5/2002 |
| WO | WO-2015086108 A1 | 6/2015 |
| WO | WO-2016150544 A1 | 9/2016 |

OTHER PUBLICATIONS

Debroy, P., et al., "Hexabenzo[4.4.4]propellane: A Helical Molecular Platform for the Construction of Electroactive Materials", Organic Letters, vol. 9, No. 21, (2007), pp. 4091-4094.
International Search Report for PCT/EP2018/052196 mailed May 7, 2018.
Kimura, M., et al., "Utilization of an Aromatic [4.4.4]Propellane as Thermally Stable Hole- Transport Materials in OLEDs", Bulletin of the Chemical Society of Japan, vol. 79, No. 11, (2006), pp. 1793-1797.
Kubo, T., et al., "A facile synthesis of trinaphtho[3.3.3]propellane and its Tr-extension and the formation of a two-dimensional honeycomb molecular assembly", Chemical Communications, vol. 51, No. 18, (2015), pp. 3801-3803.
Written Opinion of the International Searching Authority for PCT/EP2018/052196 mailed May 7, 2018.
Zhigang Li and Hong Meng; Organic Light-Emitting Materials and Devices; Taylor & Francis Group; 2007; pp. 312-320; Boca Raton, Florida.

* cited by examiner

*Primary Examiner* — Elizabeth M. Dahlburg
(74) *Attorney, Agent, or Firm* — Faegre Drinker Biddle & Reath LLP

(57) ABSTRACT

The invention relates to propellane compounds according to defined formula, to the use of said compounds in electronic devices, and to electronic devices containing one or more of the known propellane compounds. The invention also relates to methods for producing the known propellane compounds.

18 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2018/052196, filed Jan. 30, 2018, which claims benefit of European Application No. 17154481.0, filed Feb. 2, 2017, both of which are incorporated herein by reference in their entirety.

The present application relates to propellane compounds of the formulae defined further down that are suitable for use in electronic devices. The present application further relates to processes for preparing the compounds mentioned, and to electronic devices comprising the compounds mentioned.

Electronic devices in the context of this application are understood to mean what are called organic electronic devices, which contain organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in improving the performance data, especially lifetime, efficiency and operating voltage. In these aspects, it has not yet been possible to find any entirely satisfactory solution.

A great influence on the performance data of electronic devices is possessed by emission layers, layers having hole-transporting function, and layers having electron-transporting function. For use in these layers, there is still a search for new materials, especially materials having hole-transporting and electron-transporting properties.

In the prior art, triarylamine compounds in particular are known as hole-transporting materials for electronic devices. There are known triarylamine compounds having a multitude of different types of aryl groups as substituents on the nitrogen atom of the triarylamine, for example phenanthrenyl groups, spirobifluorenyl groups and fluorenyl groups. However, there is still a need for alternative triarylamine compounds having novel embodiments of aryl groups on the nitrogen atom of the triarylamine that are suitable for use in electronic devices. There is also a need for improvement with regard to the performance data in use of the compounds mentioned in electronic devices, especially with regard to lifetime and efficiency.

Known electron-transporting materials that are likewise disclosed in the prior art include a multitude of substance classes, for example triazine derivatives, pyrimidine derivatives and quinoline derivatives. Here too, there is a need for alternative base skeletons and substance classes. There is also a need for improvement with regard to the performance data in use of the compounds mentioned in electronic devices, especially with regard to lifetime and efficiency.

It has now been found that particular propellane compounds of the formulae (I) to (IV) defined in detail below are of excellent suitability for use in electronic devices, especially for use in OLEDs, once again especially for use therein as hole-transporting or electron-transporting materials. They preferably result in excellent lifetime and efficiency of the device when used in OLEDs.

The invention provides a compound of a formula (I), (II), (III) or (IV)

Formula (I)

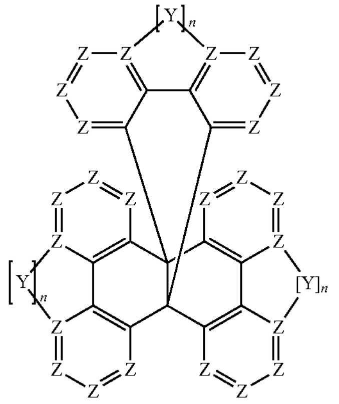

Formula (II)

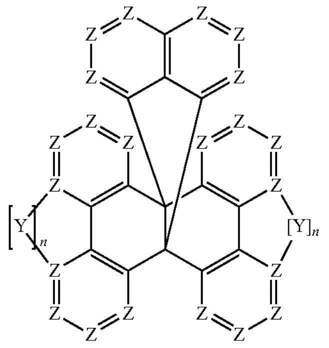

Formula (III)

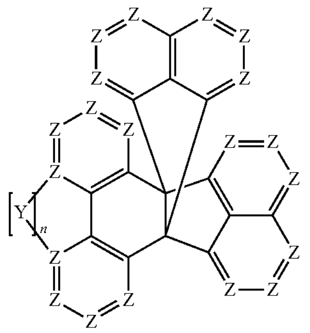

Formula (IV)

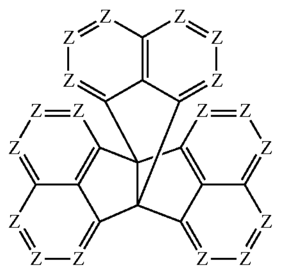

where the variables that occur are as follows:

Z is the same or different at each instance and is selected from N and $CR^1$ or C, where a Z group is C in the specific case when a Y group is bonded to it;

Y is the same or different at each instance and is selected from $BR^2$, $C(R^2)_2$, $Si(R^2)_2$, $NR^2$, $P(O)R^2$, O, S, SO, $SO_2$;

n is the same or different at each instance and is 0 or 1;

$R^1$, $R^2$ are the same or different at each instance and are selected from H, D, F, CN, $Si(R^3)_3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, and aromatic ring systems having 6 to 40 aromatic ring atoms; where two or more $R^1$ and/or $R^2$ radicals may be joined to one another and may form a ring; where the alkyl, alkoxy, alkenyl and alkynyl groups mentioned and the aromatic ring systems mentioned may each be substituted by one or more $R^3$ radicals; where an indole ring may be fused in each case to one or more of the six-membered rings in formula (I) to (IV) and may in turn be substituted by $R^3$ radicals;

$R^3$ is the same or different at each instance and is selected from H, D, F, CN, $Si(R^4)_3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, and aromatic ring systems having 6 to 40 aromatic ring atoms; where two or more $R^3$ radicals may be joined to one another and may form a ring; where the alkyl, alkoxy, alkenyl and alkynyl groups mentioned and the aromatic ring systems mentioned may each be substituted by one or more $R^4$ radicals;

$R^4$ is the same or different at each instance and is selected from H, D, F, CN, alkyl or alkoxy groups having 1 to 20 carbon atoms, alkenyl or alkynyl groups having 2 to 20 carbon atoms, and aromatic ring systems having 6 to 40 aromatic ring atoms; where two or more $R^4$ radicals may be joined to one another and may form a ring; and where the alkyl, alkoxy, alkenyl and alkynyl groups and the aromatic ring systems mentioned may be substituted by F or CN;

characterized in that at least one Z group per formula selected from the formulae (I), (II), (III) and (IV) is $CR^1$;

and further characterized in that exactly one $R^1$ group per formula is replaced by a group of the formula (A) or a group of the formula (H)

Formula (A)

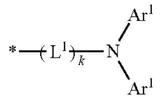

Formula (H)

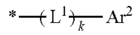

and further characterized in that exactly one $R^1$ group per formula selected from the formulae (II), (III) and (IV) is replaced by a group of the formula (A)

where:

$L^1$ is the same or different at each instance and is an aromatic ring system having 6 to 24 aromatic ring atoms or a heteroaromatic ring system having 5 to 24 aromatic ring atoms, each of which may be substituted by one or more $R^5$ radicals;

k is 0, 1, 2 or 3;

$Ar^1$ is the same or different at each instance and is an aromatic ring system having 6 to 24 aromatic ring atoms or a heteroaromatic ring system having 5 to 24 aromatic ring atoms, which may be substituted by one or more $R^5$ radicals;

$Ar^2$ is a heteroaromatic ring system which has 5 to 24 aromatic ring atoms and may be substituted by one or more $R^5$ radicals;

$R^5$ is the same or different at each instance and is selected from H, D, F, $C(=O)R^6$, CN, $Si(R^6)_3$, $N(R^6)_2$, $P(=O)(R^6)_2$, $OR^6$, $S(=O)R^6$, $S(=O)_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by $-R^6C=CR^6-$, $-C\equiv C-$, $Si(R^6)_2$, C=O, $C=NR^6$, $-C(=O)O-$, $-C(=O)NR^6-$, $NR^6$, $P(=O)(R^6)$, —O—, —S—, SO or $SO_2$;

$R^6$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^6$ radicals may be joined to one another and may form a ring; and where the alkyl, alkoxy, alkenyl and alkynyl groups, aromatic ring systems and heteroaromatic ring systems mentioned may be substituted by F or CN;

where the group of the formula (A) or the group of the formula (H) is bonded via the bond marked *.

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood here to mean that the cycles share at least one edge with one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 40 carbon atoms in the ring system and does not include any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a non-aromatic unit, for example one or more optionally substituted C, Si, N, O or S atoms. In this case, the non-aromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also regarded as aromatic ring systems in the context of this invention, for example systems such as biphenyl and terphenyl.

Preferably, an aromatic ring system is understood to mean a chemical group in which the aryl groups present therein are conjugated to one another. This means that the aryl groups present must be bonded to one another via single bonds or via connecting units having a free pi electron pair that can take part in the conjugation. Connecting units here are preferably selected from nitrogen atoms, individual C═C units, individual C≡C units, multiple C═C units conjugated to one another and/or C≡C units, —O—, and —S—.

A heteroaromatic ring system in the context of this invention contains 5 to 40 aromatic ring atoms, at least one of which is a heteroatom. The heteroatoms of the heteroaromatic ring system are preferably selected from N, O and/or S. A heteroaromatic ring system corresponds to the definition stated above for an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording should also be understood to mean that, if one of the two radicals is hydrogen, the second radical binds to the position to which the hydrogen atom was bonded, forming a ring.

Among the formulae (I) to (IV), preference is given to formula (I).

Preferably not more than three Z groups per aromatic ring are N, and the rest of the Z groups in the aromatic ring are $CR^1$ or C.

Preferably, Z is $CR^1$ or C, where Z is C in the specific case when a Y group is bonded to it.

Preferably, Y is the same or different at each instance and is selected from $NR^2$, O, S and $C(R^2)_2$. More preferably, Y is the same or different at each instance and is selected from O and $NR^2$. Most preferably, Y is O.

Preferably, the sum total of the indices n in a compound of the formula (I) or (II) is 1 or 0, more preferably 0. Preferably, the sum total of the indices n in a compound of the formula (III) is 0.

Preferably, n at each instance is 0.

If multiple different positions of the Y group are possible, the Y group is preferably bonded to that six-membered ring which bears a group of the formula (A) or (H).

$R^1$ is the same or different at each instance and is selected from H, D, F, CN, straight-chain alkyl groups having 1 to 12 carbon atoms, branched or cyclic alkyl groups having 3 to 12 carbon atoms, and aromatic ring systems having 6 to 24 aromatic ring atoms; where two or more $R^1$ radicals may be joined to one another and may form a ring; and where the alkyl groups mentioned and the aromatic ring systems mentioned may each be substituted by one or more $R^3$ radicals; where an indole ring may be fused in each case to one of the six-membered rings in formula (I) to (IV) and may in turn be substituted by $R^3$ radicals.

Preferred examples of compounds of the formula (I) having an indole ring fused onto formula (I) conform to one of the formulae (I-In-1) and (I-In-2) shown below Formula (I-In-1)

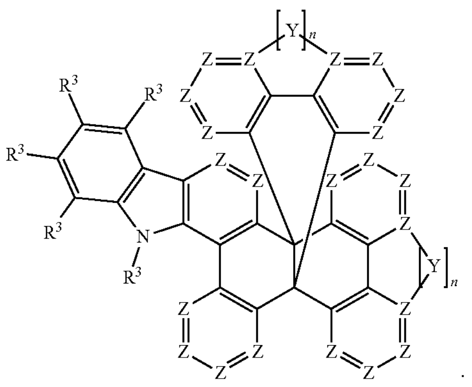

Formula (I-In-2)

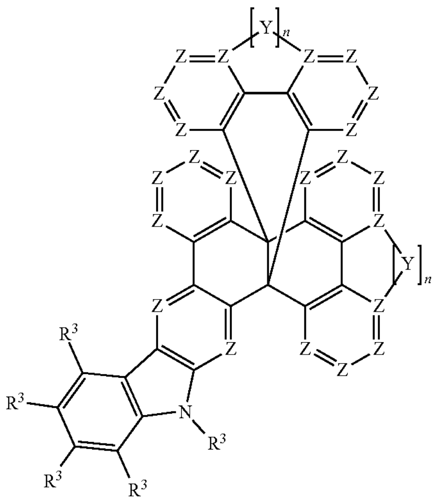

where the groups and indices that occur are as defined for formula (I), and the preferences specified in the present application are otherwise applicable.

More preferably, $R^1$ is the same or different at each instance and is selected from H, D, straight-chain or branched alkyl groups having up to 12 carbon atoms, and aromatic ring systems having 6 to 24 aromatic ring atoms, where the alkyl groups mentioned and the aromatic ring systems mentioned may each be substituted by one or more $R^3$ radicals. Most preferably, $R^1$ is H.

$R^2$ is the same or different at each instance and is selected from F, straight-chain alkyl groups having 1 to 12 carbon atoms, branched or cyclic alkyl groups having 3 to 12 carbon atoms, and aromatic ring systems having 6 to 24 aromatic ring atoms; where two $R^2$ radicals may be joined to one another and may form a ring; and where the alkyl groups mentioned and the aromatic ring systems mentioned may each be substituted by one or more $R^3$ radicals. More preferably, $R^2$ is selected from straight-chain or branched alkyl groups having up to 12 carbon atoms, and aromatic ring systems having 6 to 24 aromatic ring atoms, where two $R^2$ radicals that bind to the same carbon atom in a $C(R^2)_2$ group and are alkyl groups or aryl groups may be joined to one another to give a cyclic alkyl group or to give a fluorene group. Preference is given to cyclic alkyl groups having 5 to 6 carbon atoms.

Preferably, $R^3$ is the same or different at each instance and is selected from H, D, F, CN, straight-chain alkyl groups having 1 to 12 carbon atoms, branched or cyclic alkyl groups having 3 to 12 carbon atoms, and aromatic ring systems having 6 to 24 aromatic ring atoms; where two or more $R^3$ radicals may be joined to one another and may form a ring; and where the alkyl groups mentioned and the aromatic ring systems mentioned may each be substituted by one or more $R^4$ radicals.

Preferably, $R^4$ is the same or different at each instance and is selected from H, D, F, CN, straight-chain alkyl groups having 1 to 12 carbon atoms, branched or cyclic alkyl groups having 3 to 12 carbon atoms, and aromatic ring systems having 6 to 24 aromatic ring atoms; where two or more $R^4$ radicals may be joined to one another and may form a ring; and where the alkyl groups mentioned and the aromatic ring systems mentioned may each be substituted by F or CN.

Preferably, exactly one $R^1$ group per formula (I) is replaced by a group of the formula (A).

In formula (I), the group of the formula (H) or (A) is preferably bonded in one of the positions identified by 1, 2 and 4 below, more preferably in one of the positions identified by 3 and 4 below, most preferably in the position identified by 4 below.

Formula (I)

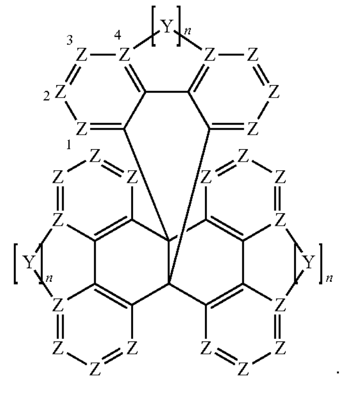

In formulae (I), (II) and (IV), the group of the formula (A) is preferably bonded in the position identified by "3" below.

Formula (II)

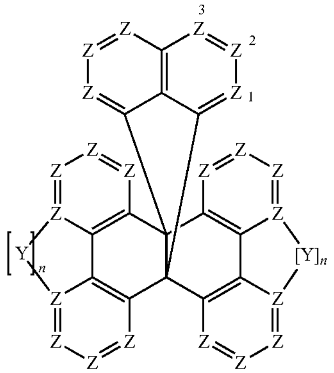

Formula (III)

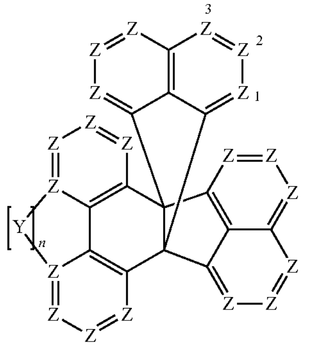

Formula (IV)

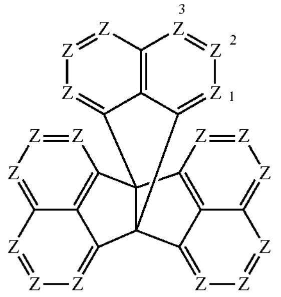

In groups of the formula (A), k is preferably 0 or 1, more preferably 0. $L^1$ is preferably an aromatic ring system which has 6 to 24 aromatic ring atoms and may be substituted by one or more $R^5$ radicals. More preferably, $L^1$ is a divalent group selected from phenylene, biphenylene, terphenylene, naphthylene, dibenzofuran, dibenzothiophene, carbazole and fluorene, where the divalent group may be substituted by one or more $R^5$ radicals. $Ar^1$ is preferably the same or different at each instance and is selected from phenyl, biphenyl, terphenyl, fluorenyl, naphthyl, spirobifluorenyl, pyridyl, pyrimidyl, triazinyl, dibenzofuranyl, benzofused dibenzofuranyl, dibenzothiophenyl, benzofused dibenzothiophenyl, carbazolyl, and benzofused carbazolyl, and combinations of two, three or four of these groups, where the groups mentioned may each be substituted by one or more $R^5$ radicals.

In groups of the formula (H), k is preferably 0 or 1. $L^1$ is preferably an aromatic ring system which has 6 to 24 aromatic ring atoms and may be substituted by one or more $R^5$ radicals. More preferably, $L^1$ is a divalent group selected from phenylene, biphenylene, terphenylene, naphthylene, dibenzofuran, dibenzothiophene, carbazole and fluorene, where the divalent group may be substituted by one or more $R^5$ radicals. $Ar^2$ is preferably a heteroaryl group which has 6 to 24 aromatic ring atoms and may be substituted by one or more $R^5$ radicals.

More preferably, $Ar^2$ is the same or different at each instance and is selected from groups of the following formulae:

(Ar$^2$-A)

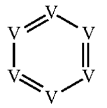

(Ar$^2$-B)

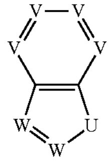

(Ar$^2$-C)

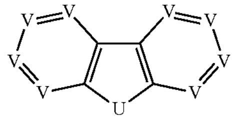

(Ar$^2$-D)

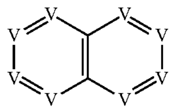

where the variables that occur are defined as follows:

V is the same or different at each instance and is N or $CR^5$, where at least one V group in each of formulae ($Ar^2$-A) and ($Ar^2$-D) is N;

W is the same or different at each instance and is N or $CR^5$;

U is $NR^5$;

where one $R^5$ group per formula is replaced by the bond to the $L^1$ group or the propellane group.

$Ar^2$ is more preferably selected from pyridine, pyrimidine, pyridazine, pyrazine, triazine, carbazole, imidazole, pyrazole, triazole, benzimidazole, benzimidazoisoquinoline, imidazophenanthridine, benzimidazophenanthridine, bathocuproin, benzimidazobenzimidazole, quinoline, quinazoline, phenanthroline, phenanthridine, diazaphenanthrene, and acridine, each of which may be substituted by one or more $R^5$ radicals.

Groups of the formula (A) are preferably selected from the following groups:

Formula (A-1)

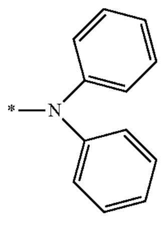

-continued
Formula (A-2)
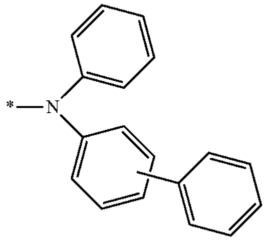
Formula (A-3)
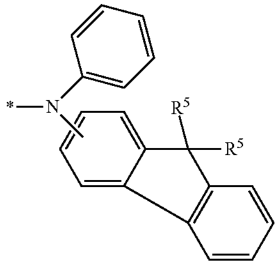
Formula (A-4)
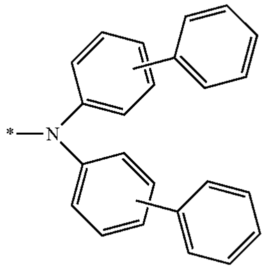
Formula (A-5)
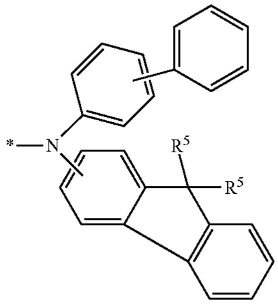
Formula (A-6)
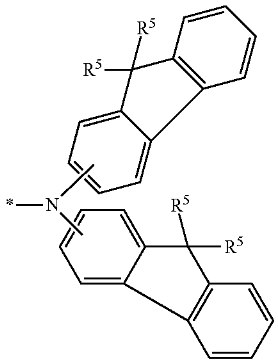
-continued
Formula (A-7)
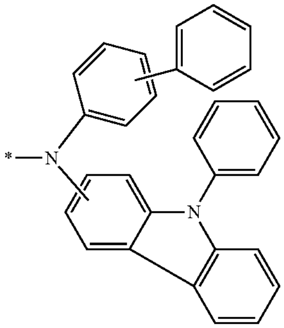
Formula (A-8)
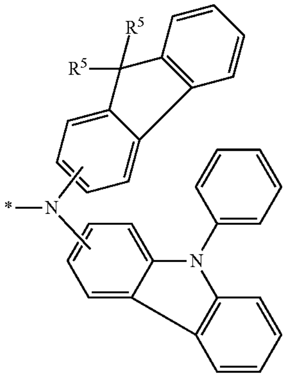
Formula (A-9)
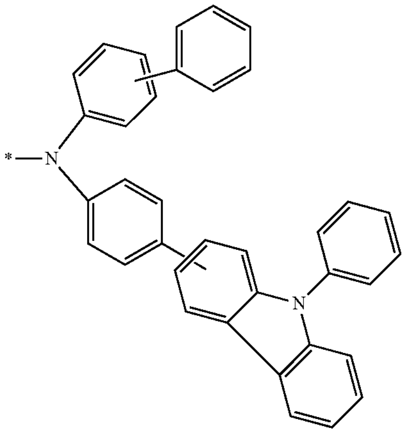
Formula (A-10)
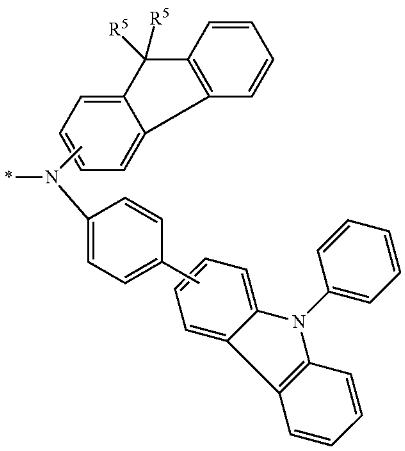

-continued
Formula (A-11)
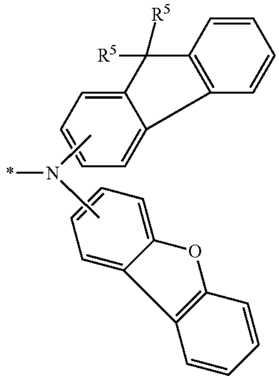
Formula (A-12)
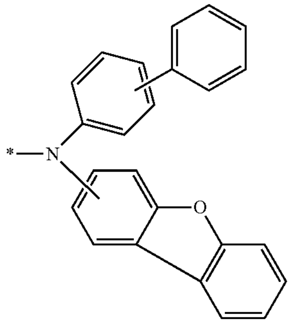
Formula (A-13)
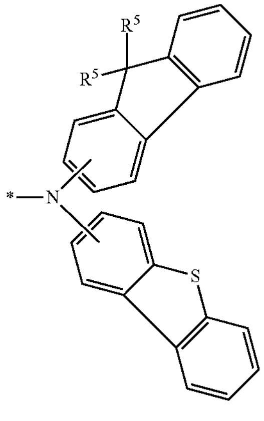
Formula (A-14)
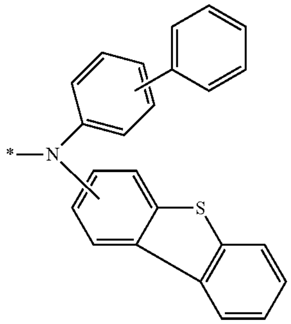
-continued
Formula (A-15)
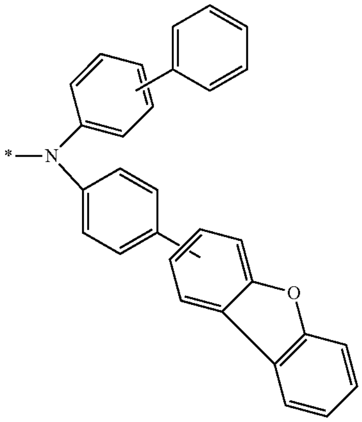
Formula (A-16)
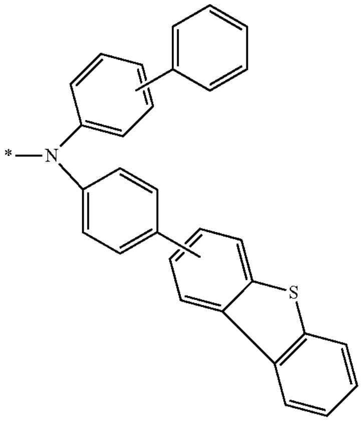
Formula (A-17)
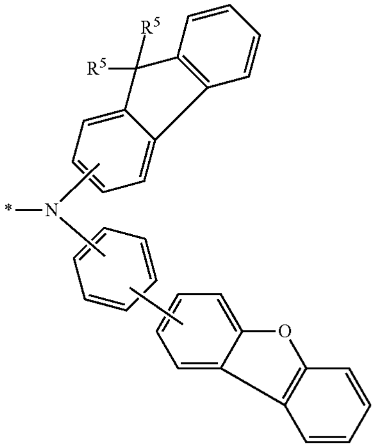

-continued
Formula (A-18)
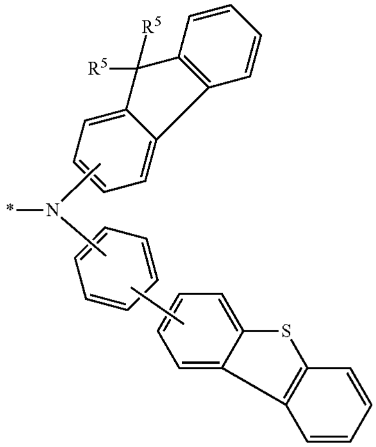
Formula (A-19)
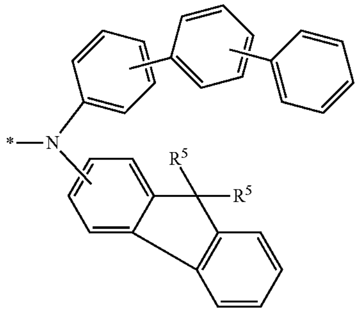
Formula (A-20)
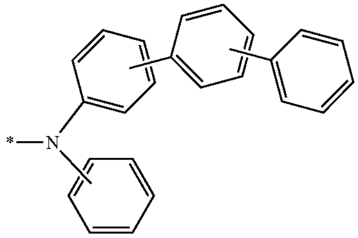
Formula (A-21)
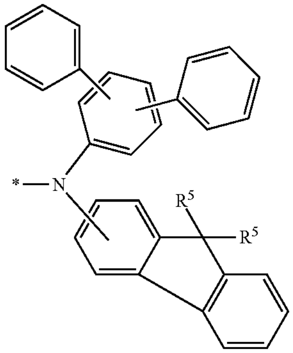
-continued
Formula (A-22)
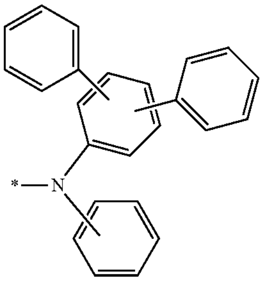
Formula (A-23)
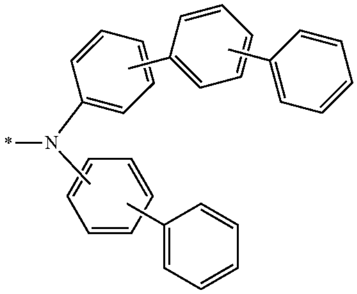
Formula (A-24)
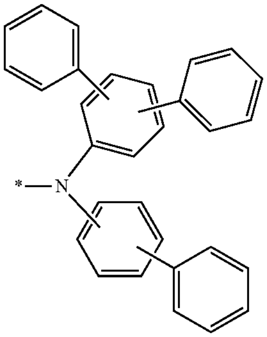
Formula (A-25)
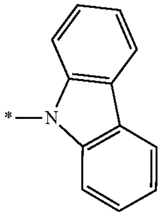
Formula (A-26)
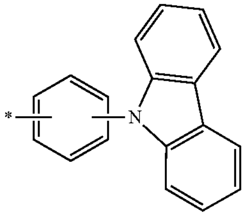
Formula (A-27)
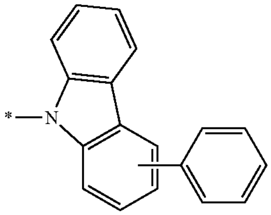

-continued
Formula (A-28)
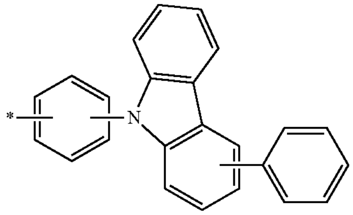
Formula (A-29)
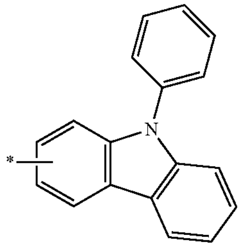
Formula (A-30)
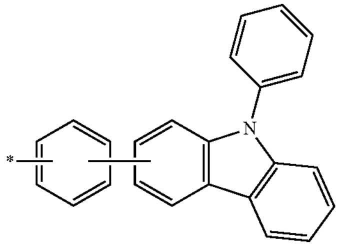
Formula (A-31)
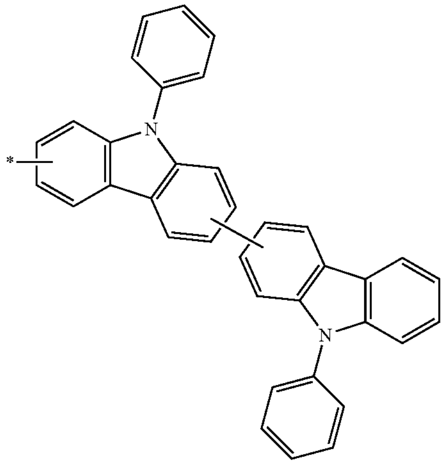
Formula (A-32)
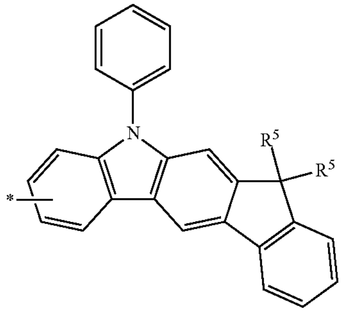
-continued
Formula (A-33)
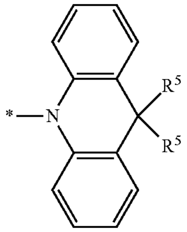
Formula (A-34)
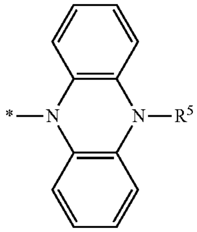
Formula (A-35)
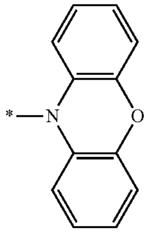
Formula (A-36)
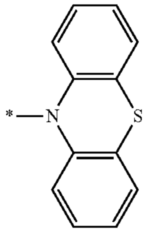
Formula (A-37)
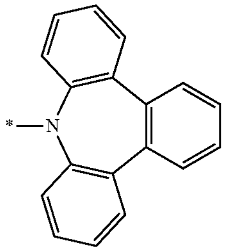
Formula (A-38)
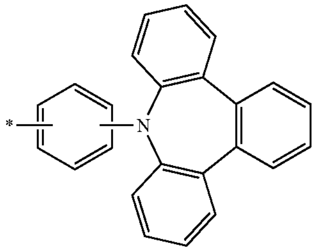

-continued
Formula (A-39)
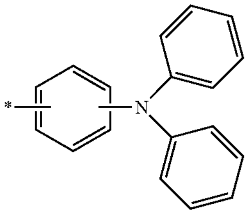
Formula (A-40)
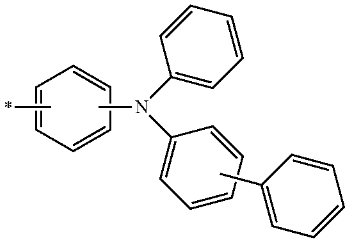
Formula (A-41)
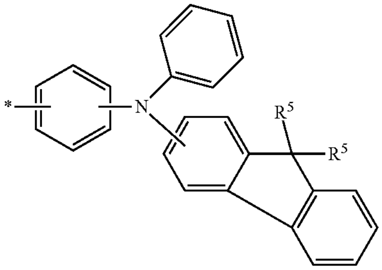
Formula (A-42)
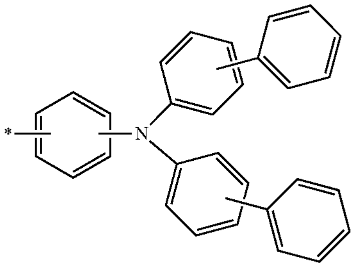
Formula (A-43)
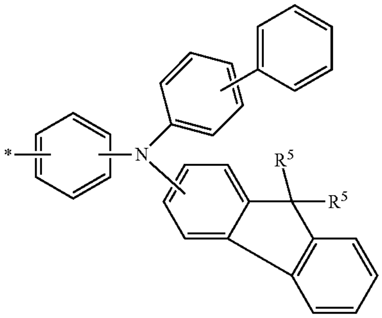
-continued
Formula (A-44)
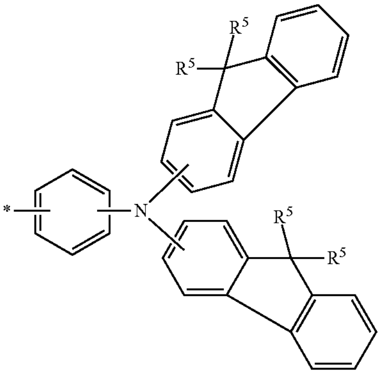
Formula (A-45)
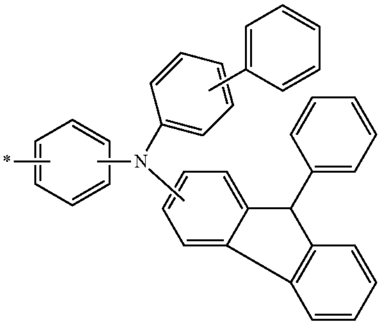
Formula (A-46)
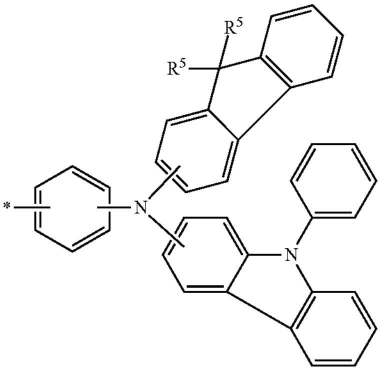
Formula (A-47)
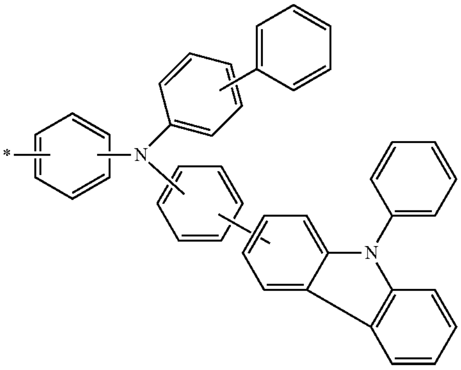

-continued
Formula (A-48)
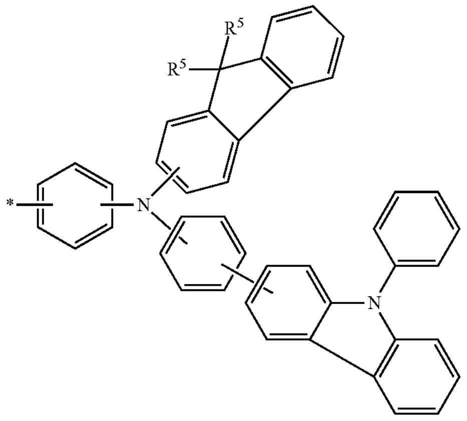
Formula (A-49)
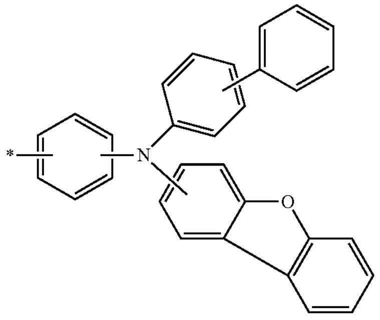
Formula (A-50)
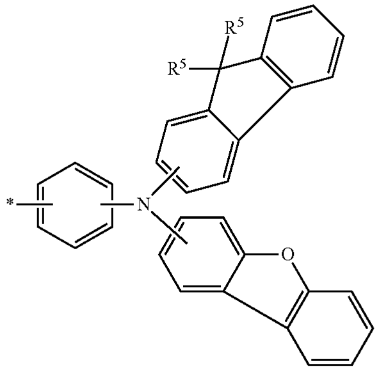
Formula (A-51)
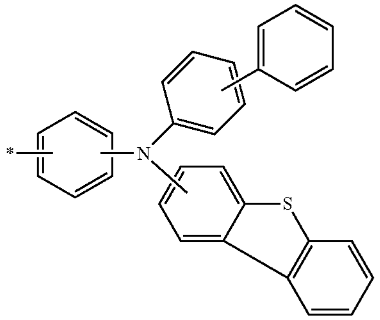
-continued
Formula (A-52)
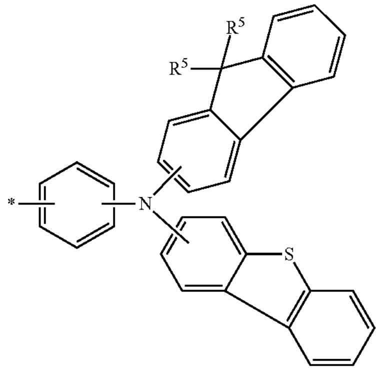
Formula (A-53)
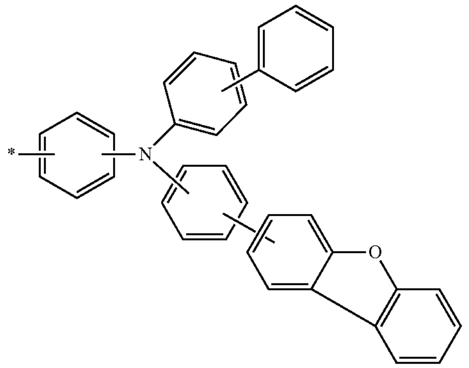
Formula (A-54)
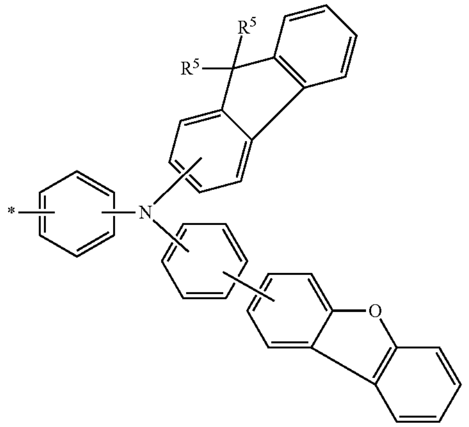
Formula (A-55)
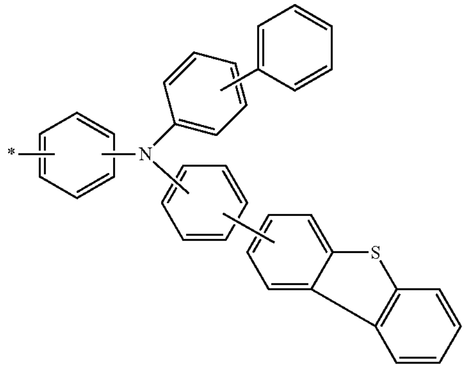

-continued
Formula (A-56)
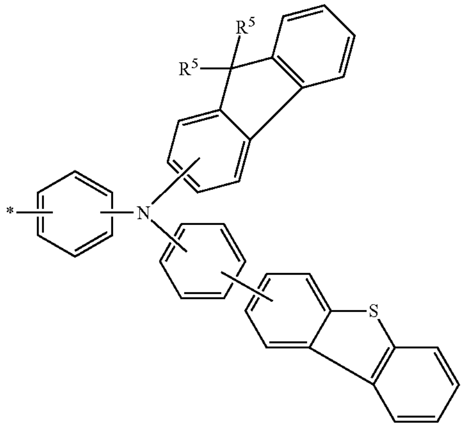
Formula (A-57)
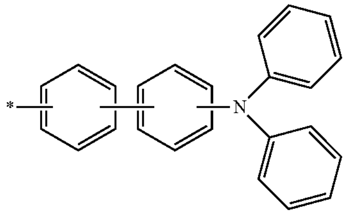
Formula (A-58)
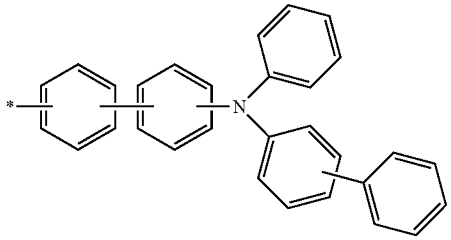
Formula (A-59)
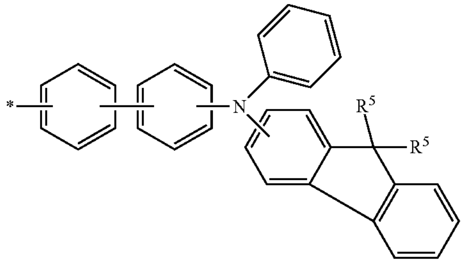
Formula (A-60)
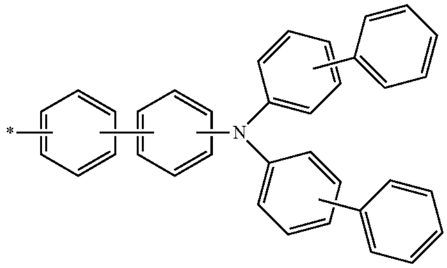
-continued
Formula (A-61)
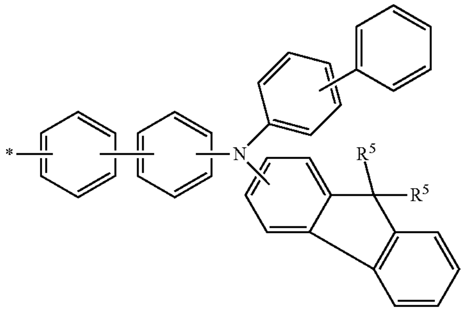
Formula (A-62)
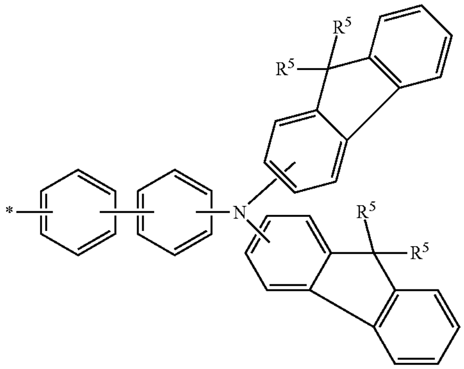
Formula (A-63)
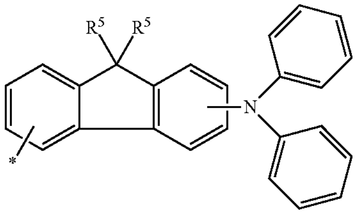
Formula (A-64)
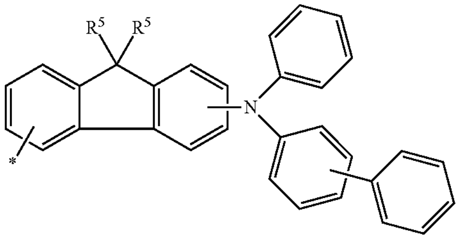
Formula (A-65)
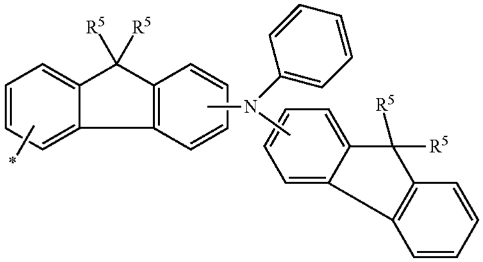

-continued

Formula (A-66)

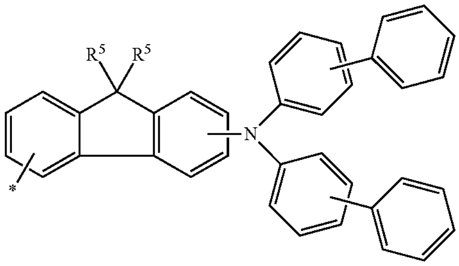

Formula (A-67)

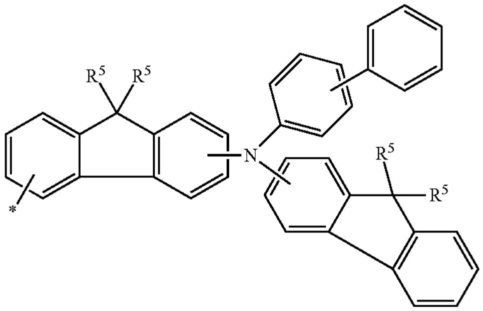

Formula (A-68)

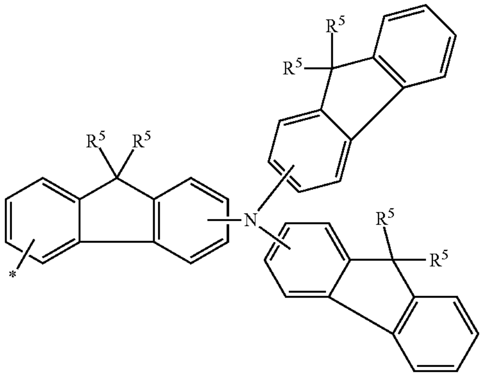

where the groups are bonded to the rest of the formula via the bond identified by *, where $R^5$ is as defined above, and preferably conforms to the preferred embodiments specified above, and where the groups may each be substituted by an $R^5$ radical at the positions shown as unsubstituted, but are preferably unsubstituted in these positions.

Groups of the formula (H) are preferably selected from the following groups:

Formula (H-1)

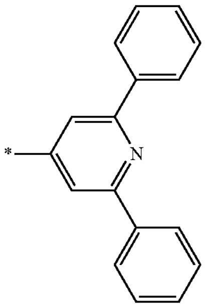

-continued

Formula (H-2)

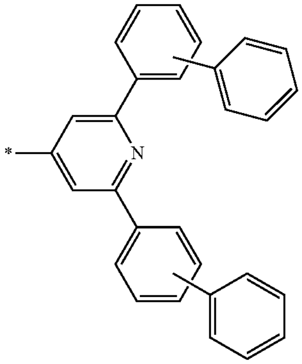

Formula (H-3)

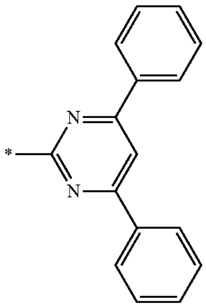

Formula (H-4)

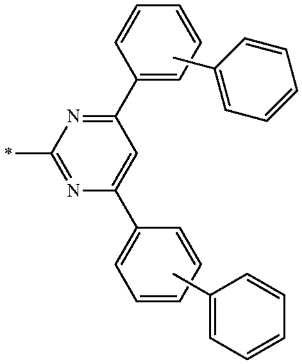

Formula (H-5)

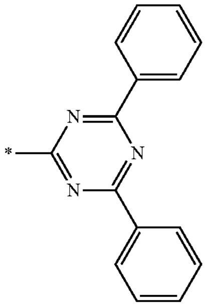

-continued
Formula (H-6)
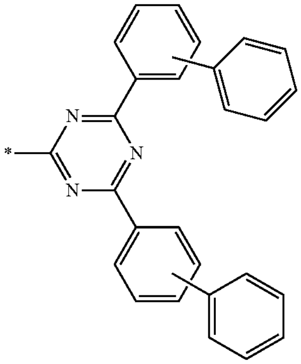
Formula (H-7)
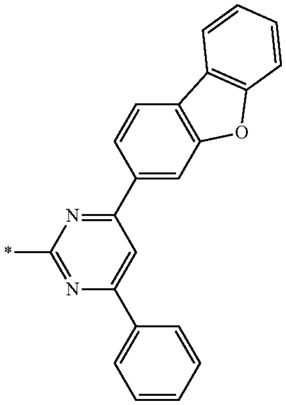
Formula (H-8)
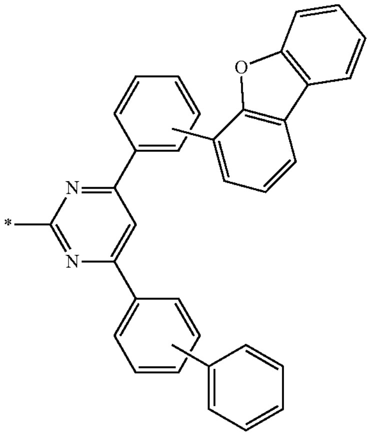
Formula (H-9)
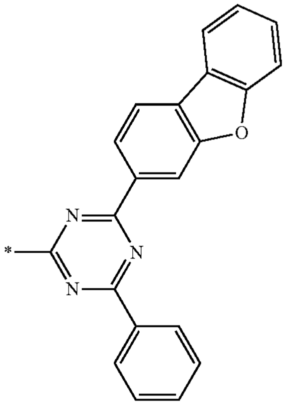
-continued
Formula (H-10)
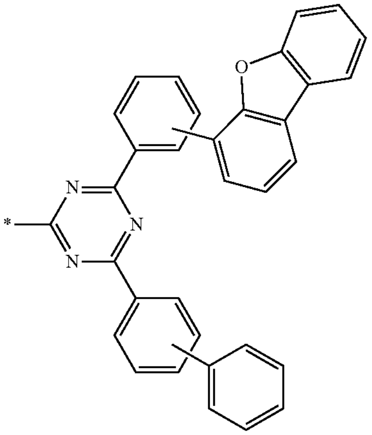
Formula (H-11)
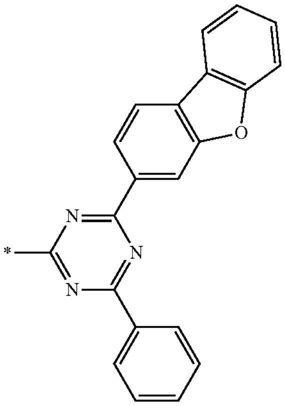
Formula (H-12)
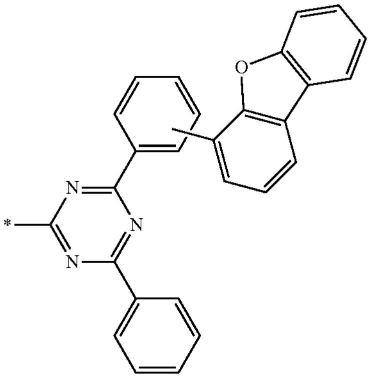
Formula (H-13)
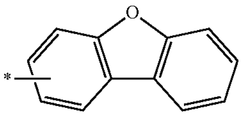
Formula (H-14)
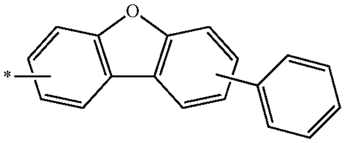
Formula (H-15)
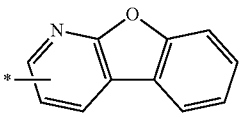

-continued
Formula (H-16)
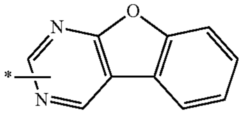
Formula (H-17)
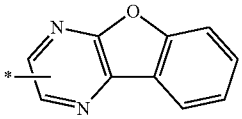
Formula (H-18)
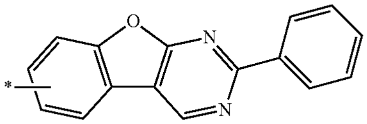
Formula (H-19)
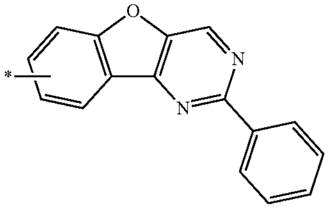
Formula (H-20)
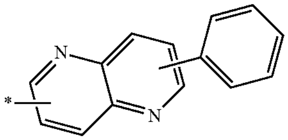
Formula (H-21)
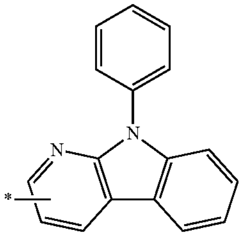
Formula (H-22)
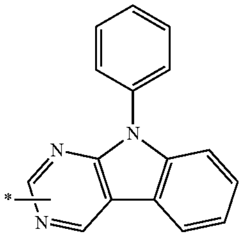
Formula (H-23)
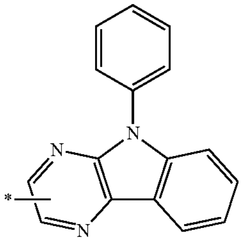
-continued
Formula (H-24)
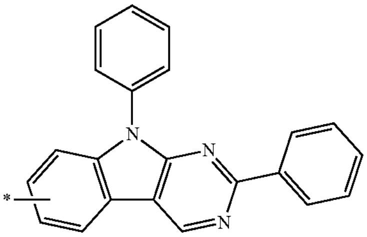
Formula (H-25)
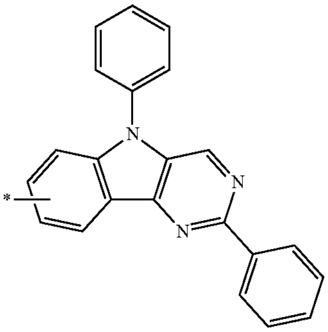
Formula (H-26)
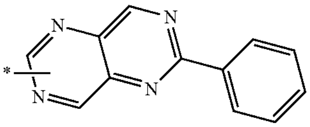
Formula (H-27)
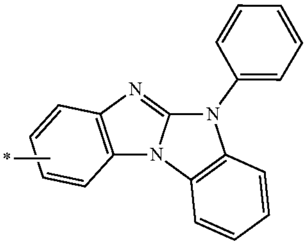
Formula (H-28)
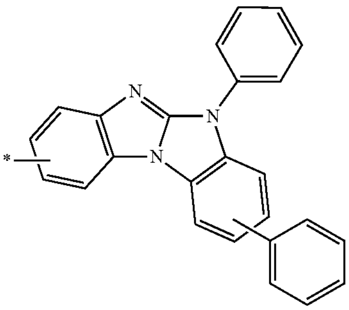

-continued
Formula (H-29)
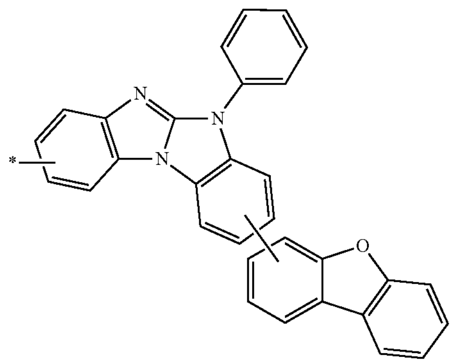
Formula (H-30)
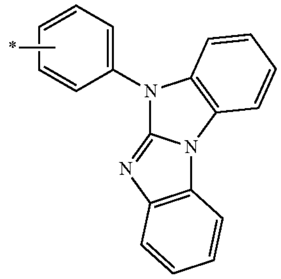
Formula (H-31)
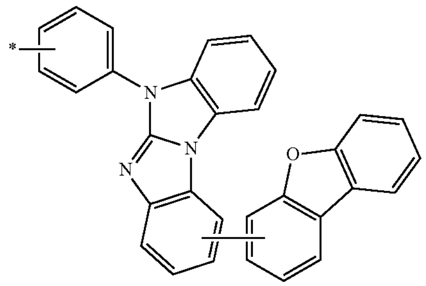
Formula (H-32)
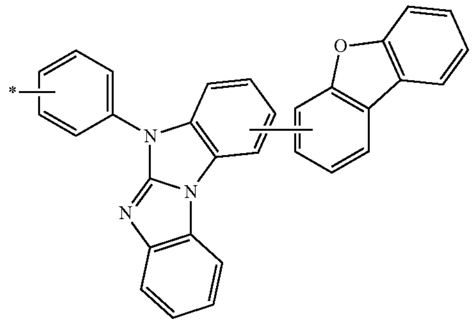
Formula (H-33)
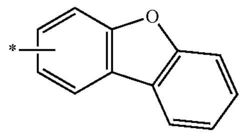
Formula (H-34)
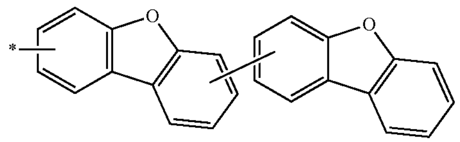
-continued
Formula (H-35)
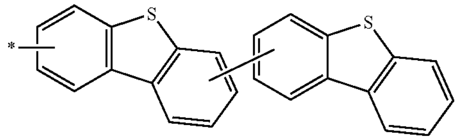
Formula (H-36)
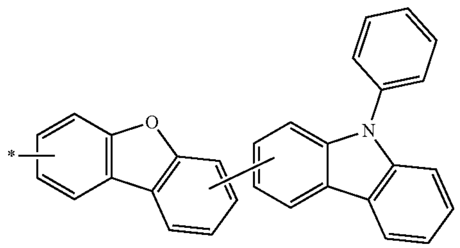
Formula (H-37)
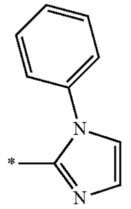
Formula (H-38)
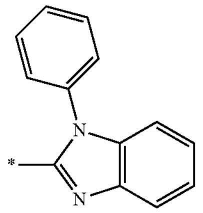
Formula (H-39)
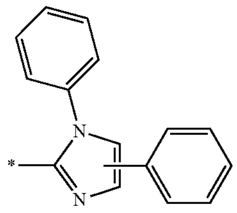
Formula (H-40)
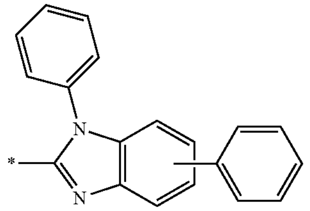
Formula (H-41)
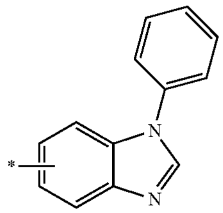

-continued

Formula (H-42)

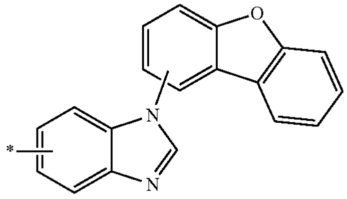

Formula (H-43)

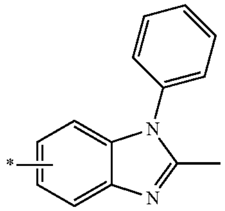

Formula (H-44)

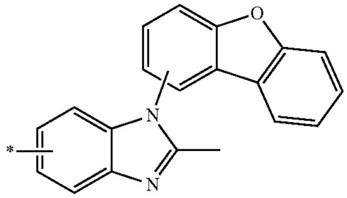

Formula (H-45)

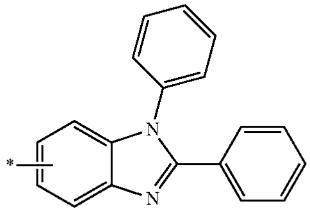

Formula (H-46)

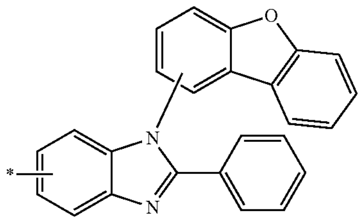

Formula (H-47)

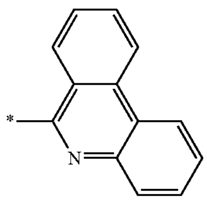

-continued

Formula (H-48)

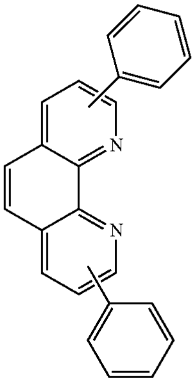

Formula (H-49)

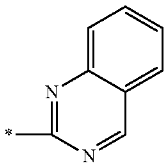

Formula (H-50)

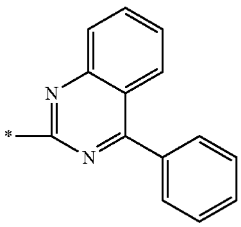

Formula (H-51)

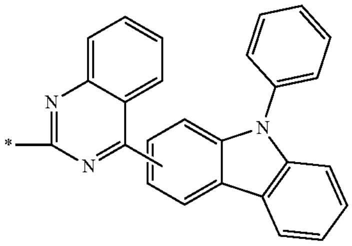

Formula (H-52)

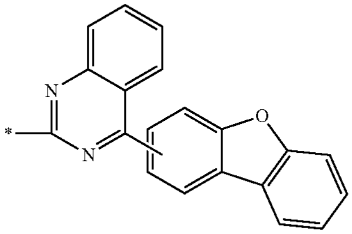

where the groups are bonded to the rest of the formula via the bond identified by *, where $R^5$ is as defined above, and preferably conforms to the preferred embodiments specified above, and where the groups may each be substituted by an $R^5$ radical at the positions shown as unsubstituted, but are preferably unsubstituted in these positions.

Preferably, $R^5$ is the same or different at each instance and is selected from H, D, F, CN, $Si(R^6)_3$, $N(R^6)_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned may each be substituted by one or more $R^6$ radicals; and where one or more $CH_2$ groups in the alkyl or alkoxy groups mentioned may be replaced by —C≡C—, —$R^6C$═$CR^6$—, $Si(R^6)_2$, C═O, C═$NR^6$, —$NR^6$—, —O—, —S—, —C(═O)O— or —C(═O)$NR^6$—.

Preferred embodiments of the formula (I) conform to the following formulae (I-H-1) to (I-H-7) and (I-A-1) to (I-A-7):

Formula (I-H-1)

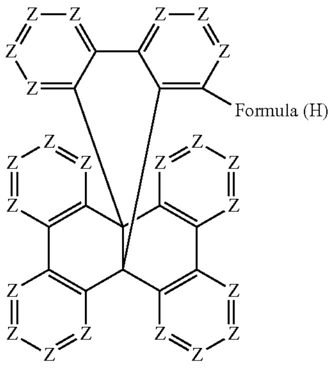

Formula (I-H-2)

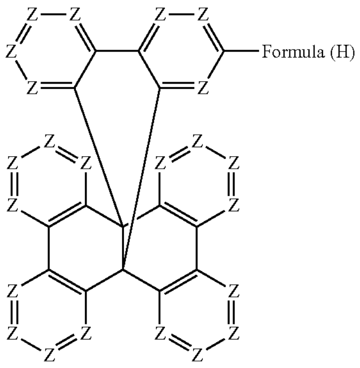

Formula (I-H-3)

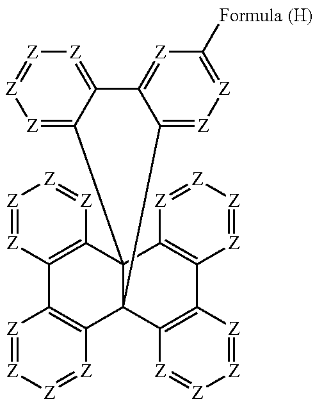

-continued

Formula (I-H-4)

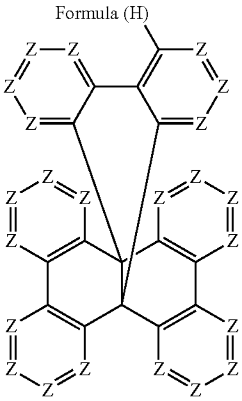

Formula (I-H-5)

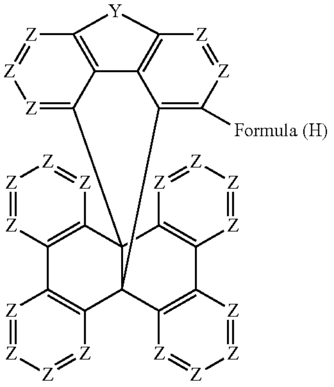

Formula (I-H-6)

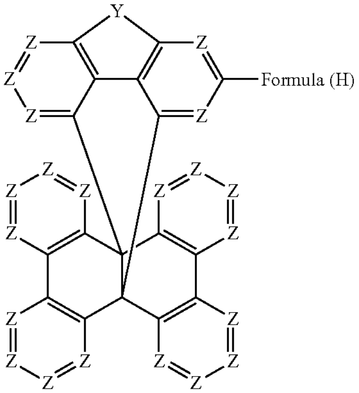

Formula (I-H-7)

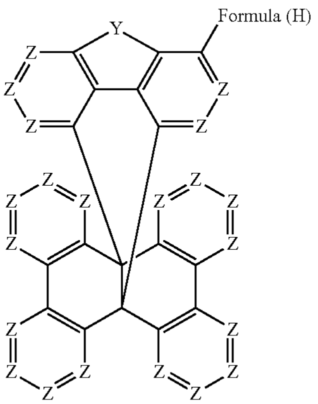

-continued

Formula (I-A-1)

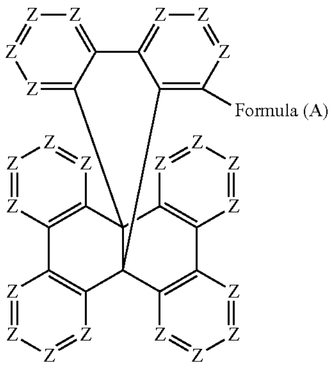

Formula (I-A-2)

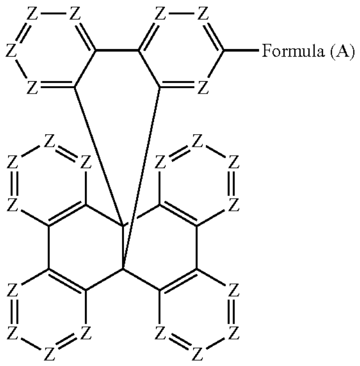

Formula (I-A-3)

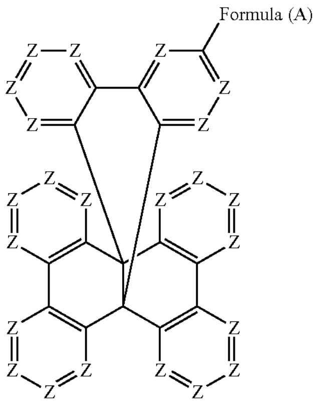

Formula (I-A-4)

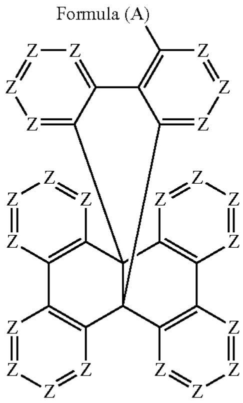

-continued

Formula (I-A-5)

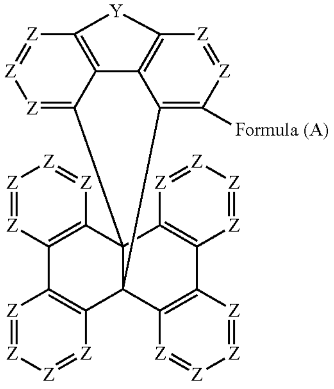

Formula (I-A-6)

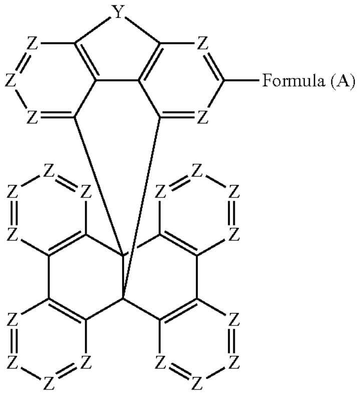

Formula (I-A-7)

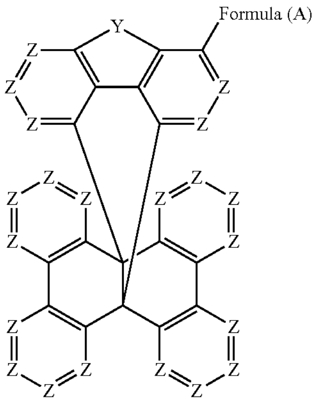

where the groups that occur are as defined above and preferably conform to the preferred embodiments thereof, and where "formula (A)" is a group of the formula (A) as defined above, and where "formula (H)" is a group of the formula (H) as defined above. In the abovementioned formulae, it is especially preferable that Z is $CR^1$.

Preferred embodiments of the formula (II) conform to the following formulae (II-A-1) to (II-A-3):

Formula (II-A-1)

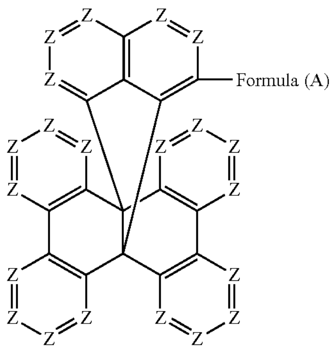

Formula (II-A-2)

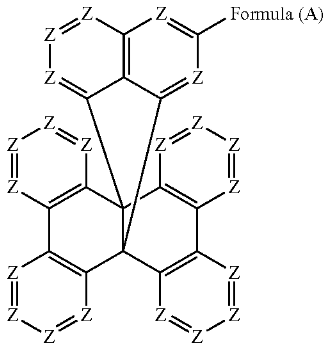

Formula (II-A-3)

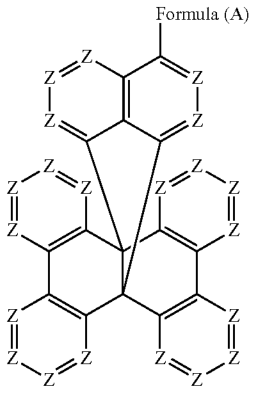

where the groups that occur are as defined above and preferably conform to the preferred embodiments thereof, and where "formula (A)" is a group of the formula (A) as defined above. In the abovementioned formulae, it is especially preferable that Z is $CR^1$.

Among the abovementioned formulae, particular preference is given to the formula (II-A-3).

Preferred embodiments of the formula (III) conform to the following formulae (III-A-1) to (III-A-3):

Formula (III-A-1)

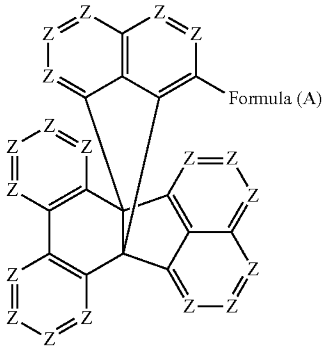

Formula (III-A-2)

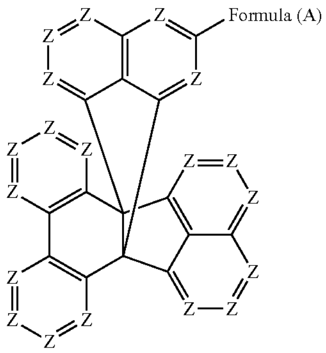

Formula (III-A-3)

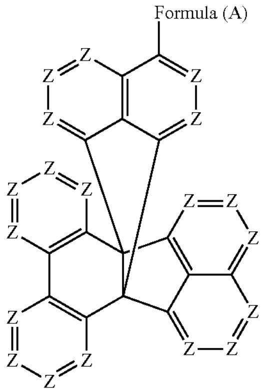

where the groups that occur are as defined above and preferably conform to the preferred embodiments thereof, and where "formula (A)" is a group of the formula (A) as defined above. In the abovementioned formulae, it is especially preferable that Z is $CR^1$.

Among the abovementioned formulae, particular preference is given to the formula (III-A-3).

Preferred embodiments of the formula (IV) conform to the following formulae (IV-A-1) to (IV-A-3):

-continued

Formula (IV-A-1)

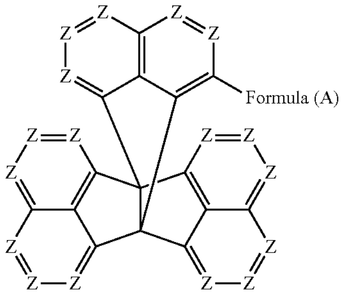

Formula (IV-A-2)

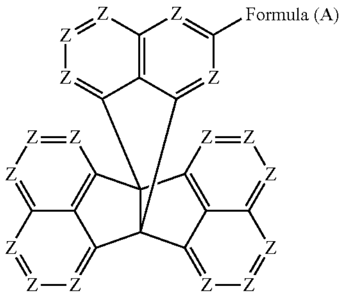

Formula (IV-A-3)

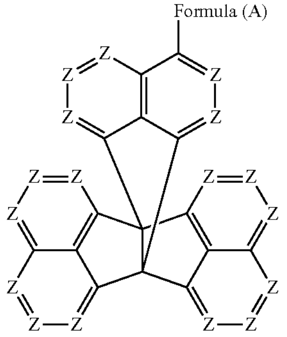

where the groups that occur are as defined above and preferably conform to the preferred embodiments thereof, and where “formula (A)” is a group of the formula (A) as defined above. In the abovementioned formulae, it is especially preferable that Z is $CR^1$.

Among the abovementioned formulae, particular preference is given to the formula (IV-A-3).

Preferred compounds of the formulae (I) to (IV) are shown in the following table:

1

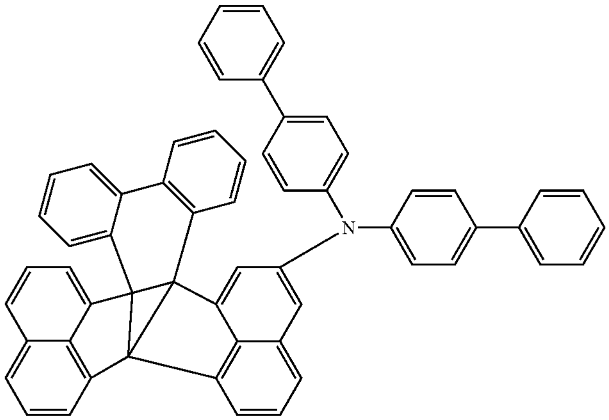 [SMILES: c1ccc(-c2ccc(N(c3ccc(-c4ccccc4)cc3)c3cc4c5c(cccc5c3)C35c6cccc7cccc(c67)C36c3ccccc3-c3ccccc3C465)cc2)cc1]

2

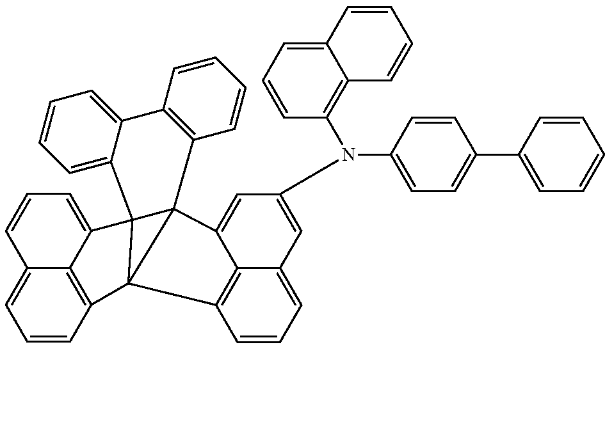 [SMILES: c1ccc(-c2ccc(N(c3cc4c5c(cccc5c3)C35c6cccc7cccc(c67)C36c3ccccc3-c3ccccc3C465)c3cccc4ccccc34)cc2)cc1]

-continued
3
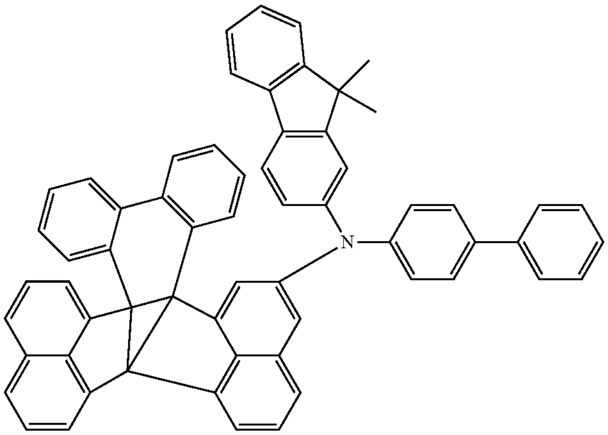 [SMILES: CC1(C)c2ccccc2-c2ccc(N(c3ccc(-c4ccccc4)cc3)c3cc4c5c(cccc5c3)C35c6cccc7cccc(c67)C36c3ccccc3-c3ccccc3C465)cc21]
4
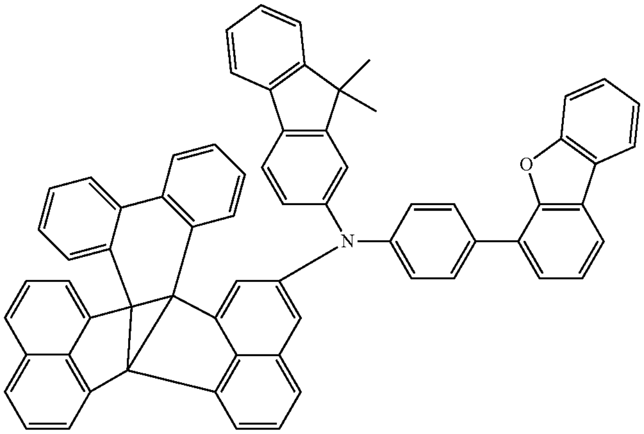 [SMILES: CC1(C)c2ccccc2-c2ccc(N(c3ccc(-c4cccc5c4oc4ccccc45)cc3)c3cc4c5c(cccc5c3)C35c6cccc7cccc(c67)C36c3ccccc3-c3ccccc3C465)cc21]
5
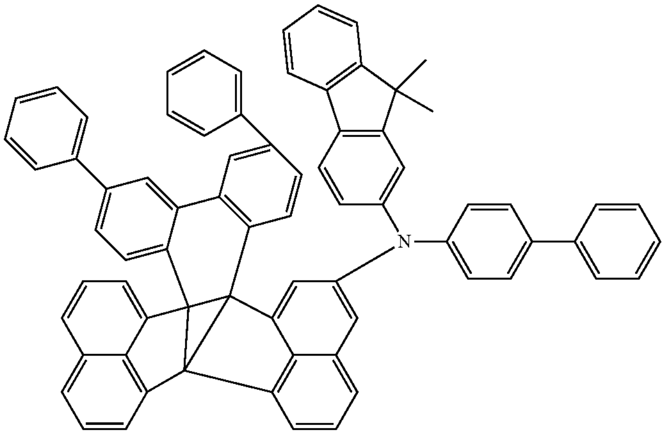 [SMILES: CC1(C)c2ccccc2-c2ccc(N(c3ccc(-c4ccccc4)cc3)c3cc4c5c(cccc5c3)C35c6cccc7cccc(c67)C36c3ccc(-c7ccccc7)cc3-c3cc(-c7ccccc7)ccc3C465)cc21]

-continued
6
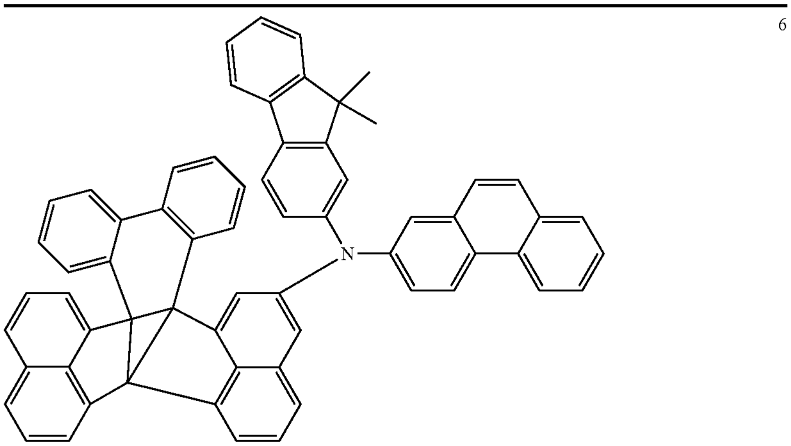
7
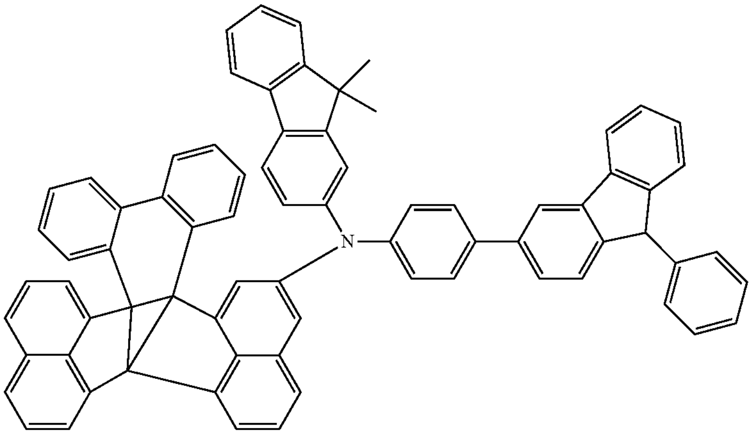 [SMILES: CC1(C)c2ccccc2-c2ccc(N(c3ccc(-c4ccc5c(c4)-c4ccccc4C5c4ccccc4)cc3)c3cc4c5c(cccc5c3)C35c6cccc7cccc(c67)C36c3ccccc3-c3ccccc3C465)cc21]
8
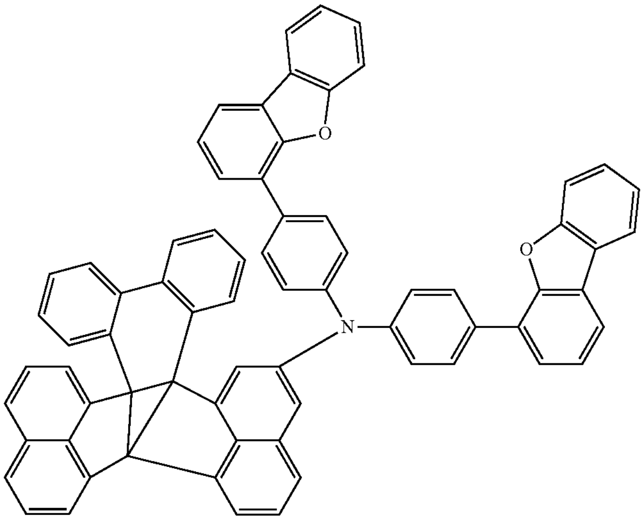 [SMILES: c1ccc2c(c1)-c1ccccc1C13c4cc(N(c5ccc(-c6cccc7c6oc6ccccc67)cc5)c5ccc(-c6cccc7c6oc6ccccc67)cc5)cc5cccc(c45)C14c1cccc5cccc(c15)C234]

-continued
9
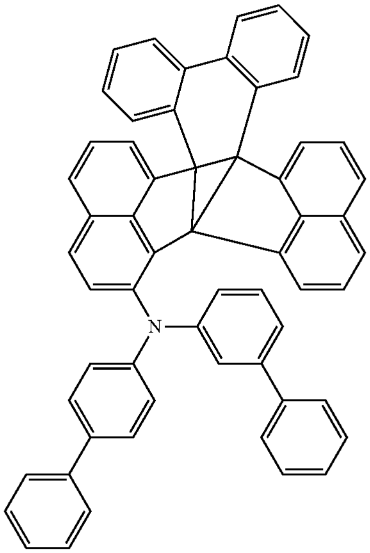 [SMILES: c1ccc(-c2ccc(N(c3cccc(-c4ccccc4)c3)c3ccc4cccc5c4c3C34c6cccc7cccc(c67)C36c3ccccc3-c3ccccc3C564)cc2)cc1]
10
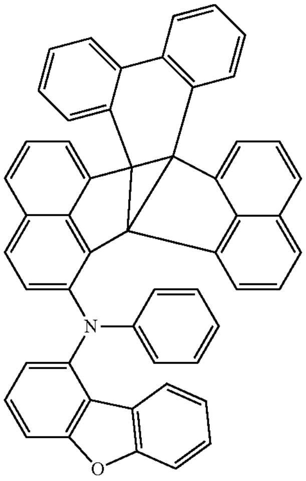 [SMILES: c1ccc(N(c2ccc3cccc4c3c2C23c5cccc6cccc(c56)C25c2ccccc2-c2ccccc2C453)c2cccc3oc4ccccc4c23)cc1]
11
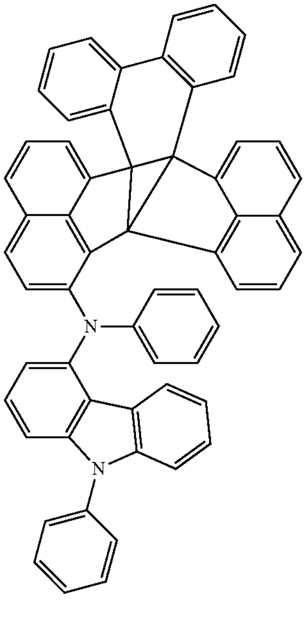 [SMILES: c1ccc(N(c2ccc3cccc4c3c2C23c5cccc6cccc(c56)C25c2ccccc2-c2ccccc2C453)c2cccc3c2c2ccccc2n3-c2ccccc2)cc1]

-continued
12
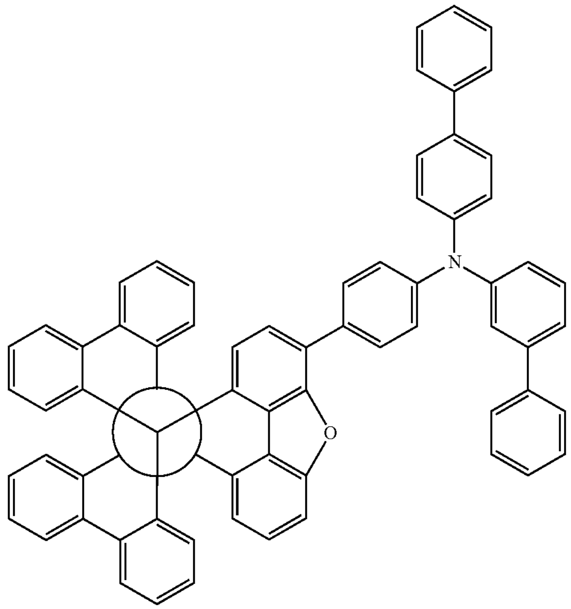 [SMILES: Cc1ccccc1-c1ccccc1C(c1ccccc1-c1ccccc1C)c1ccc(-c2ccc(N(c3ccc(-c4ccccc4)cc3)c3cccc(-c4ccccc4)c3)cc2)c2oc3cccc(C)c3c12]
13
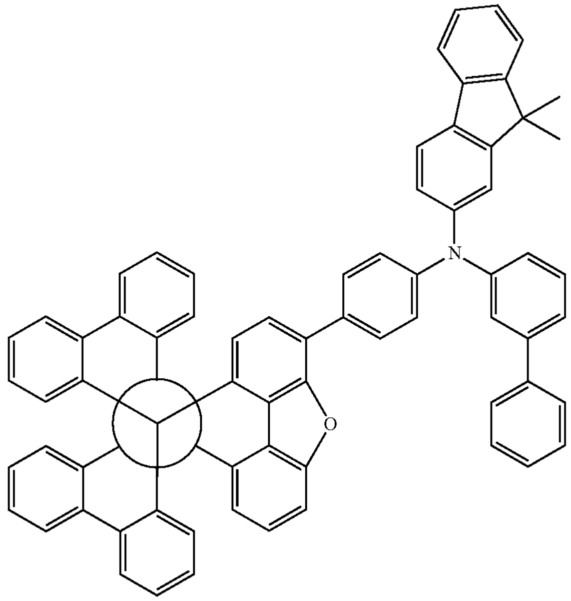 [SMILES: Cc1ccccc1-c1ccccc1C(c1ccccc1-c1ccccc1C)c1ccc(-c2ccc(N(c3cccc(-c4ccccc4)c3)c3ccc4c(c3)C(C)(C)c3ccccc3-4)cc2)c2oc3cccc(C)c3c12]

-continued
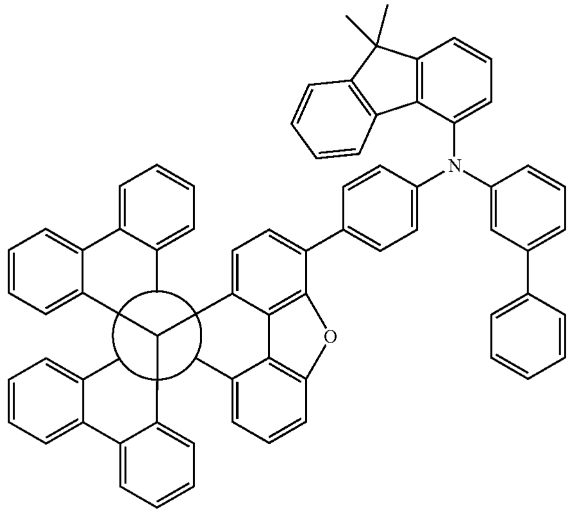 [SMILES: Cc1ccccc1-c1ccccc1C(c1ccccc1-c1ccccc1C)c1ccc(-c2ccc(N(c3cccc(-c4ccccc4)c3)c3cccc4c3-c3ccccc3C4(C)C)cc2)c2oc3cccc(C)c3c12]
14
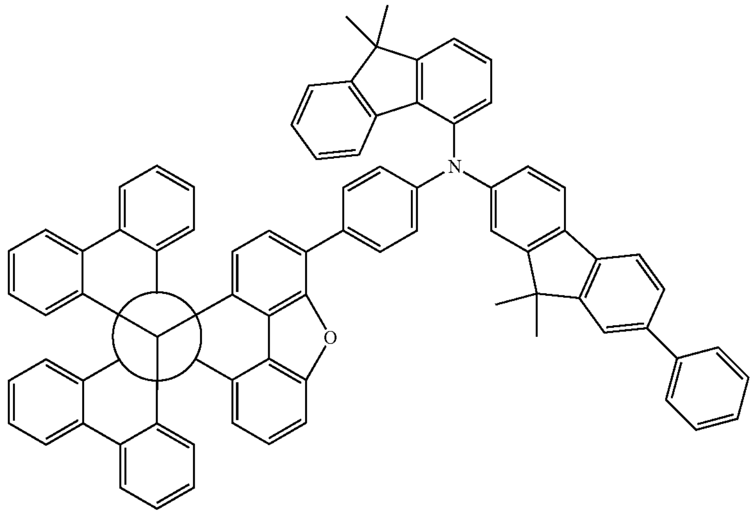 [SMILES: Cc1ccccc1-c1ccccc1C(c1ccccc1-c1ccccc1C)c1ccc(-c2ccc(N(c3ccc4c(c3)C(C)(C)c3cc(-c5ccccc5)ccc3-4)c3cccc4c3-c3ccccc3C4(C)C)cc2)c2oc3cccc(C)c3c12]
15
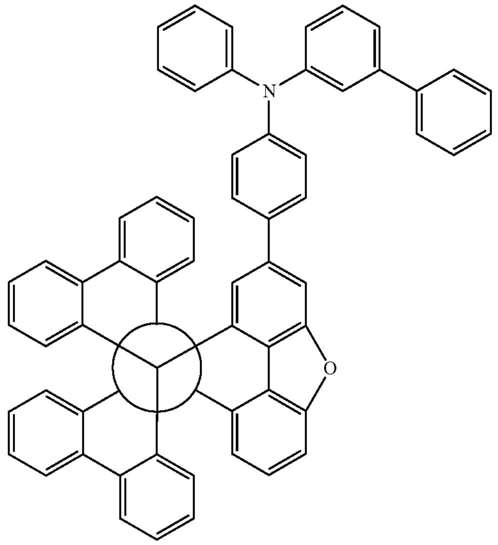 [SMILES: Cc1ccccc1-c1ccccc1C(c1ccccc1-c1ccccc1C)c1cc(-c2ccc(N(c3ccccc3)c3cccc(-c4ccccc4)c3)cc2)cc2oc3cccc(C)c3c12]
16

-continued
17
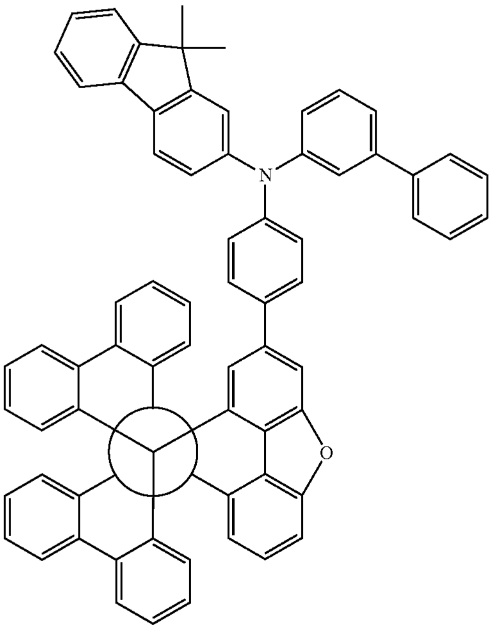 [SMILES: Cc1ccccc1-c1ccccc1C(c1ccccc1-c1ccccc1C)c1cc(-c2ccc(N(c3cccc(-c4ccccc4)c3)c3ccc4c(c3)C(C)(C)c3ccccc3-4)cc2)cc2oc3cccc(C)c3c12]
18
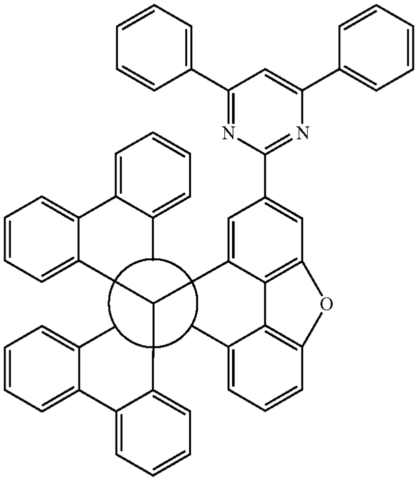 [SMILES: Cc1ccccc1-c1ccccc1C(c1ccccc1-c1ccccc1C)c1cc(-c2nc(-c3ccccc3)cc(-c3ccccc3)n2)cc2oc3cccc(C)c3c12]
19
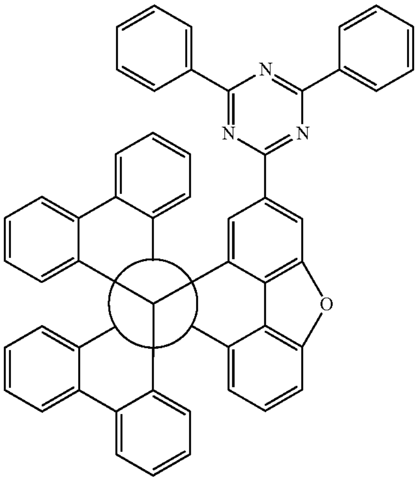 [SMILES: Cc1ccccc1-c1ccccc1C(c1ccccc1-c1ccccc1C)c1cc(-c2nc(-c3ccccc3)nc(-c3ccccc3)n2)cc2oc3cccc(C)c3c12]

-continued

20

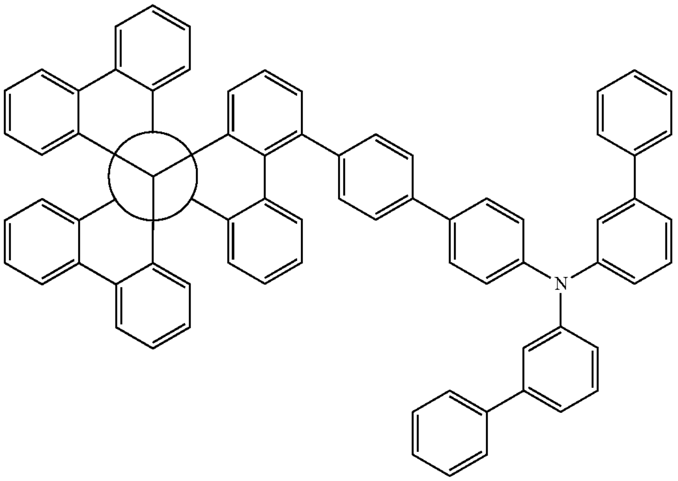 [SMILES: Cc1ccccc1-c1ccccc1C(c1ccccc1-c1ccccc1C)c1cccc(-c2ccc(-c3ccc(N(c4cccc(-c5ccccc5)c4)c4cccc(-c5ccccc5)c4)cc3)cc2)c1-c1ccccc1C]

21

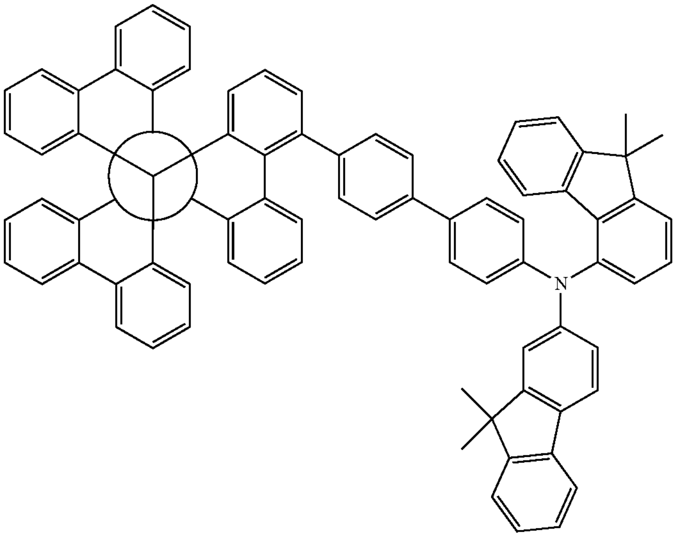 [SMILES: Cc1ccccc1-c1ccccc1C(c1ccccc1-c1ccccc1C)c1cccc(-c2ccc(-c3ccc(N(c4ccc5c(c4)C(C)(C)c4ccccc4-5)c4cccc5c4-c4ccccc4C5(C)C)cc3)cc2)c1-c1ccccc1C]

22

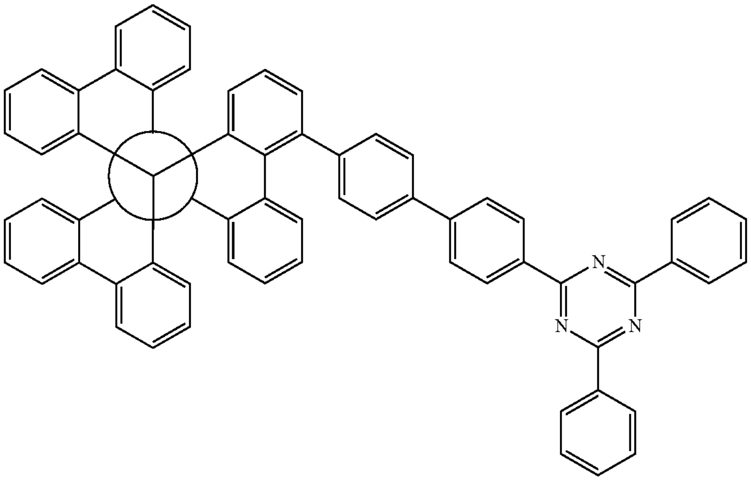 [SMILES: Cc1ccccc1-c1ccccc1C(c1ccccc1-c1ccccc1C)c1cccc(-c2ccc(-c3ccc(-c4nc(-c5ccccc5)nc(-c5ccccc5)n4)cc3)cc2)c1-c1ccccc1C]

The compounds of the invention can be prepared by means of known synthesis methods.

Compounds of the formula (I) are synthesized proceeding from alkoxy-bromo-biphenyl derivatives, which are converted by reaction with lithium organyls or magnesium to reactive nucleophiles, and then added onto an optionally functionalized spiro[9H-fluorene-9,9'(10'H)-phenanthrene]-10'-one (see scheme 1). The tertiary alcohol thus obtained cyclizes under acid catalysis with intramolecular rearrangement to give the alkoxy-functionalized [4.4.4]-propellane (steps 1 and 2). A methyl ether cleavage in molten pyridinium hydrochloride (step 3) and subsequent esterification of the phenol formed with trifluoromethanesulfonic anhydride (step 4) leads to the reactive triflates, which are then reacted under palladium or copper catalysis by standard methods known from the literature with secondary amines in C—N couplings (e.g. Hartwig-Buchwald coupling) or with aryl/heteroarylboronic acids or -boronic esters, organotin or -zinc compounds in C—C couplings (e.g. Suzuki, Stille, Negishi coupling, etc.) to give the compounds of the invention (step 5).

Scheme 1:

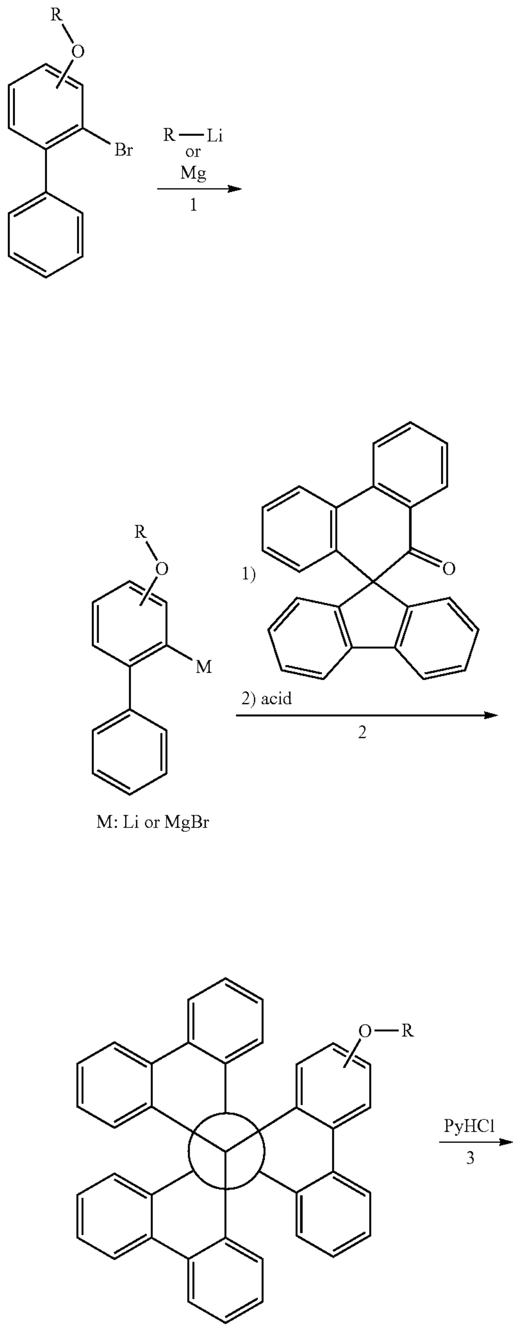

-continued

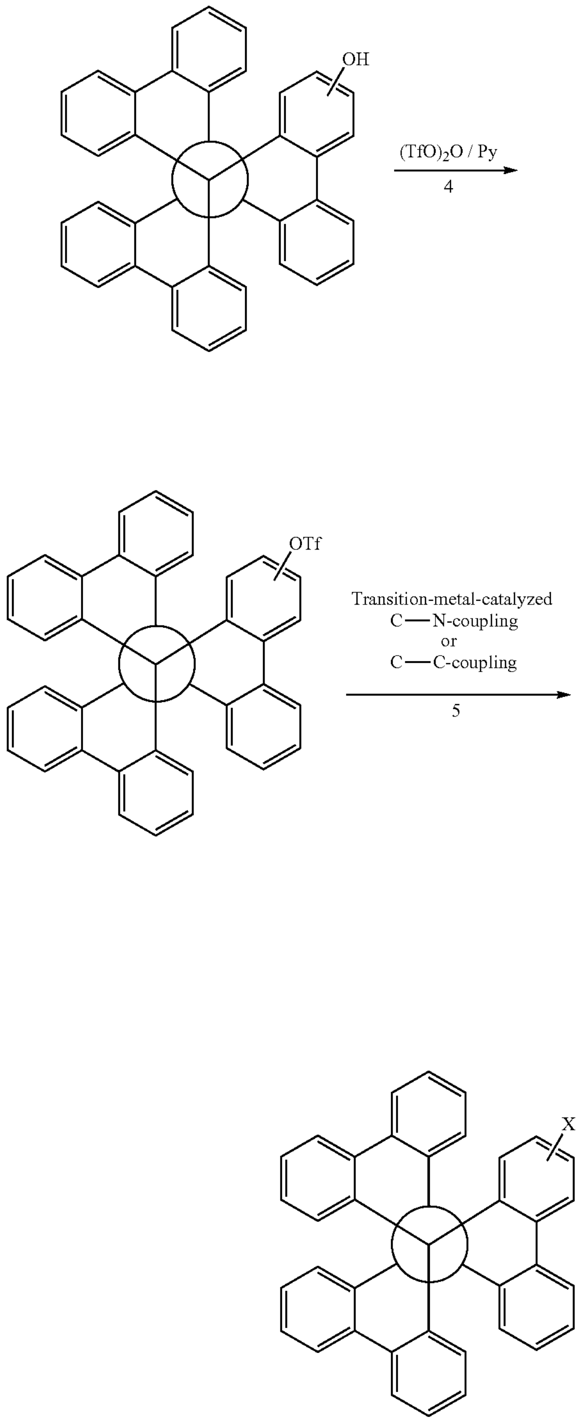

X: —N(Ar)$_2$ aryl or heteroaryl, where Ar = aryl or heteroaryl
M: Li or MgBr
R: any organic radical, preferably aryl or alkyl, more preferably alkyl
The compounds may bear a substituent at any of the positions shown as unsubstituted.

In a modification of the synthesis sequence shown in scheme 1 (scheme 1a), rather than the bromo-alkoxy-biphenyl derivative, it is possible to use a corresponding bridged derivative, for example a bromo-alkoxy-substituted dibenzofuran derivative. This affords, by the same synthesis route as described in scheme 1, bridged derivatives of the formula (I):

Scheme 1

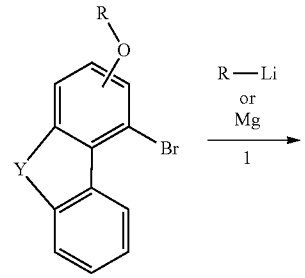

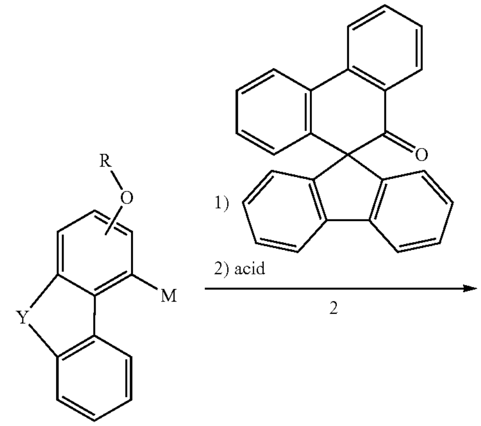

M: Li or MgBr

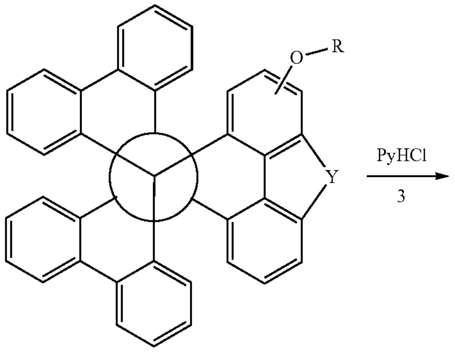

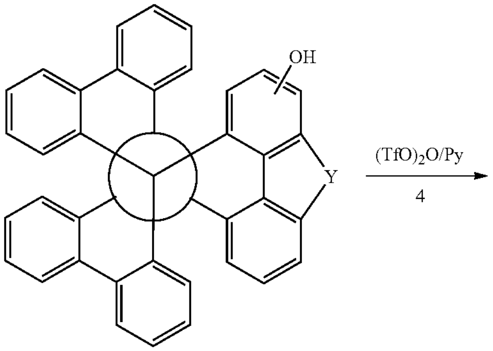

-continued

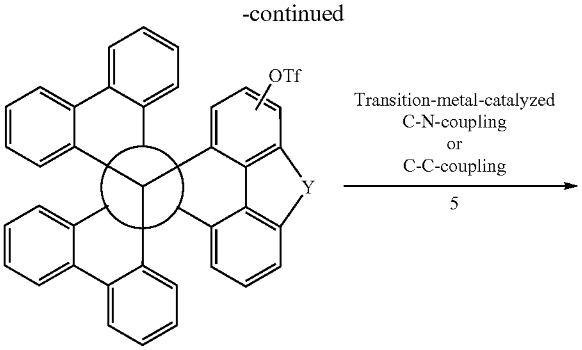

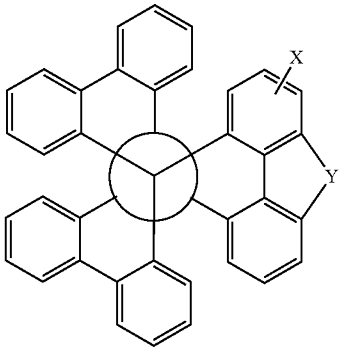

X: —N(Ar)$_2$ or aryl or heteroaryl, where Ar = aryl or heteroaryl Y: BR, NR, O, S, C(R)$_2$ and Si(R)$_2$, preferably O or S, more preferably O M: Li or MgBr R: any organic radical, preferably aryl or alkyl, more preferably alkyl The compounds may bear a substituent at any of the positions shown as unsubstituted.

Analogously to the reaction sequence shown in scheme 1, inventive compounds of the formula (III) can be obtained using alkoxy-bromo-naphthalene derivatives rather than alkoxy-bromo-biphenyl derivatives (scheme 2).

Scheme 2

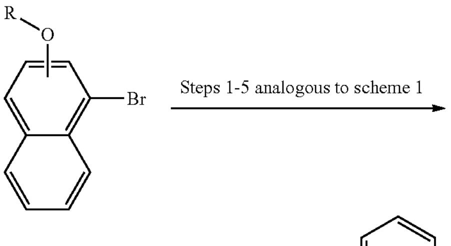

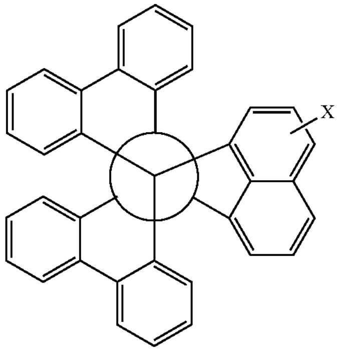

X: —N(Ar)$_2$ or aryl or heteroaryl, where Ar = aryl or heteroaryl R: any organic radical, preferably aryl or alkyl, more preferably alkyl The compounds may bear a substituent at any of the positions shown as unsubstituted.

Compounds of the formula (III) can be prepared in analogy to G. Dyker et al., Angewandte Chemie, 105(12), 1805 from methoxyacenaphth[1,2-a]acenaphthylene derivatives and iodobenzene, wherein the first step shown below in scheme 3 is followed by the sequence of steps 3-5 described above in scheme 1.

Scheme 3

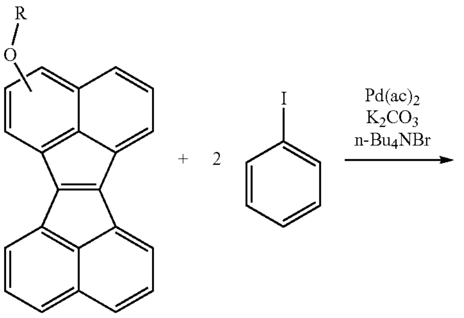

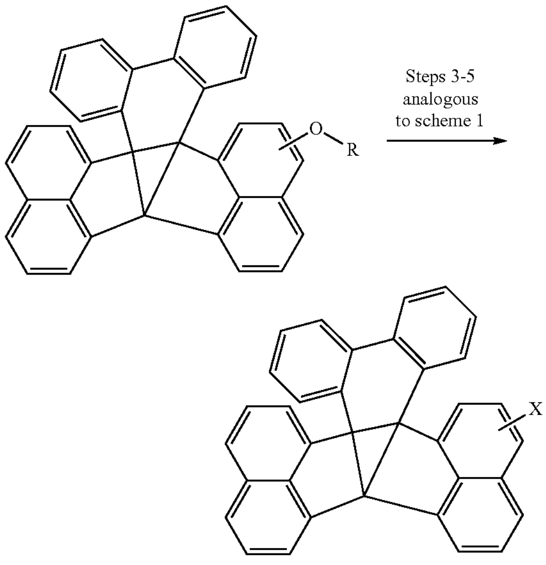

X: —— $N(Ar)_2$ or aryl or heteroaryl, where Ar = aryl or heteroaryl R: any organic radical, preferably aryl or alkyl, more preferably alkyl The compounds may bear a substituent at any of the positions shown as unsubstituted.

Compounds of the formula (IV) can be prepared from alkoxy-substituted 1,2-acenaphthenes and substituted or unsubstituted 1-naphthylmagnesium bromides and acid-catalyzed rearrangement of the intermediate diols, wherein step 1 shown below in scheme 4 is followed by the sequence of steps 3-5 described above in scheme 1.

Scheme 4

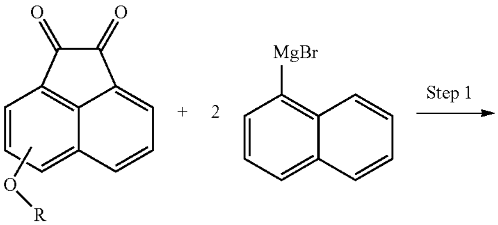

-continued

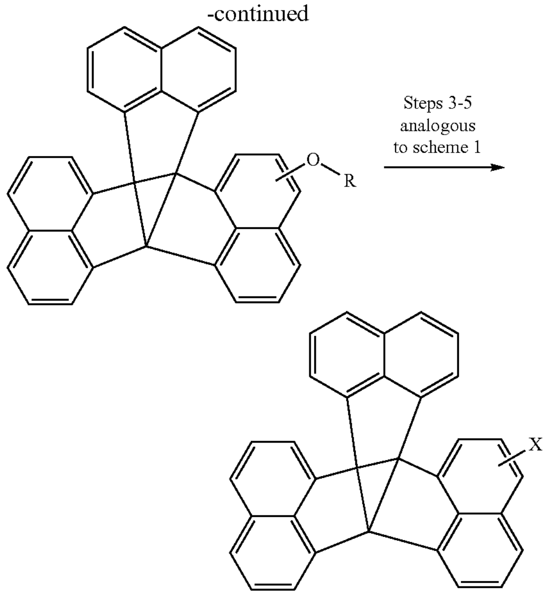

X: —— $N(Ar)_2$ or aryl or heteroaryl, where Ar = aryl or heteroaryl R: any organic radical, preferably aryl or alkyl, more preferably alkyl The compounds may bear a substituent at any of the positions shown as unsubstituted.

The syntheses shown above are examples by which the person skilled in the art is not bound. The person skilled in the art is able, within the scope of his common art knowledge, to conduct modified syntheses in order to arrive at the compounds of the formulae (I) to (IV).

The present application provides a process for preparing a compound of the invention, characterized in that the alkoxy-substituted base skeleton is first prepared and is then converted in a further step to a reactive compound, preferably to a triflate derivative, which is converted in a further step by transition metal-catalyzed coupling reaction, preferably Hartwig-Buchwald, Suzuki, Stille, or Negishi coupling, to the compound of the invention. Preference is given here to Hartwig-Buchwald coupling for preparation of a compound of the invention that bears an amino group directly bonded to the base skeleton, and to Suzuki coupling for preparation of a compound of the invention that bears an aryl or heteroaryl group directly bonded to the base skeleton.

For preparation of a compound of the formula (I), for synthesis of the abovementioned alkoxy-substituted base skeleton, a biphenyl derivative that bears both alkoxy group and a halogen atom, preferably bromine, as substituents is used. This biphenyl derivative is first metalated, preferably by lithium organyls or magnesium, and the metalated derivative is then added onto a spiro[9H-fluorene-9,9'(10'H)-phenanthrene]-10'-one derivative, which is followed by a cyclization of the tertiary alcohol and rearrangement in which the end product formed is the abovementioned alkoxy-substituted base skeleton of the formula (I).

For preparation of a compound of the formula (II), for synthesis of the abovementioned alkoxy-substituted base skeleton, a naphthyl derivative that bears both alkoxy group and a halogen atom, preferably bromine, as substituents is used. This naphthyl derivative is first metalated, preferably by lithium organyls or magnesium, and the metalated derivative is then added onto a spiro[9H-fluorene-9,9'(10'H)-phenanthrene]-10'-one derivative, which is followed by a cyclization of the tertiary alcohol and rearrangement in which the end product formed is the abovementioned alkoxy-substituted base skeleton of the formula (I).

For preparation of a compound of the formula (III), for synthesis of the abovementioned alkoxy-substituted base skeleton, an iodobenzene derivative is used. This iodobenzene derivative is reacted under Pd catalysis with a methoxyacenaphth[1,2-a]acenaphthylene derivative, in a sequence composed of Heck reaction and Pd-catalyzed C—C coupling and Pd-catalyzed C—C coupling with C—H activation. The end product formed is the abovementioned alkoxy-substituted base skeleton of the formula (III).

For preparation of a compound of the formula (IV), for synthesis of the abovementioned alkoxy-substituted base skeleton, a 1-naphthylmagnesium bromide derivative is reacted with an alkoxy-substituted 1,2-acenaphthene, with acid-catalyzed rearrangement of the intermediate diol formed to give the alkoxy- or halogen-substituted base skeleton of the formula (IV).

The above-described compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), (II), (III) or (IV), wherein the bond(s) to the polymer, oligomer or dendrimer may be localized at any desired positions substituted by $R^1$, $R^2$ or $R^5$ in the formulae mentioned. According to the linkage of the compound of formula (I), (II), (III) or (IV), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of the abovementioned formulae may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of the abovementioned formulae to be joined via a trivalent or higher-valency group, for example via a trivalent or higher-valency aromatic or heteroaromatic group, to give a branched or dendritic oligomer or polymer.

For the repeat units of formula (I), (II), (III) or (IV) in oligomers, dendrimers and polymers, the same preferences apply as described above for compounds of the abovementioned formulae.

For preparation of the oligomers or polymers, the monomers of the invention are homopolymerized or copolymerized with further monomers. Suitable and preferred comonomers are selected from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers and oligomers of the invention are generally prepared by polymerization of one or more monomer types, of which at least one monomer leads to repeat units of the formula (I), (II), (III) or (IV) in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I), (II), (III) or (IV) and at least one solvent, preferably an organic solvent. The way in which such solutions can be prepared is known to those skilled in the art and is described, for example, in WO 2002/072714, WO 2003/019694 and the literature cited therein.

The compounds of the invention are suitable for use in electronic devices, especially in organic electroluminescent devices (OLEDs). Depending on the substitution, the compounds are used in different functions and layers.

The invention therefore further provides for the use of the compound of formula (I), (II), (III) or (IV) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of the invention. This electronic device is preferably selected from the abovementioned devices.

It is more preferably an organic electroluminescent device (OLED) comprising anode, cathode and at least one emitting layer, characterized in that at least one organic layer, which may be an emitting layer, a hole transport layer or another layer, comprises at least one compound of the invention.

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device comprising the compound of the formula (I), (II), (III) or (IV) is preferably as follows:

anode-hole injection layer-hole transport layer-optionally further hole transport layer(s)-optionally electron blocker layer-emitting layer-optionally hole blocker layer-electron transport layer-electron injection layer-cathode. It is additionally possible for further layers to be present in the OLED.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission (for the basic construction see, for example, WO 2005/011013). The compounds of the invention are preferably present here in a hole transport layer, hole injection layer, electron blocker layer, emitting layer, hole-blocking layer and/or electron-transporting layer, more preferably in a hole transport layer, an emitting layer as matrix material, in a hole blocker layer and/or in an electron transport layer.

It is preferable in accordance with the invention when the compound of the invention is used in an electronic device comprising one or more phosphorescent emitting compounds. In this case, the compound may be present in different layers, preferably in a hole transport layer, an electron blocker layer, a hole injection layer, an emitting layer, a hole blocker layer and/or an electron transport layer. More preferably, it is present in an emitting layer in combination with a phosphorescent emitting compound.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

Examples of the above-described emitting compounds can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of the invention in organic electroluminescent devices. Further examples are listed in the following table:

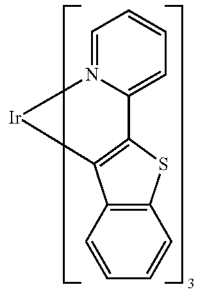

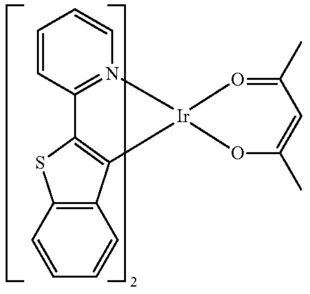

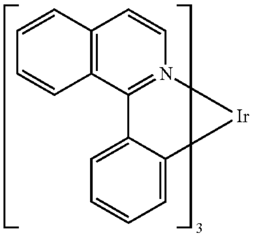

-continued
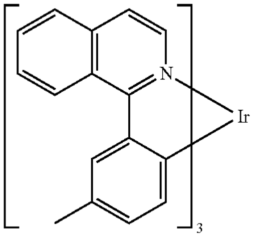
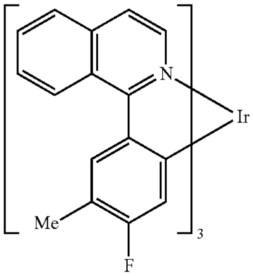
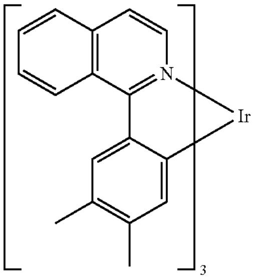
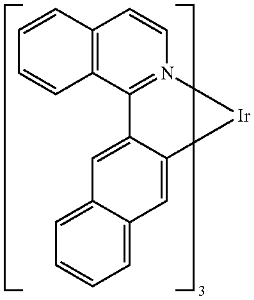
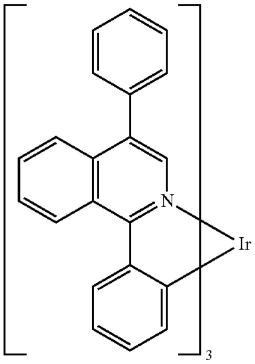
-continued
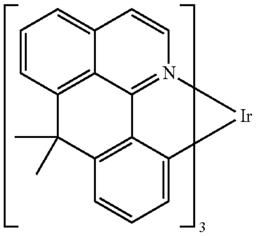
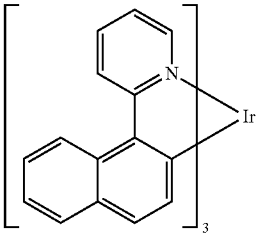
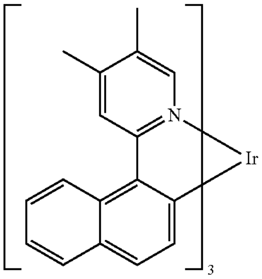
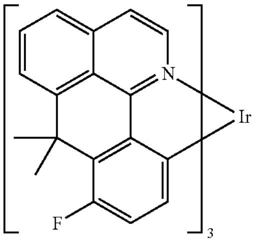
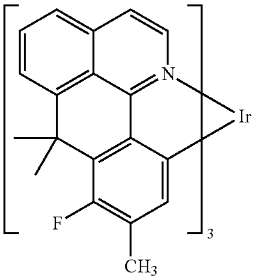
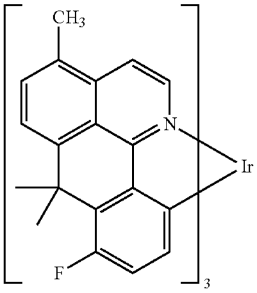

-continued
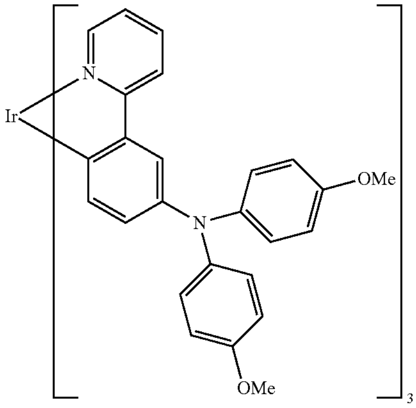
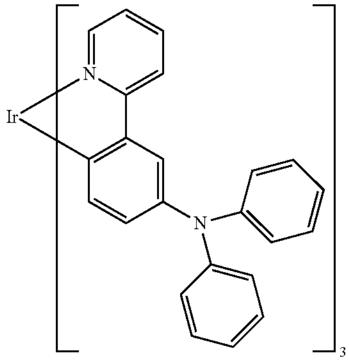
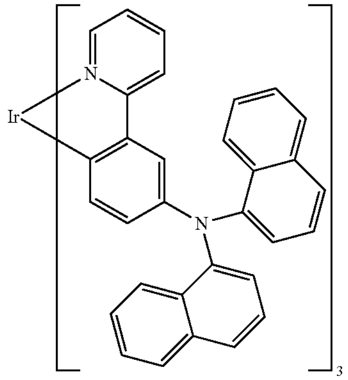
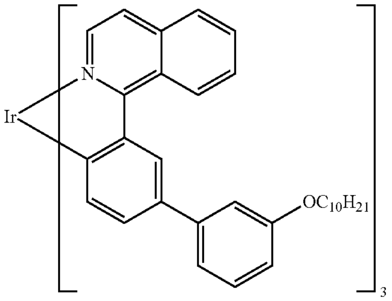
-continued
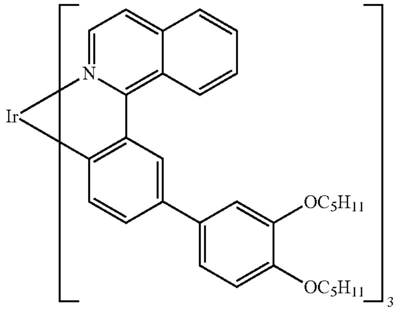
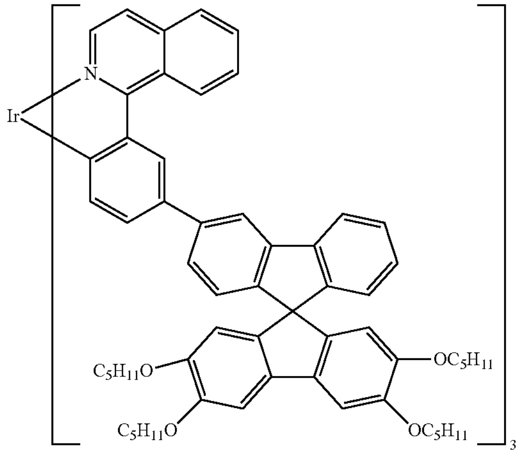
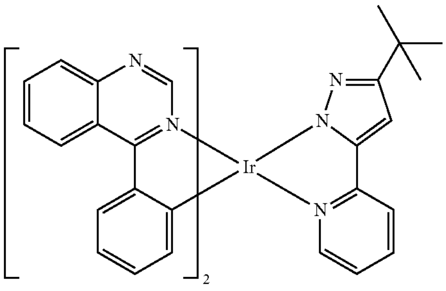
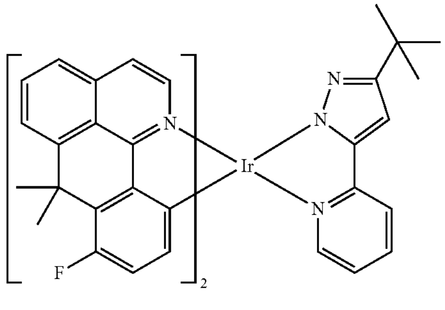

-continued
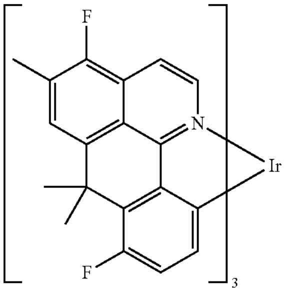
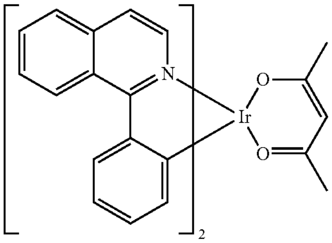
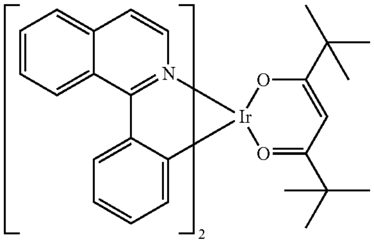
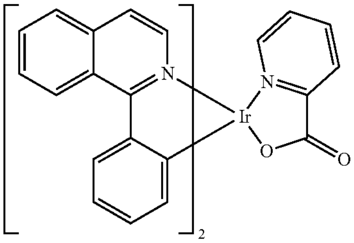
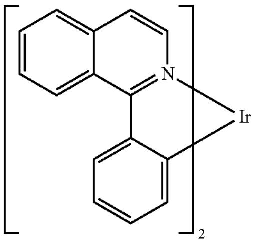
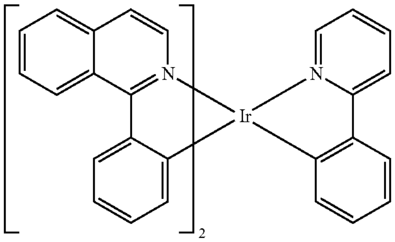
-continued
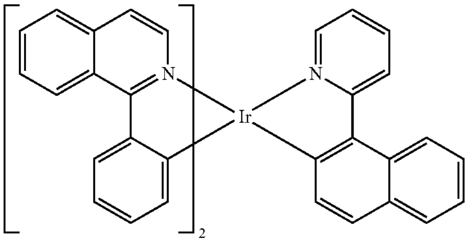
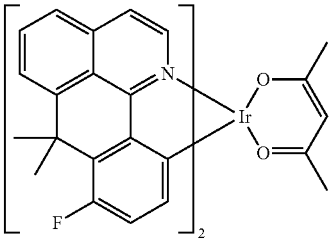
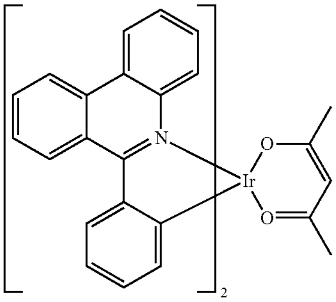
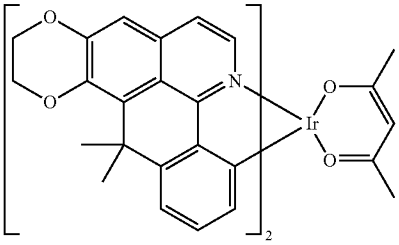
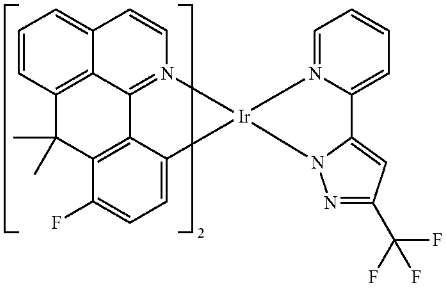
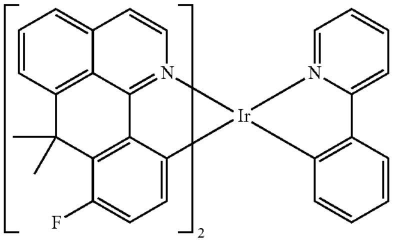

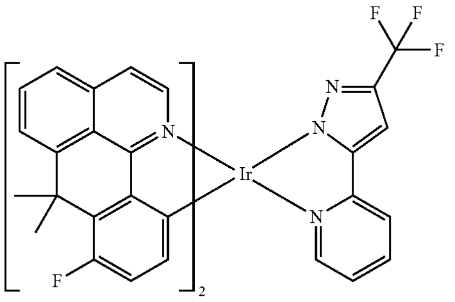
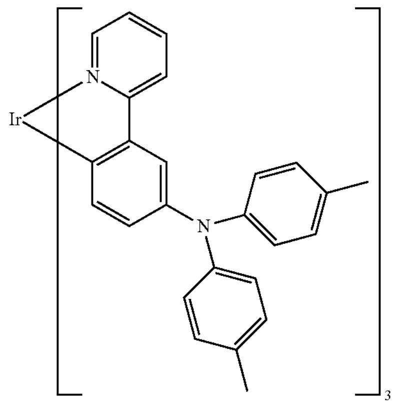
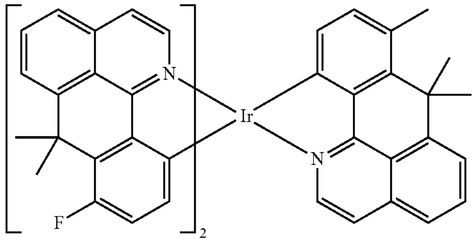
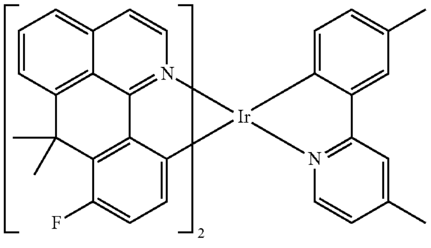
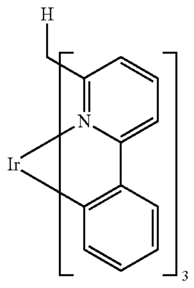
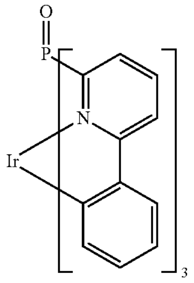
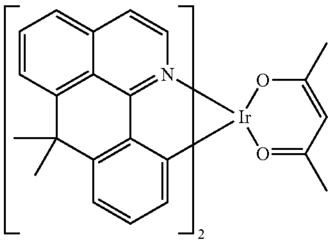
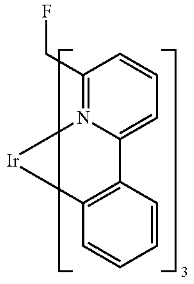
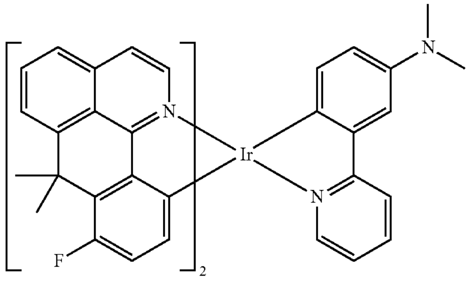
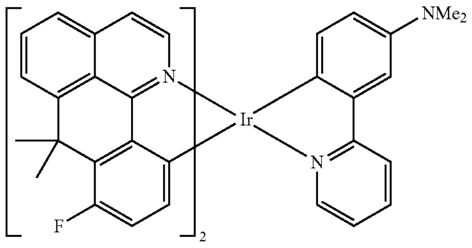
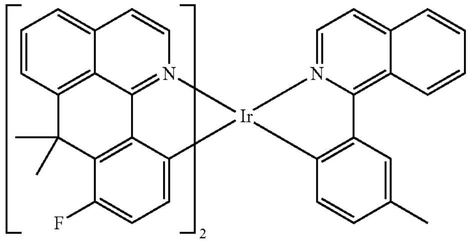

-continued
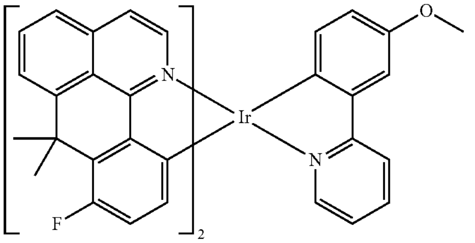
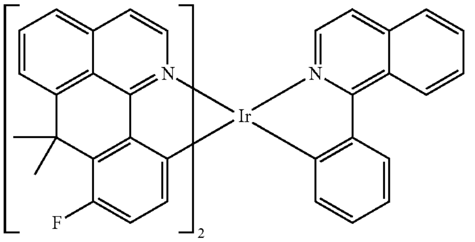
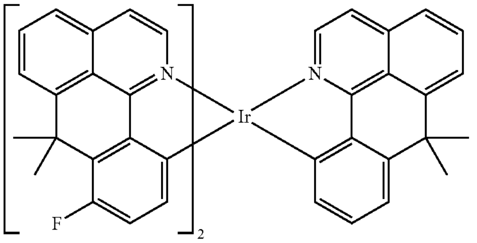
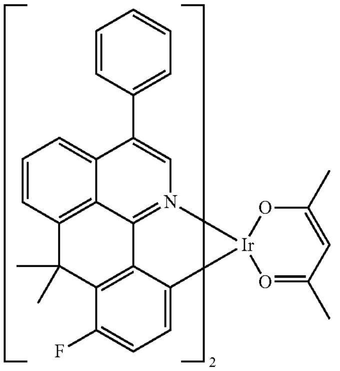
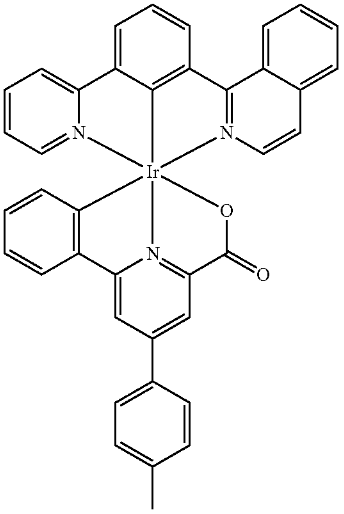
-continued
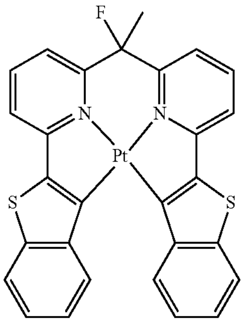
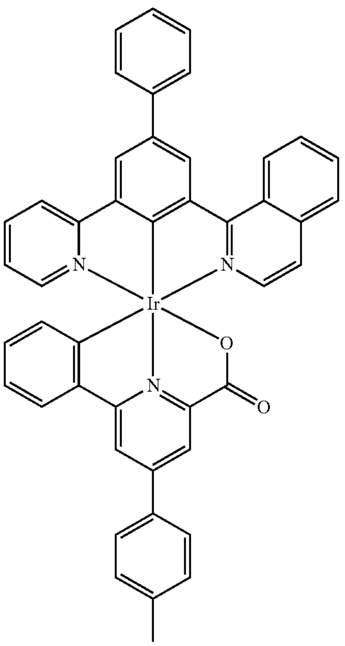
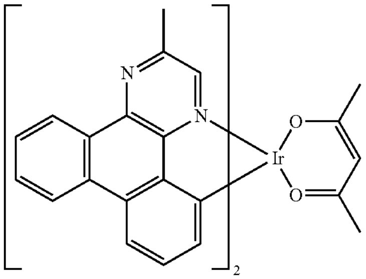
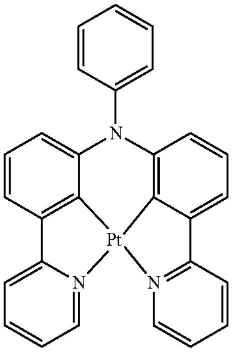

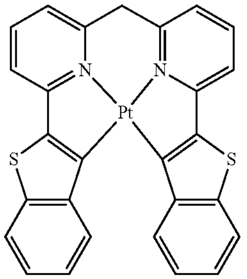
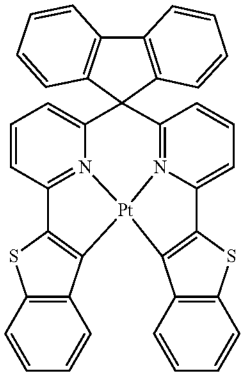
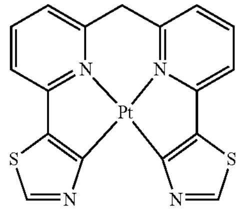
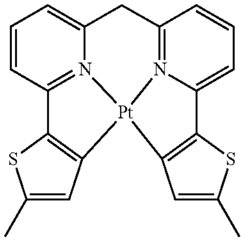
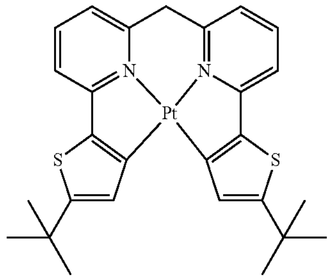
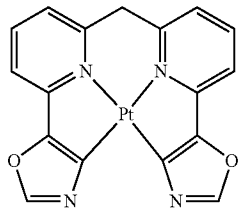
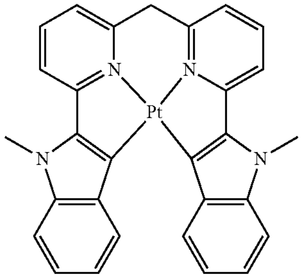
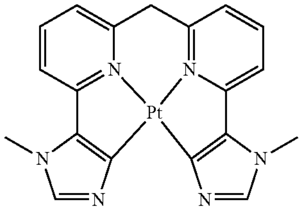
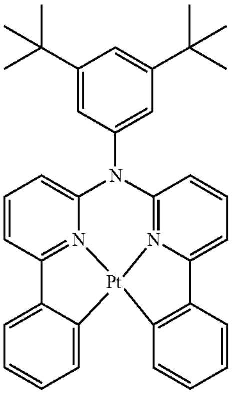
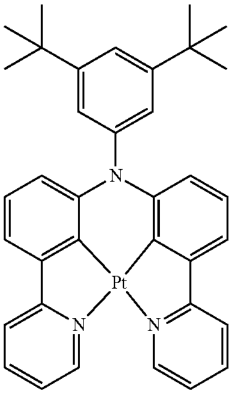

-continued
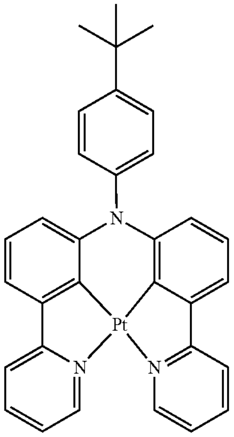
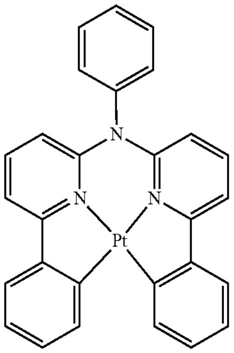
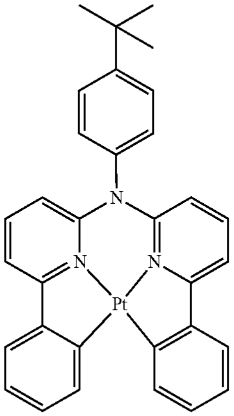
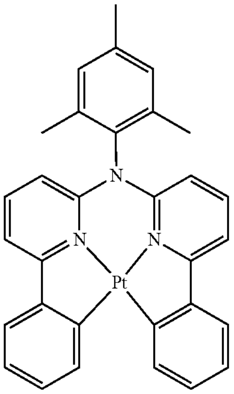
-continued
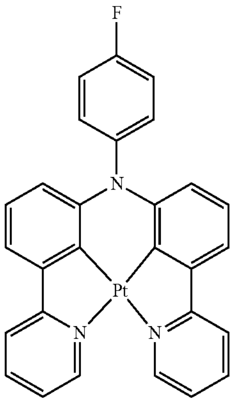
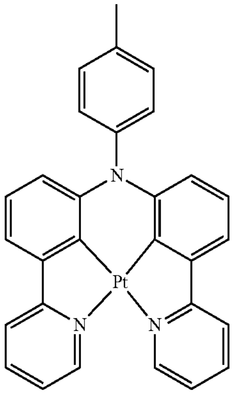
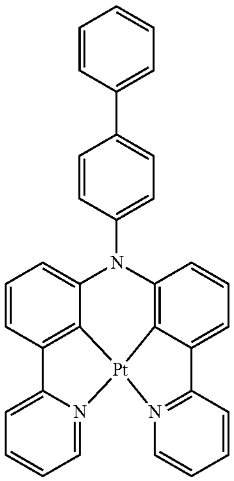

-continued
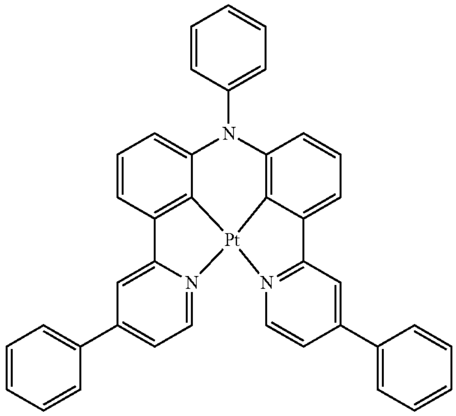
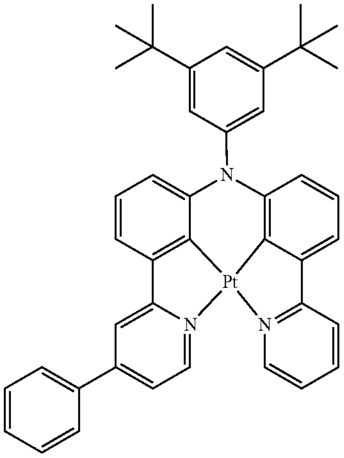
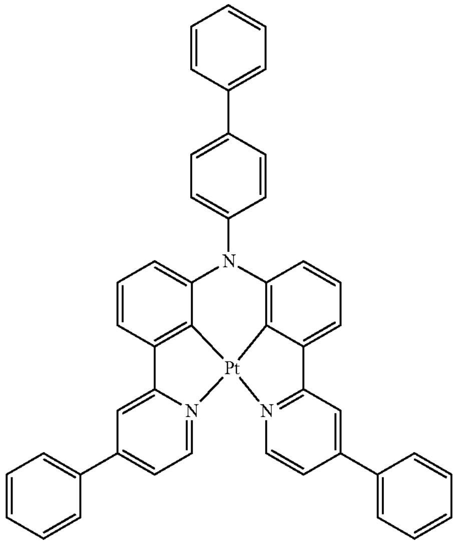
-continued
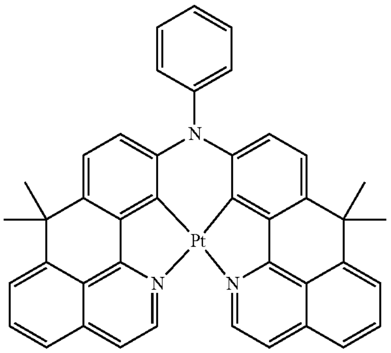
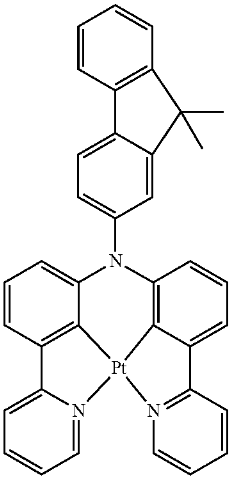
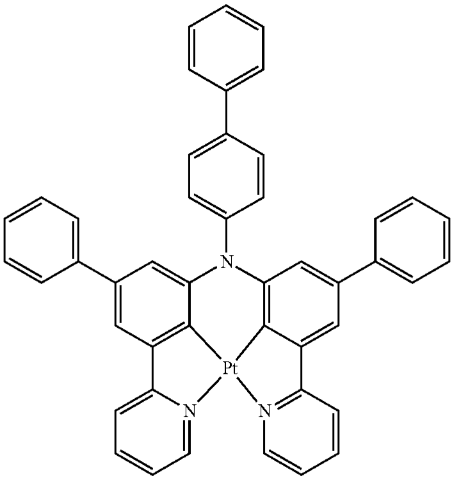

-continued
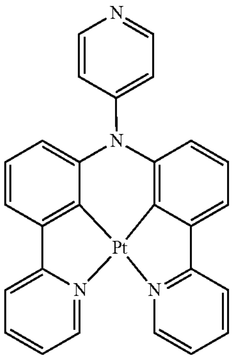
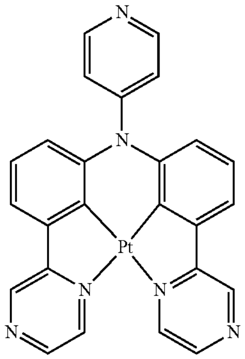
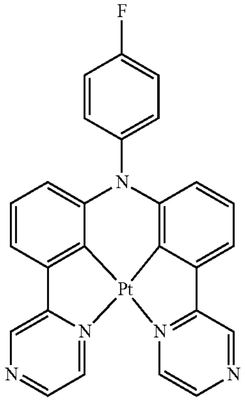
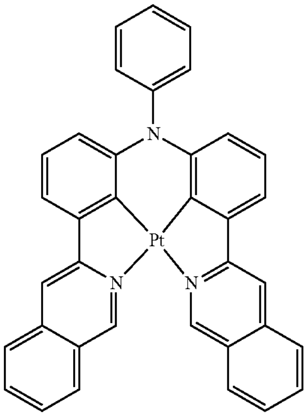
-continued
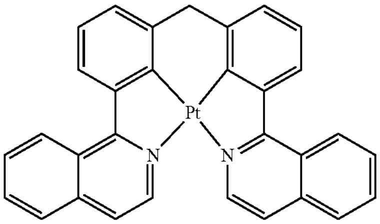
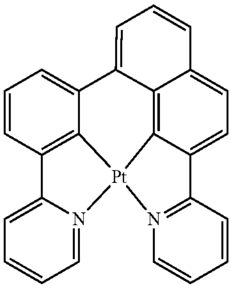
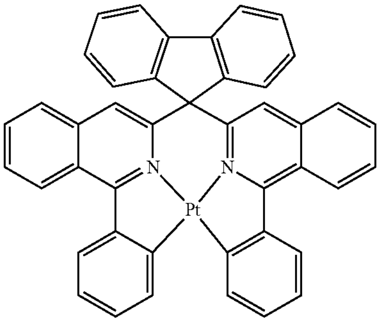
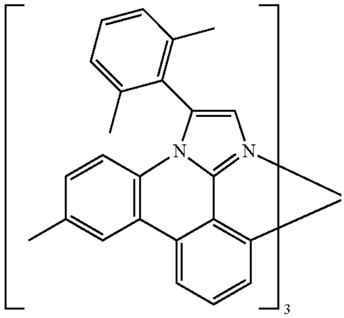
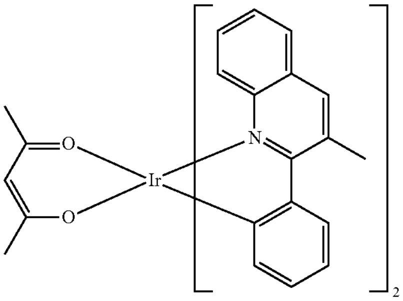

-continued
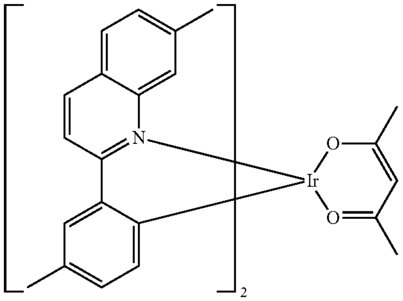
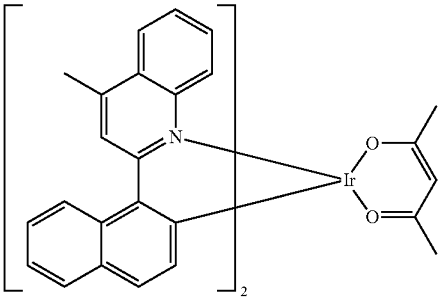
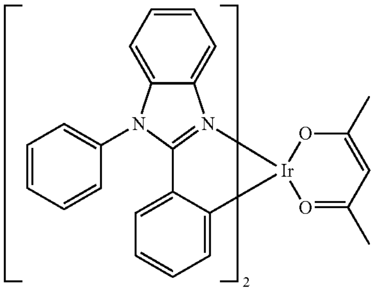
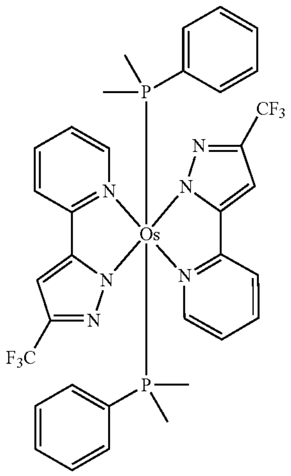
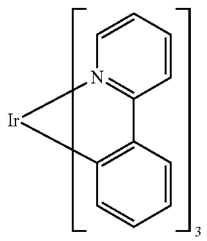
-continued
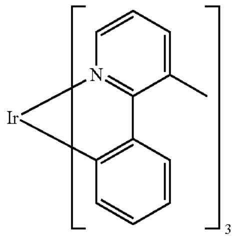
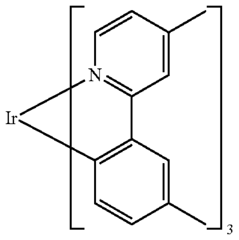
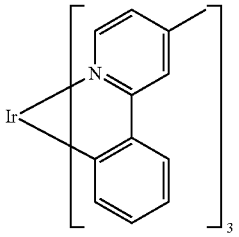
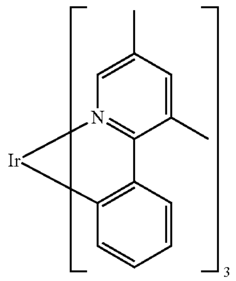
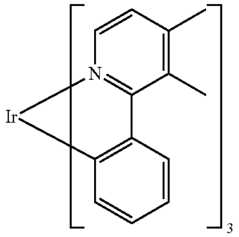
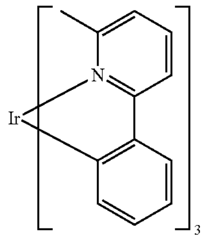

-continued
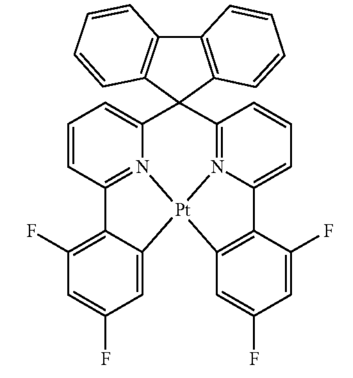
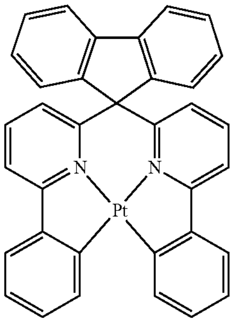
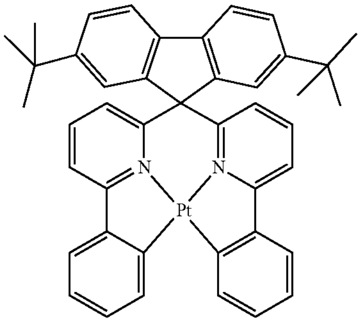
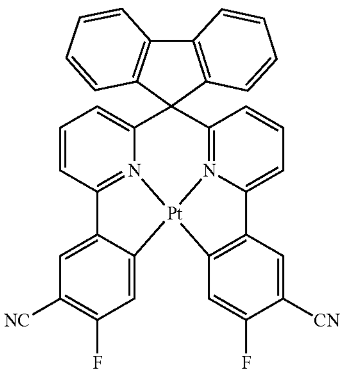
-continued
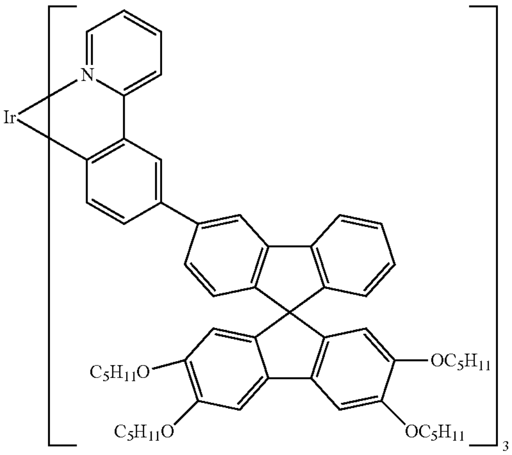
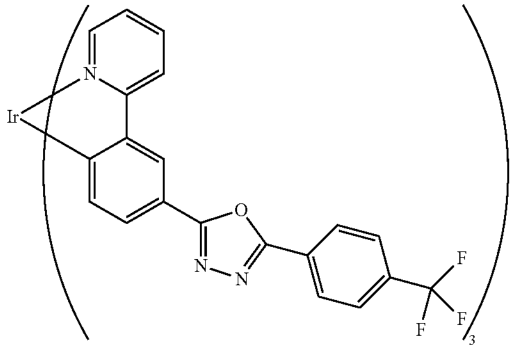
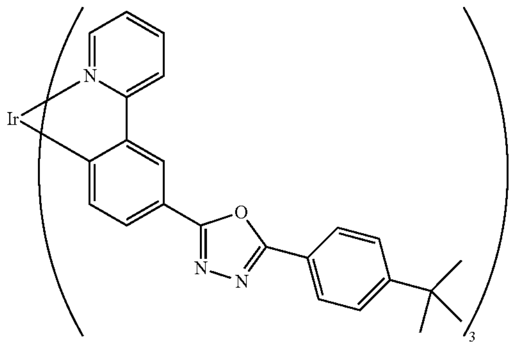
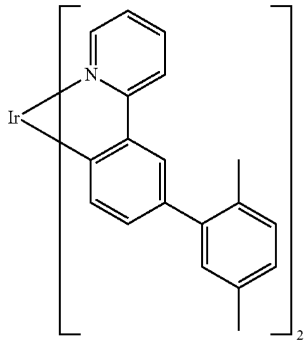

-continued
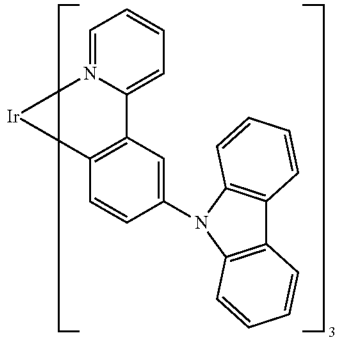
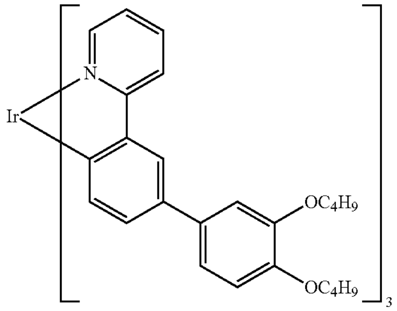
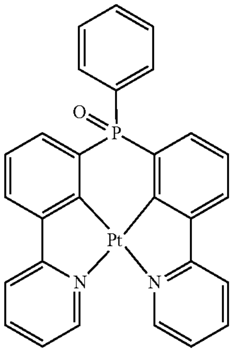
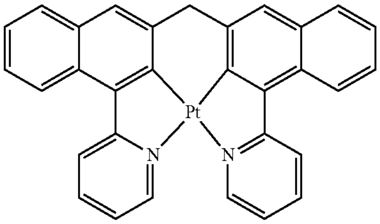
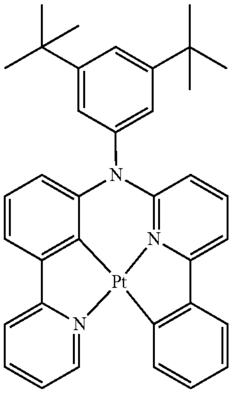
-continued
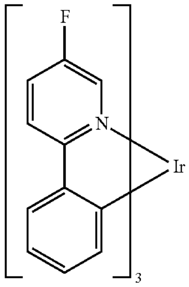
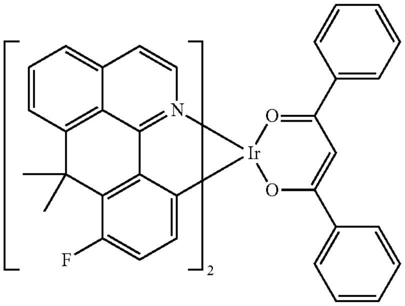
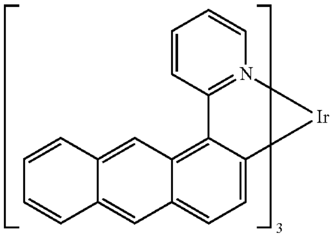
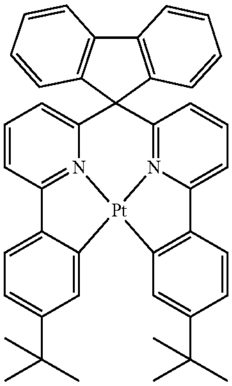
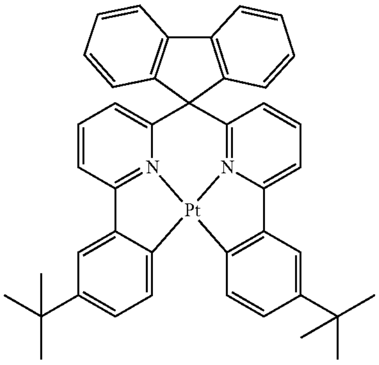

-continued
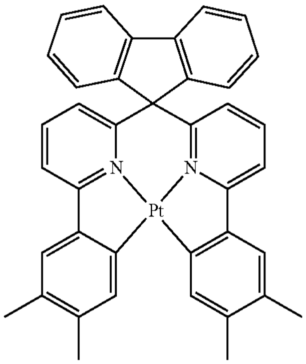
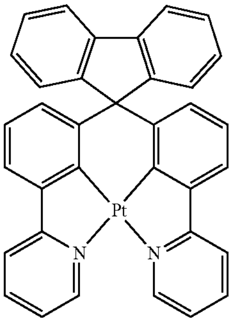
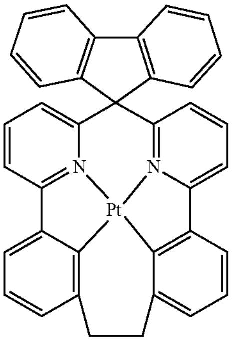
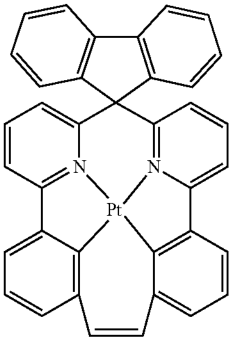
-continued
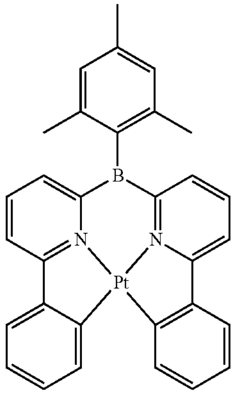
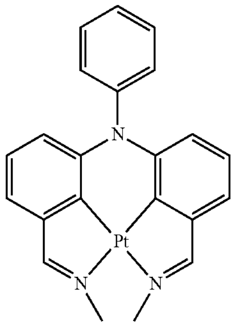
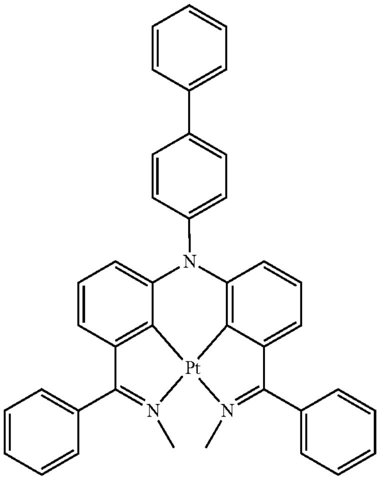
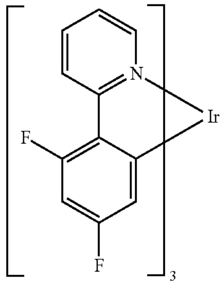

-continued
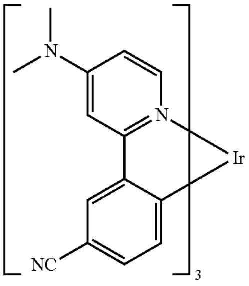
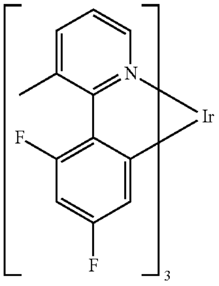
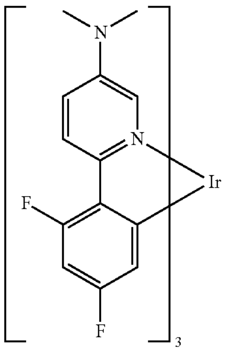
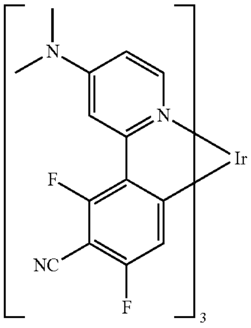
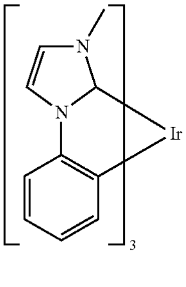
-continued
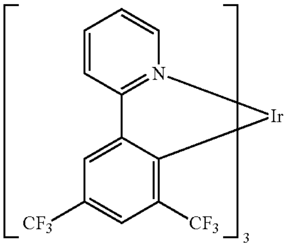
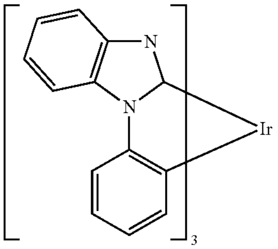
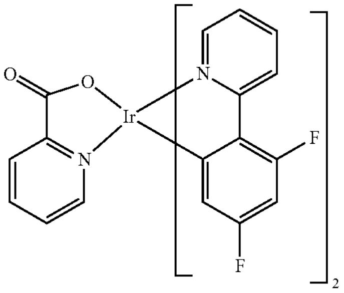
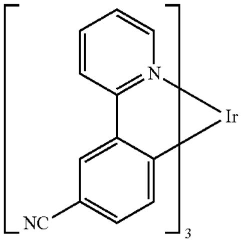
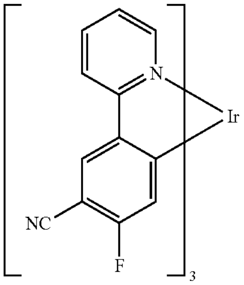
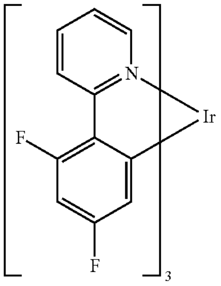

-continued
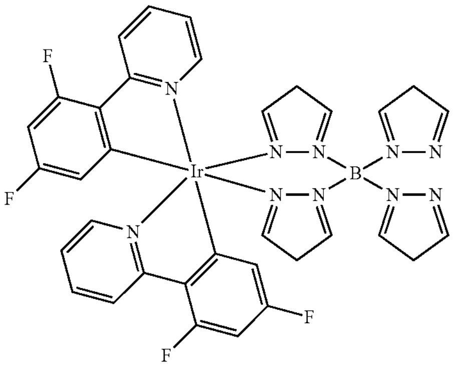
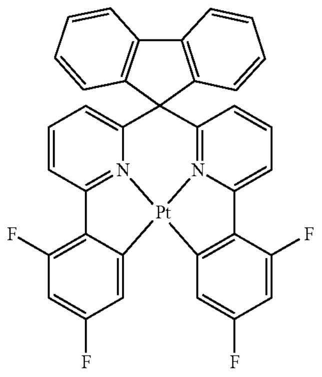
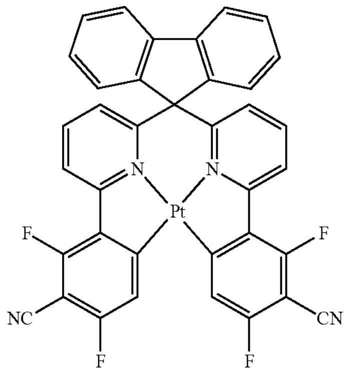
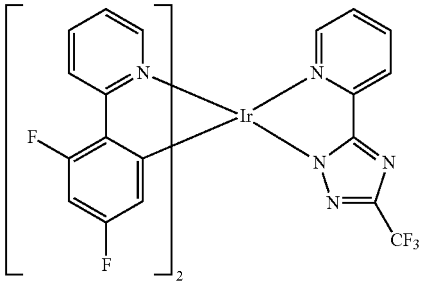
-continued
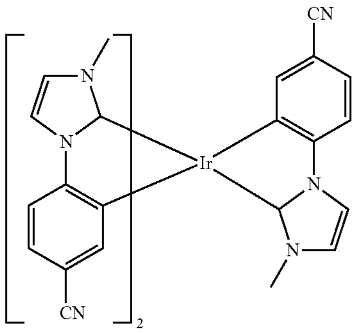
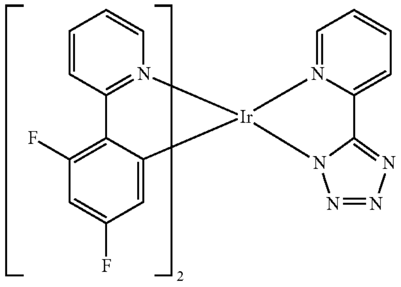
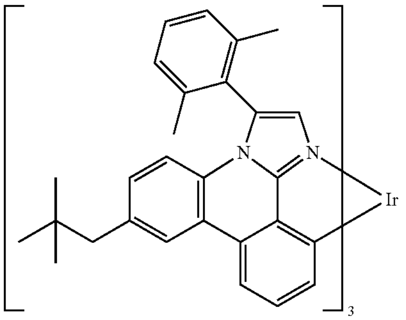
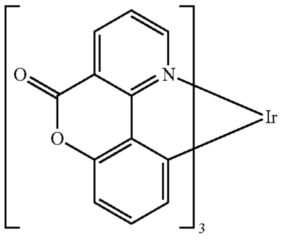
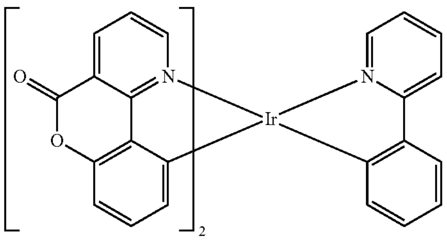

-continued
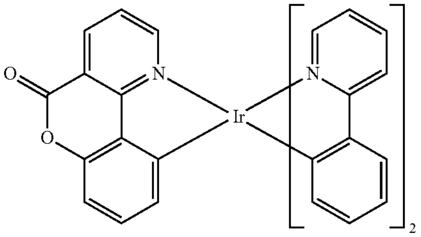
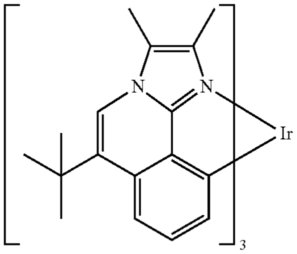
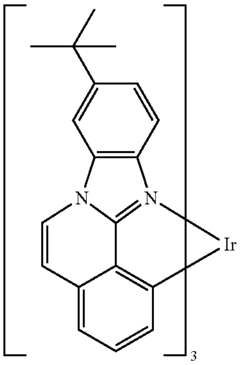
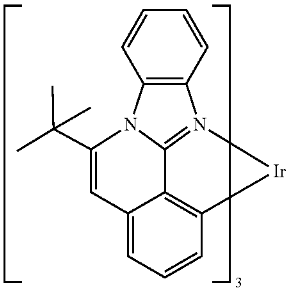
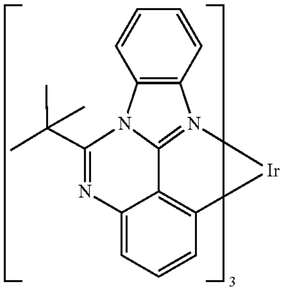
-continued
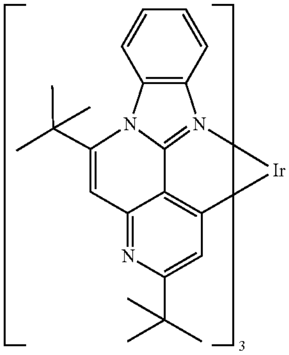
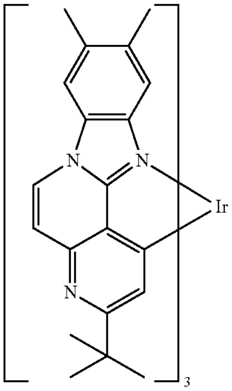
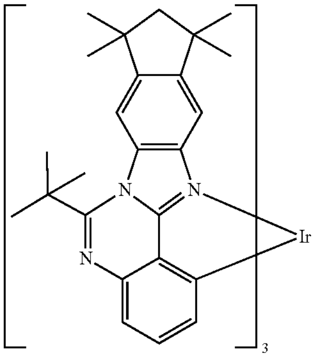
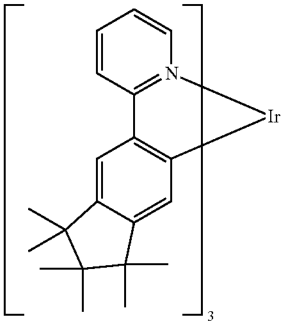

-continued
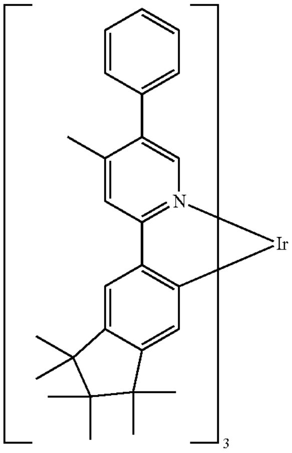
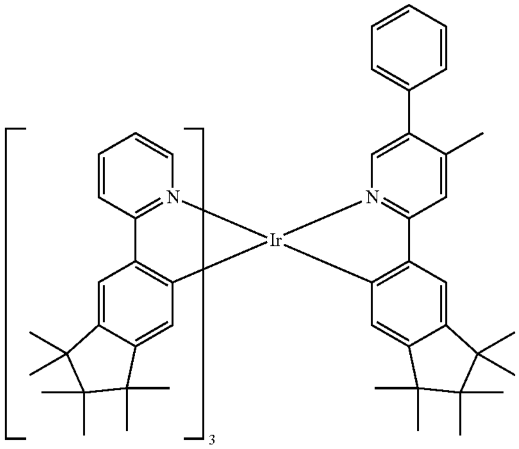
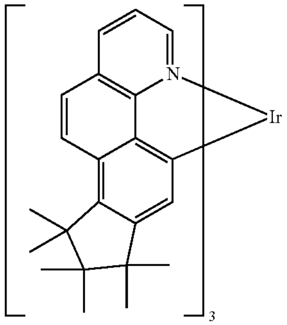
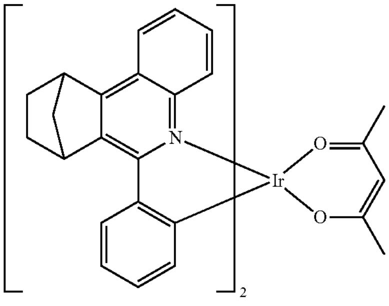
-continued
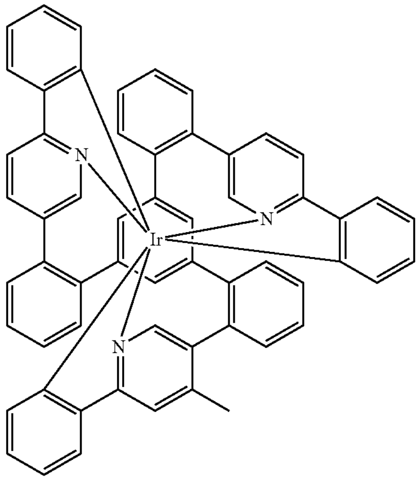
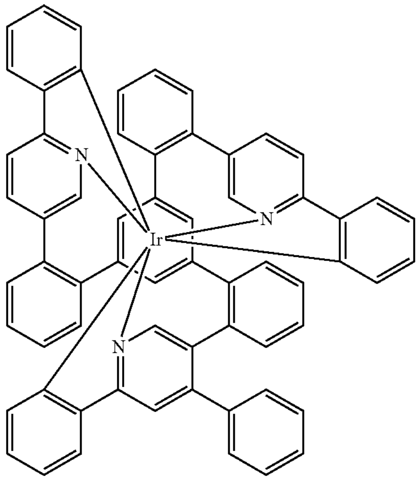
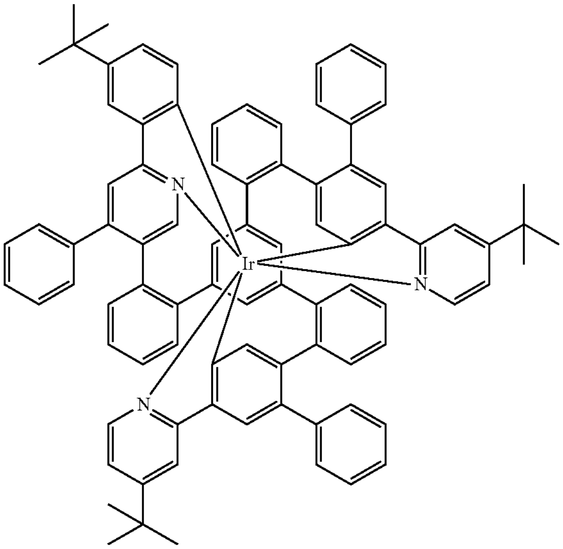

-continued

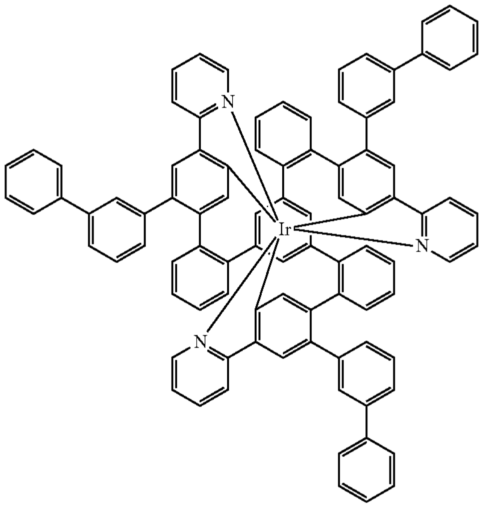

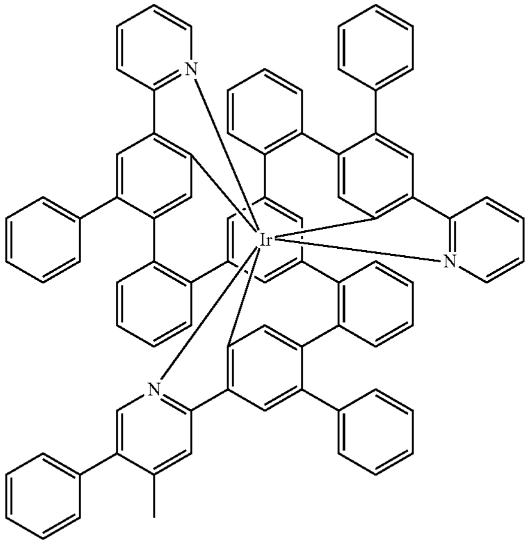

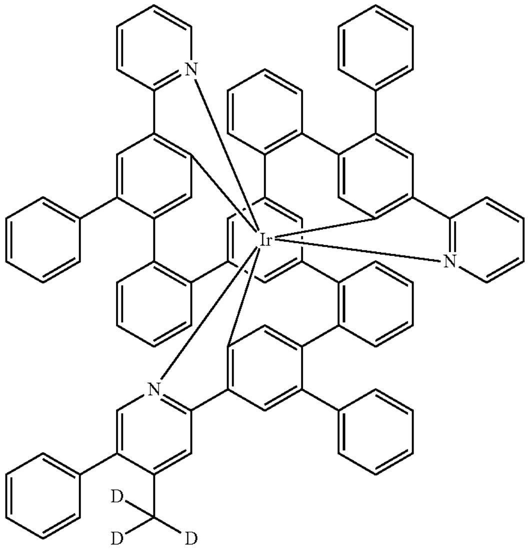

In a preferred embodiment of the invention, the compounds of the invention are used as hole-transporting material. Especially suitable for this purpose are compounds of the formulae (I) to (IV) containing exactly one group of the formula (A). In that case, the compounds are preferably present in a hole transport layer, an electron blocker layer or a hole injection layer.

A hole transport layer according to the present application is a layer having a hole-transporting function between the anode and emitting layer.

Hole injection layers and electron blocker layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocker layer, in the case of a plurality of hole transport layers between the anode and emitting layer, is that hole transport layer which directly adjoins the emitting layer on the anode side. Preferably, the OLED of the invention comprises two, three or four hole-transporting layers between the anode and emitting layer, at least one of which preferably contains a compound of formula (I), (II), (III) or (IV), and more preferably exactly one or two contain a compound of formula (I), (II), (III) or (IV).

If the compound of the invention is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer comprising the compound of the invention then additionally contains one or more p-dopants. p-Dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred p-dopants are quinodimethane compounds, azaindenofluorenediones, azaphenalenes, azatriphenylenes, $I_2$, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$.

The p-dopants are preferably in substantially homogeneous distribution in the p-doped layers. This can be achieved, for example, by coevaporation of the p-dopant and the hole transport material matrix.

Preferred p-dopants are especially the following compounds:
(D-1)
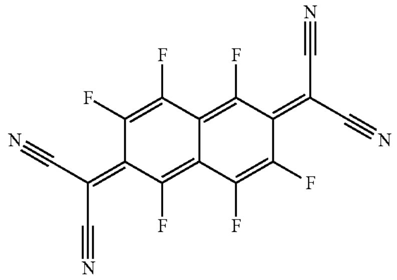
(D-2)
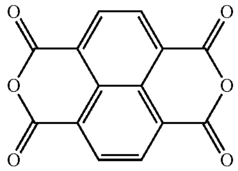
(D-3)
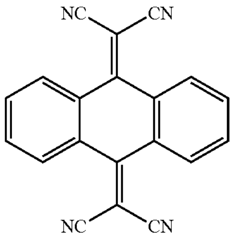
(D-4)
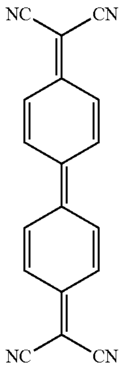
(D-5)
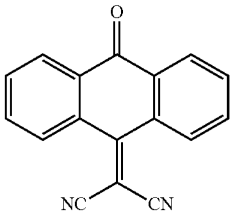
(D-6)
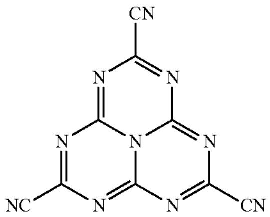
-continued
(D-7)
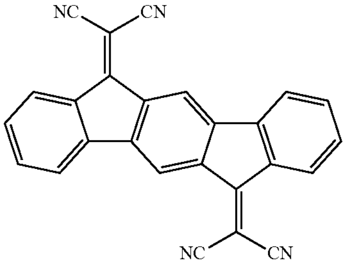
(D-8)
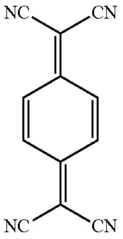
(D-9)
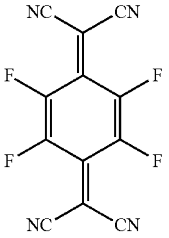
(D-10)
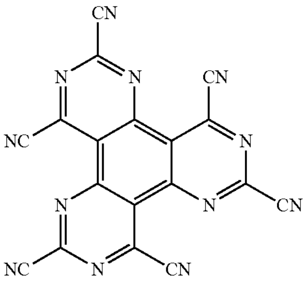
(D-11)
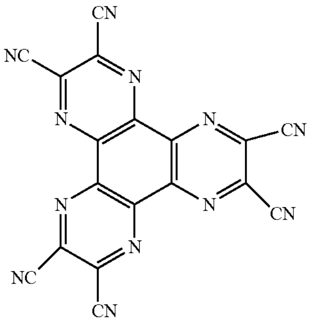

-continued (D-12)

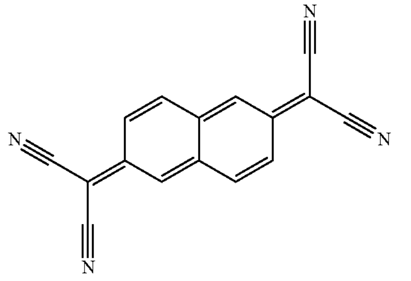

(D-13)

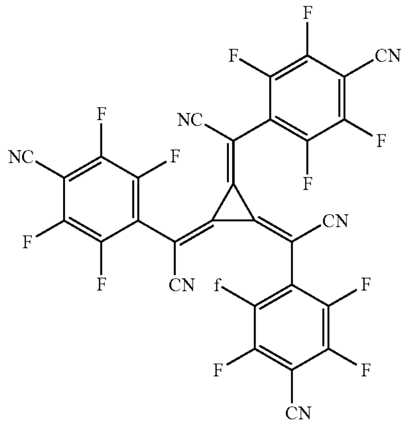

In a further preferred embodiment of the invention, the compound of the invention is used as hole transport material in combination with a hexaazatriphenylene derivative as described in US 2007/0092755. Particular preference is given here to using the hexaazatriphenylene derivative in a separate layer. This separate layer is preferably arranged directly adjoining the anode and between the anode and the closest hole transport layer to the anode.

In a preferred embodiment of the present invention, the compound of the invention is used in an emitting layer as matrix material in combination with one or more phosphorescent emitting compounds. Especially suitable for this purpose are compounds of the formula (I)-(IV) that have exactly one group of the formula (H), especially compounds of the abovementioned formulae that have exactly one group of the formula (H) that contains one or more carbazole groups. Preferably, at least one $L^1$ group is carbazole, and/or the $Ar^2$ group is carbazole.

The proportion of the matrix material in the emitting layer in this case is between 50.0% and 99.9% by volume, preferably between 80.0% and 99.5% by volume, and more preferably between 85.0% and 97.0% by volume.

Correspondingly, the proportion of the emitting compound is between 0.1% and 50.0% by volume, preferably between 0.5% and 20.0% by volume, and more preferably between 3.0% and 15.0% by volume.

An emitting layer of an organic electroluminescent device may also contain systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compounds of the invention are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The compound of the invention is preferably the matrix material having hole-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the compounds of the invention as matrix components of a mixed matrix system are selected from the preferred matrix materials specified below for phosphorescent emitting compounds or the preferred matrix materials for fluorescent emitting compounds, according to what type of emitting compound is used in the mixed matrix system.

Preferred phosphorescent emitting compounds for use in mixed matrix systems are the same as detailed further up as generally preferred phosphorescent emitter materials.

In a further preferred embodiment, the compounds of the invention are used in one or more layers on the electron transport side, preferably in a hole blocker layer and/or an electron transport layer. Especially suitable for this purpose are compounds of the formula (I)-(IV) that have exactly one group of the formula (H), especially a group of the formula (H) in which at least one $L^1$ group or the $Ar^2$ group is selected from triazine and pyrimidine. In the case of use in an electron transport layer, it is preferable that they are used in combination with a metal complex, preferably a metal quinolinate, more preferably a lithium quinolinate.

Preferred embodiments of the different functional materials in the electronic device are listed hereinafter.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred emitting compounds are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluoreneamines disclosed in WO 2014/037077, the benzofluoreneamines disclosed in WO 2014/106522, the extended benzoindenofluorenes disclosed in WO 2014/111269 and in the as yet unpublished application EP 15182993.4, the phenoxazines disclosed in the as yet unpublished applications EP 15181178.3 and EP 15181177.5, and the fluorene derivatives bonded to furan units or to thiophene units that are disclosed in WO 2016/150544.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, the pyrene compounds disclosed in EP 1749809, EP 1905754 and US 2012/0187826, the benzanthracenylanthracene compounds disclosed in WO 2015/158409, the indenobenzofurans disclosed in the as yet unpublished application EP 15180777.3, and the phenanthrylanthracenes disclosed in the as yet unpublished application EP 15182962.9.

Preferred matrix materials for phosphorescent emitting compounds are, as well as the compounds of the invention, aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge transport materials as usable in the hole injection or hole transport layer or electron blocker layer or in the electron transport layer of the electronic device of the invention are, as well as the compounds of the invention, for example, the compounds disclosed in Y. Shirota et al., Chem. Rev. 2007, 107(4), 953-1010, or other materials as used in these layers according to the prior art.

Preferably, the inventive OLED comprises two or more different hole-transporting layers. The compound of the invention may be used here in one or in more than one or in all the hole-transporting layers. In a preferred embodiment, the compound of the invention is used in exactly one or exactly two hole-transporting layers, and other compounds, preferably aromatic amine compounds, are used in the further hole-transporting layers present. Further compounds which are used alongside the compounds of the invention, preferably in hole-transporting layers of the OLEDs of the invention, are especially indenofluoreneamine derivatives (for example according to WO 06/122630 or WO 06/100896), the amine derivatives disclosed in EP 1661888, hexaazatriphenylene derivatives (for example according to WO 01/049806), amine derivatives with fused aromatics (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or WO 2013/120577), fluoreneamines (for example according to WO 2014/015937, WO 2014/015938, WO 2014/015935 and WO 2015/082056), spirodibenzopyranamines (for example according to WO 2013/083216), dihydroacridine derivatives (for example according to WO 2012/150001), spirodibenzofurans and spirodibenzothiophenes, for example according to WO 2015/022051 and the as yet unpublished applications PCT/EP2015/002475 and PCT/EP2016/000084, phenanthrenediarylamines, for example according to WO 2015/131976, spirotribenzotropolones, for example according to the as yet unpublished application PCT/EP2015/002225, spirobifluorenes with meta-phenyldiamine groups, for example according to the as yet unpublished application PCT/EP2015/002112, spirobisacridines, for example according to WO 2015/158411, xanthenediarylamines, for example according to WO 2014/072017, and 9,10-dihydroanthracene spiro compounds with diarylamino groups according to WO 2015/086108.

Materials used for the electron transport layer may be any materials as used according to the prior art as electron transport materials in the electron transport layer. Especially suitable are aluminum complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects of water and air.

In a preferred embodiment, the electronic device is characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapor phase deposition) method or with the aid of a carrier gas sublimation. In this case, the materials are applied at a pressure between $10^{-6}$ mbar and 1 bar. A special case of this method is the OVJP (organic vapor jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I), (II), (III) or (IV) are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of the invention can be used in displays, as light sources in lighting applications and as light sources in medical and/or cosmetic applications (e.g. light therapy).

EXAMPLES

A) Synthesis Examples

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

Hereinafter, the [4.4.4]-propellanes, for the sake of clarity, are shown in the form of a Newman projection, as is also customary in the literature; see, for example, M. Kimura et al., Bull. Chem. Soc. Jpn., 2006, 79, 11, 1793.

A: Synthesis of the Synthons

Example S1

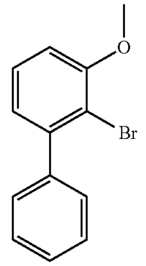

A mixture of 31.3 g (100 mmol) of 1-bromo-2-iodo-6-methoxybenzene [74128-84-0], 12.2 g (100 mmol) of benzeneboronic acid [98-80-6], g (300 mmol) of tripotassium phosphate, g (1 mmol) of tetrakis(triphenylphosphino)palladium(0), 200 ml of toluene, 80 ml of dioxane and 200 ml of water is heated under reflux for 16 h. After cooling, the aqueous phase is removed and the organic phase is washed three times with 200 ml each time of water and once with 200 ml of saturated sodium chloride solution, and then dried over magnesium sulfate. The desiccant is filtered off, the organic phases concentrated to dryness and the remaining oil is subjected to kugelrohr distillation under high vacuum, Yield: 16.1 g (61 mmol), 61%; purity: 97% by $^1$H NMR.

Example S10

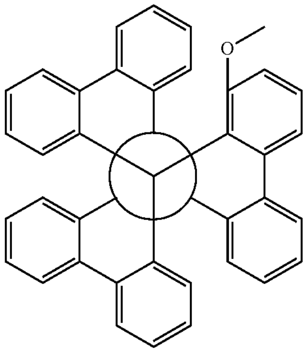 [SMILES: COc1cccc(-c2ccccc2C)c1C(c1ccccc1-c1ccccc1C)c1ccccc1-c1ccccc1C]

A solution, cooled to −78° C., of 26.3 g (100 mmol) of S1 in 1000 ml of diethyl ether and 40 ml (100 mmol) of n-butyllithium, 2.5 M in n-hexane, are used to prepare the corresponding lithium reagent. With good stirring, 34.4 g (100 mmol) of spiro[9H-fluorene-9,9'(10'H)-phenanthrene]-10'-one [1749-36-6] are added, the mixture is stirred at −70° C. for a further 30 minutes, then the mixture is allowed to warm up to room temperature and stirred for a further 24 h. The reaction is stopped by adding 200 ml of water and 200 ml of saturated ammonium chloride solution, and the organic phase is removed and dried over magnesium sulfate. The desiccant is filtered off, the solvent is removed under reduced pressure, and the residue is taken up in 500 ml of glacial acetic acid and homogenized while heating. Then 1 conc. sulfuric acid and 20 g of phosphorus pentoxide are added with good stirring, and the mixture is heated under reflux for 2 h. The mixture is left to cool to 80° C., then 400 ml of water are gradually added dropwise without further heating, and the precipitated solids are filtered off with suction, washed three times with 200 ml each time of water and once with 100 ml of methanol, and dried under reduced pressure. Yield: 38.9 g (76 mmol), 76%; purity: 97% by $^1$H NMR.

In an analogous manner, it is possible to prepare the following compounds:

| Ex. | Bromide | Product | Yield |
| --- | --- | --- | --- |
| S11 | 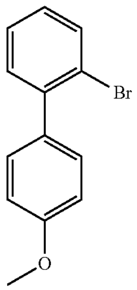 74447-76-0 | 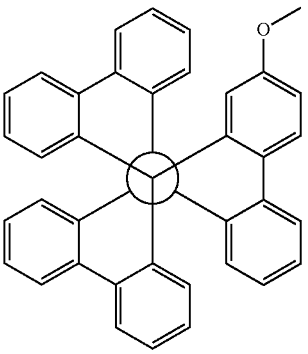 [SMILES: COc1ccc2c(c1)C13c4ccccc4-c4ccccc4C1(c1ccccc1-c1ccccc13)c1ccccc1-2] | 84% |
| S12 | 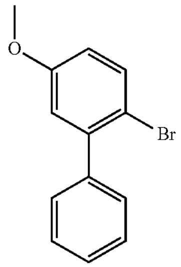 74447-77-1 | 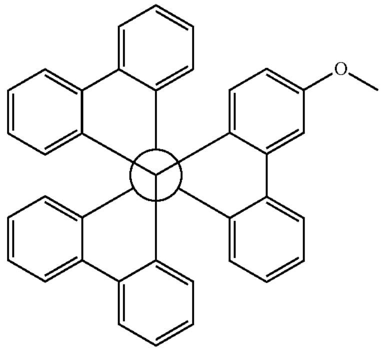 [SMILES: COc1ccc2c(c1)-c1ccccc1C13c4ccccc4-c4ccccc4C21c1ccccc1-c1ccccc13] | 80% |

-continued
| Ex. | Bromide | Product | Yield |
| --- | --- | --- | --- |
| S13 | 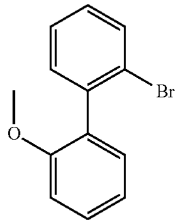<br>20837-12-1 | 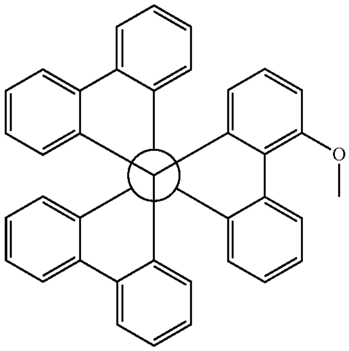 [SMILES: COc1cccc2c1-c1ccccc1C13c4ccccc4-c4ccccc4C21c1ccccc1-c1ccccc13] | 73% |
| S14 | 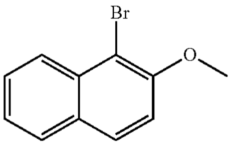<br>3401-47-6 | 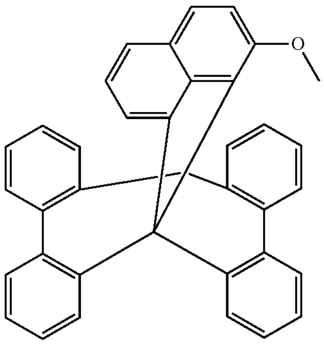 [SMILES: COc1ccc2cccc3c2c1C31c2ccccc2-c2ccccc2Cc2ccccc2-c2ccccc21] | 38% |
| S15 | 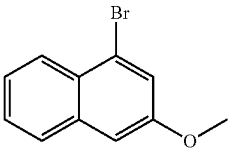<br>5111-34-2 | 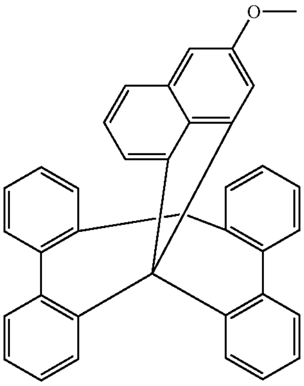 [SMILES: COc1cc2c3c(cccc3c1)C21c2ccccc2-c2ccccc2Cc2ccccc2-c2ccccc21] | 43% |
| S16 | 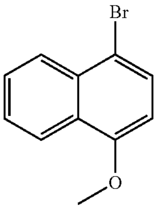<br>5467-58-3 | 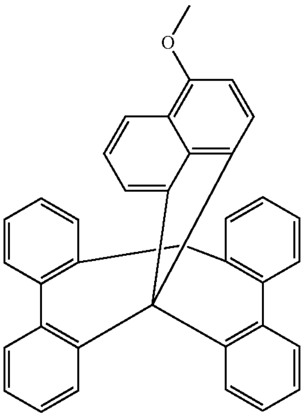 [SMILES: COc1ccc2c3c(cccc13)C21c2ccccc2-c2ccccc2Cc2ccccc2-c2ccccc21] | 45% |

-continued

| Ex. | Bromide | Product | Yield |
|---|---|---|---|
| S17 | 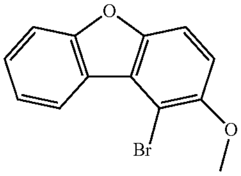<br>694453-47-9 | 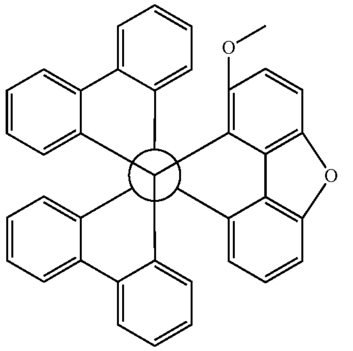 [SMILES: COc1ccc2oc3cccc4c3c2c1C12c3ccccc3-c3ccccc3C41c1ccccc1-c1ccccc12] | 48% |
| S18 | 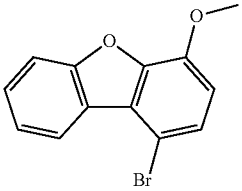<br>732301-39-2 | 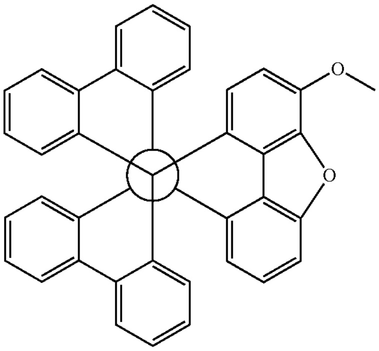 [SMILES: COc1ccc2c3c1oc1cccc(c13)C13c4ccccc4-c4ccccc4C21c1ccccc1-c1ccccc13] | 43% |

Example S30

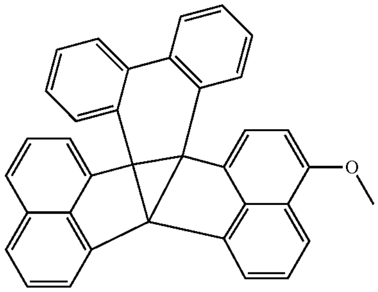 [SMILES: COc1ccc2c3c(cccc13)C13c4cccc5cccc(c45)C14c1ccccc1-c1ccccc1C243]

A mixture of 3.1 g (10 mmol) of 3-methoxyacenaphth[1,2-a]acenaphthylene [1088585-98-1], 20.4 g (100 mmol) of iodobenzene [591-50-4], 11.1 g (80 mmol) of potassium carbonate, 6.5 g (20 mmol) of tetra-n-butylammonium bromide and 112 mg (0.5 mmol) of palladium(II) acetate in 100 ml of DMF is stirred at 120° C. in a stirred autoclave under argon for 10 days. After cooling, the reaction mixture is diluted with 1000 ml of dichloromethane and filtered through a silica gel bed in the form of a slurry. The filtrate is freed of the dichloromethane under reduced pressure and then of the excess iodobenzene under high vacuum. The residue is separated by flash chromatography on an automated column system (Torrent from A. Semrau). Yield: 2.6 g (5.6 mmol), 56%; purity: 95% by $^{1}$H NMR.

Example S50

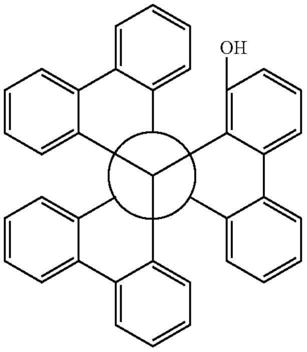 [SMILES: Cc1ccccc1-c1ccccc1C(c1ccccc1-c1ccccc1C)c1c(O)cccc1-c1ccccc1C]

A mixture of 51.2 g (100 mmol) of S10 and 250 g of pyridinium hydrochloride is heated to 200° C. for 6 h. The reaction mixture is left to cool to 100° C., and 1000 ml of water and then 50 ml of 2 N hydrochloric acid are cautiously added dropwise with good stirring without further heating. After cooling to about 30° C., the precipitated solids are filtered off with suction and washed three times with 200 ml each time of water and once with 100 ml of methanol, and dried under reduced pressure. Yield: 38.8 g (73 mmol), 73%; purity: 97% by $^{1}$H NMR.

In an analogous manner, it is possible to prepare the following compounds:

| Ex. | Reactant | Product | Yield |
|---|---|---|---|
| S51 | S11 | 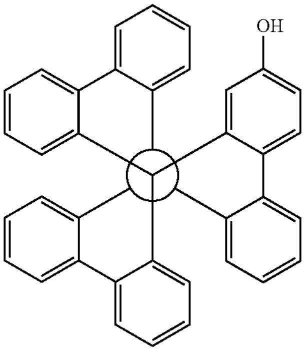 [SMILES: Oc1ccc2c(c1)C13c4ccccc4-c4ccccc4C1(c1ccccc1-c1ccccc13)c1ccccc1-2] | 87% |
| S52 | S12 | 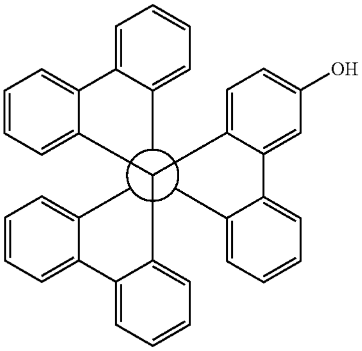 [SMILES: Oc1ccc2c(c1)-c1ccccc1C13c4ccccc4-c4ccccc4C21c1ccccc1-c1ccccc13] | 85% |
| S53 | S13 | 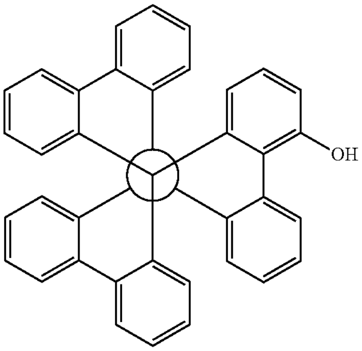 [SMILES: Oc1cccc2c1-c1ccccc1C13c4ccccc4-c4ccccc4C21c1ccccc1-c1ccccc13] | 79% |
| S54 | S14 | 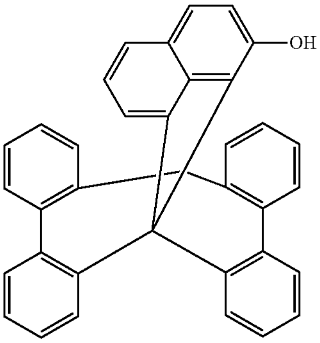 [SMILES: Oc1ccc2cccc3c2c1C31c2ccccc2-c2ccccc2Cc2ccccc2-c2ccccc21] | 80% |
-continued
| Ex. | Reactant | Product | Yield |
|---|---|---|---|
| S55 | S15 | 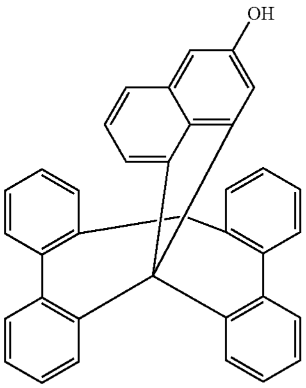 [SMILES: Oc1cc2c3c(cccc3c1)C21c2ccccc2-c2ccccc2Cc2ccccc2-c2ccccc21] | 87% |
| S56 | S16 | 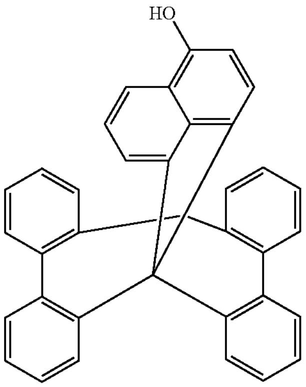 [SMILES: Oc1ccc2c3c(cccc13)C21c2ccccc2-c2ccccc2Cc2ccccc2-c2ccccc21] | 85% |
| S57 | S30 | 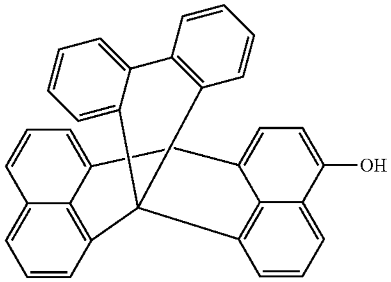 [SMILES: Oc1ccc2c3c(cccc13)C1(c3ccccc3-c3ccccc31)c1cccc3cccc(c13)C2] | 90% |
| S58 | S17 | 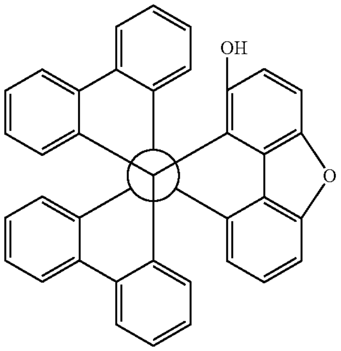 [SMILES: Oc1ccc2oc3cccc4c3c2c1C12c3ccccc3-c3ccccc3C41c1ccccc1-c1ccccc12] | 88% |

-continued

| Ex. | Reactant | Product | Yield |
|---|---|---|---|
| S59 | S18 | 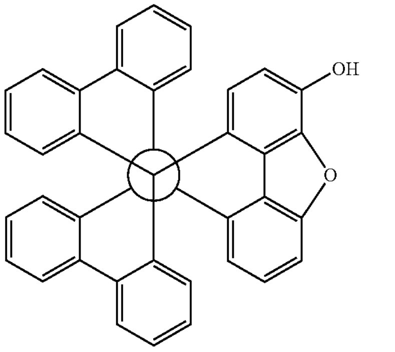 [SMILES: Oc1ccc2c3c1oc1cccc(c13)C13c4ccccc4-c4ccccc4C21c1ccccc1-c1ccccc13] | 94% |

Example S100

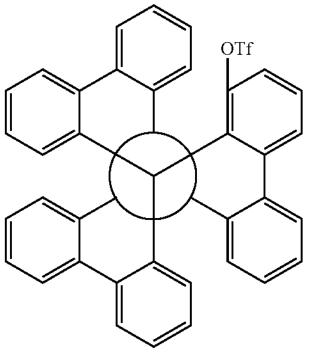 [SMILES: Cc1ccccc1-c1ccccc1C(c1ccccc1-c1ccccc1C)c1c(OS(=O)(=O)C(F)(F)F)cccc1-c1ccccc1C]

To a mixture, cooled to 0° C., of 49.7 g (100 mmol) of S50 and 24.2 ml (300 mmol) of pyridine are added dropwise, over the course of 1 h, 25.2 ml (150 mol) of trifluoromethanesulfonic anhydride $O(Tf)_2$ [358-23-6]. The mixture is stirred at 0° C. for a further 1 h, then allowed to warm up to room temperature and stirred for a further 12 h. The reaction mixture is poured into 1 l of ice-water with very good stirring, stirred for a further 10 min and extracted three times with 300 ml each time of dichloromethane. The combined organic phases are washed once with 300 ml of saturated sodium chloride solution and then dried over magnesium sulfate. After the desiccant has been filtered off and the solvent removed, the residue is recrystallized from acetonitrile. 50.3 g (80 mmol), 80%; purity: 97% by $^1H$ NMR.

In an analogous manner, it is possible to prepare the following compounds:

| Ex. | Bromide | Product | Yield |
|---|---|---|---|
| S101 | S51 | 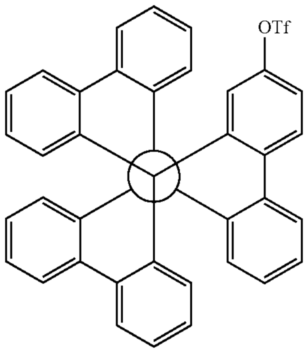 [SMILES: O=S(=O)(Oc1ccc2c(c1)C13c4ccccc4-c4ccccc4C1(c1ccccc1-c1ccccc13)c1ccccc1-2)C(F)(F)F] | 93% |
| S102 | S52 | 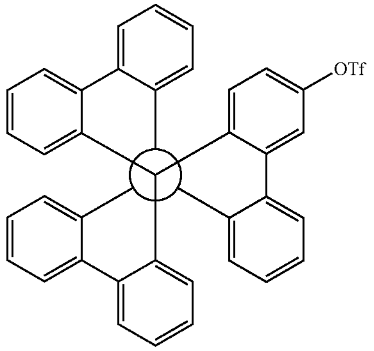 [SMILES: O=S(=O)(Oc1ccc2c(c1)-c1ccccc1C13c4ccccc4-c4ccccc4C21c1ccccc1-c1ccccc13)C(F)(F)F] | 90% |
| S103 | S53 | 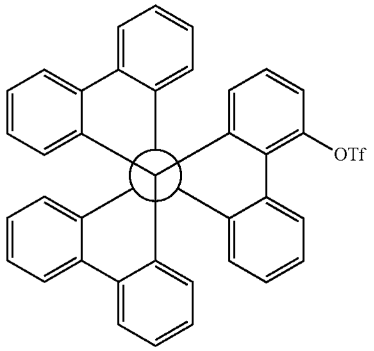 [SMILES: O=S(=O)(Oc1cccc2c1-c1ccccc1C13c4ccccc4-c4ccccc4C21c1ccccc1-c1ccccc13)C(F)(F)F] | 85% |
| S104 | S54 | 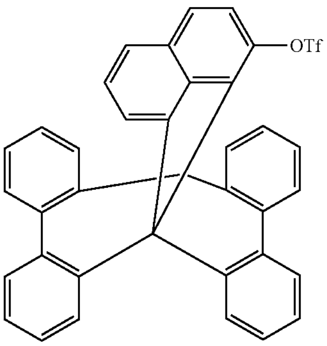 [SMILES: O=S(=O)(Oc1ccc2cccc3c2c1C31c2ccccc2-c2ccccc2Cc2ccccc2-c2ccccc21)C(F)(F)F] | 70% |

-continued

| Ex. | Bromide | Product | Yield |
|---|---|---|---|
| S105 | S55 | 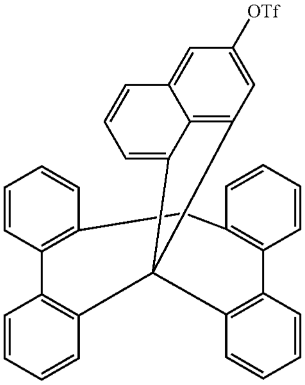 [SMILES: O=S(=O)(Oc1cc2c3c(cccc3c1)C21c2ccccc2-c2ccccc2Cc2ccccc2-c2ccccc21)C(F)(F)F] | 87% |
| S106 | S56 | 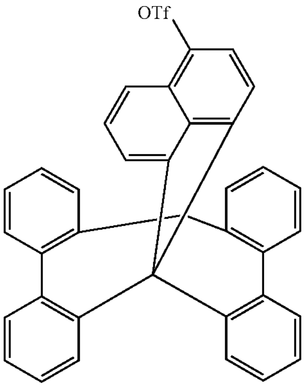 | 85% |
| S107 | S57 | 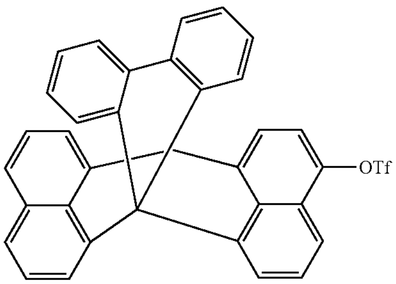 [SMILES: O=S(=O)(Oc1ccc2c3c(cccc13)C1(c3ccccc3-c3ccccc31)c1cccc3cccc(c13)C2)C(F)(F)F] | 92% |
| S108 | S58 | 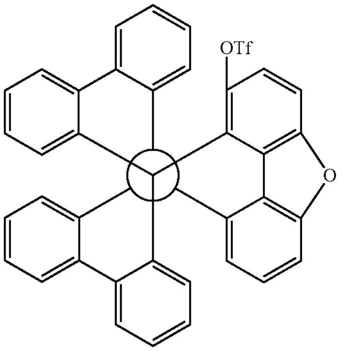 | 77% |
| S109 | S59 | 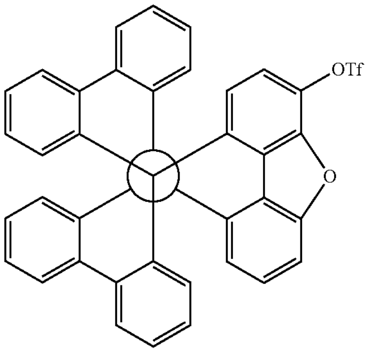 [SMILES: O=S(=O)(Oc1ccc2c3c1oc1cccc(c13)C13c4ccccc4-c4ccccc4C21c1ccccc1-c1ccccc13)C(F)(F)F] | 87% |

Example S150

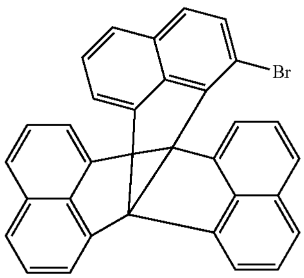 [SMILES: Brc1ccc2cccc3c2c1C12c4cccc5cccc(c45)C14c1cccc5cccc(c15)C342]

23.8 g (100 mmol) of 1-bromonaphthalene [90-11-9] and 2.4 g (100 mmol) of magnesium turnings in 800 ml of THF are used to prepare the corresponding Grignard reagent. 13.1 g (50 mmol) of 3-bromo-1,2-acenaphthylenedione [21170-55-8] are added with good stirring and the mixture is stirred at 50° C. for a further 4 h. After cooling to room temperature, the mixture is quenched by cautiously adding 20 ml of water. The THF is largely removed under reduced pressure, and the residue is taken up in 1500 ml of toluene and washed twice with water and once with saturated sodium chloride solution. For drying, 500 ml of toluene are removed on a water separator, then 10 ml of trifluoromethanesulfonic acid are added with good stirring and the reaction mixture is heated on a water separator for a further 16 h. Then a further 800 ml of toluene are distilled off, the mixture is allowed to cool to about 50° C., 500 ml of methanol are added dropwise, the mixture is stirred for a further 30 min, and the solids are filtered off with suction, washed three times with 100 ml each time of methanol and dried under reduced pressure. Yield: 8.2 g (17 mmol), 34%; purity: 97% by $^{1}H$ NMR.

In an analogous manner, it is possible to prepare the following compounds:

| Ex. | Reactant | Product | Yield |
| --- | --- | --- | --- |
| S151 | 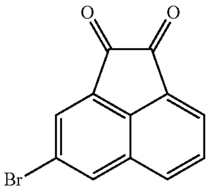 43017-97-6 | 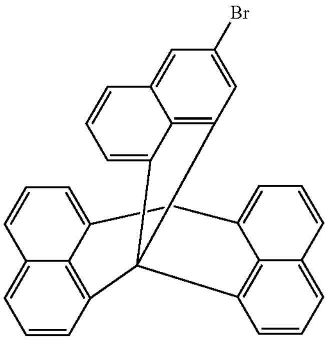 [SMILES: Brc1cc2c3c(cccc3c1)C21c2cccc3cccc(c23)Cc2cccc3cccc1c23] | 44% |
| S152 | 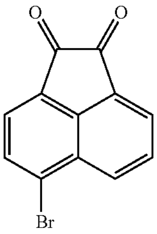 26254-35-3 | 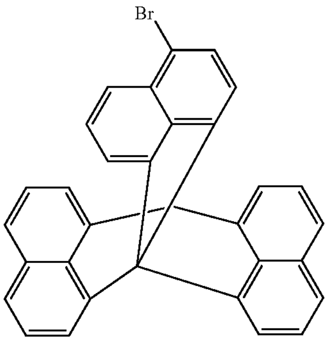 [SMILES: Brc1ccc2c3c(cccc13)C21c2cccc3cccc(c23)Cc2cccc3cccc1c23] | 46% |
| S153 | 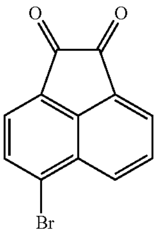 26254-35-3 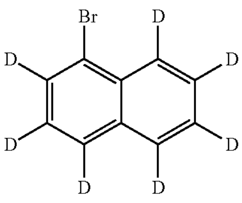 37621-57-1 | 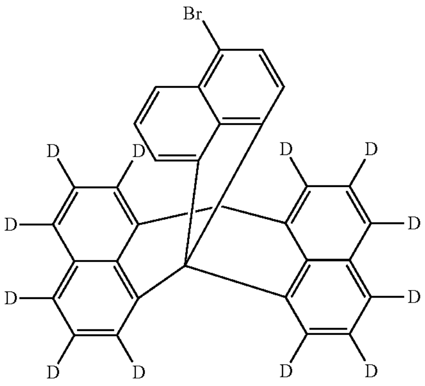 [SMILES: [2H]c1c([2H])c2c3c(c([2H])c([2H])c([2H])c3c1[2H])C1(c3cccc4c(Br)ccc1c34)c1c([2H])c([2H])c([2H])c3c([2H])c([2H])c([2H])c(c13)C2] | 44% |

B: Compounds of the Invention

Example H1

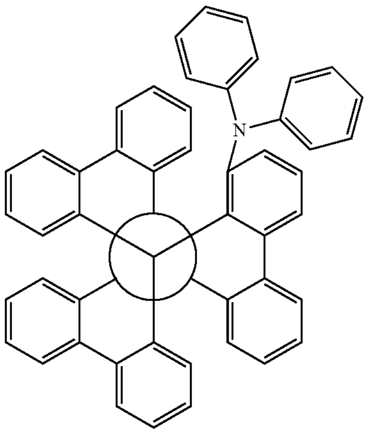 [SMILES: Cc1ccccc1-c1ccccc1C(c1ccccc1-c1ccccc1C)c1c(-c2ccccc2C)cccc1N(c1ccccc1)c1ccccc1]

A mixture of 62 0.8 g (100 mmol) of S100, 18.6 g (110 mmol) of diphenylamine, 13.5 g (120 mmol) of sodium tert-butoxide, 449 mg (2 mmol) of palladium acetate, 1230 mg (3 mmol) of SPhos and 800 ml of toluene is heated under reflux for 16 h. 1 ml of hydrazine hydrate is added and the mixture is heated under reflux for 1 h. 400 ml of water are added to the reaction mixture at 50° C. while stirring, then the organic phase is separated off and filtered while still warm through a Celite bed in the form of a toluene slurry. The filtrate is concentrated to about 100 ml and then 200 ml of methanol are added to the filtrate while hot with good stirring. The mixture is left to cool while stirring, and the crystallized product is filtered off and washed three times with 100 ml each time of methanol. Further purification is effected by hot extraction five times with toluene (amount initially charged 250 ml) and subsequent double fractional sublimation under reduced pressure (T about 300° C., p about $10^{-6}$ mbar). Yield: 45.0 g (68 mmol), 68%; purity: about 99.9% by HPLC.

In an analogous manner, it is possible to prepare the following compounds:

| Ex. | Reactants | Product | Yield |
| --- | --- | --- | --- |
| H2 | S100 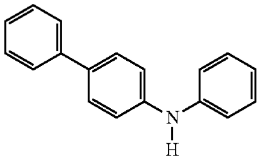 32228-99-2 | 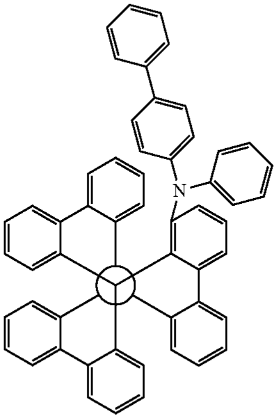 [SMILES: c1ccc(-c2ccc(N(c3ccccc3)c3cccc4c3C35c6ccccc6-c6ccccc6C3(c3ccccc3-c3ccccc35)c3ccccc3-4)cc2)cc1] | 55% |
| H3 | S100 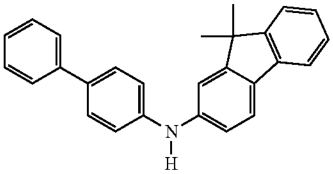 897671-69-1 | 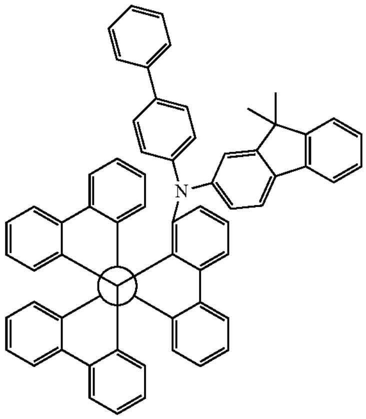 [SMILES: CC1(C)c2ccccc2-c2ccc(N(c3ccc(-c4ccccc4)cc3)c3cccc4c3C35c6ccccc6-c6ccccc6C3(c3ccccc3-c3ccccc35)c3ccccc3-4)cc21] | 46% |

-continued
| Ex. | Reactants | Product | Yield |
| --- | --- | --- | --- |
| H4 | S100 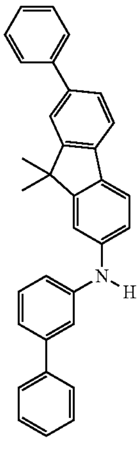 1372775-63-7 | 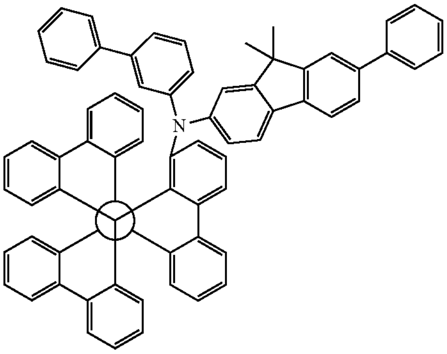 [SMILES: CC1(C)c2cc(-c3ccccc3)ccc2-c2ccc(N(c3cccc(-c4ccccc4)c3)c3cccc4c3C35c6ccccc6-c6ccccc6C3(c3ccccc3-c3ccccc35)c3ccccc3-4)cc21] | 43% |
| H5 | S100 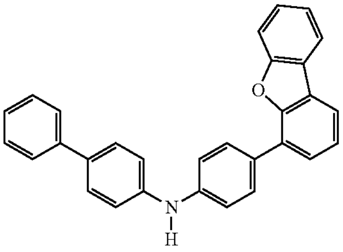 955959-89-4 | 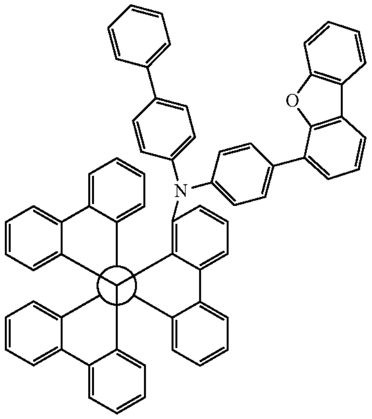 [SMILES: c1ccc(-c2ccc(N(c3ccc(-c4cccc5c4oc4ccccc45)cc3)c3cccc4c3C35c6ccccc6-c6ccccc6C3(c3ccccc3-c3ccccc35)c3ccccc3-4)cc2)cc1] | 48% |
| H6 | S100 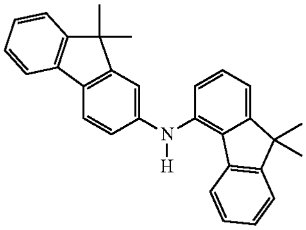 1644054-07-8 | 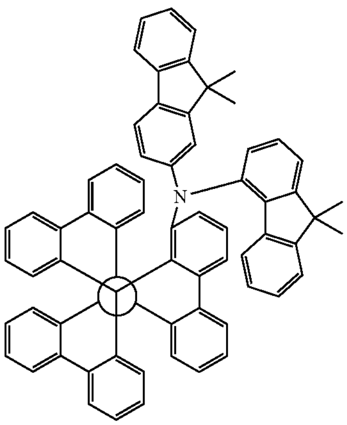 [SMILES: CC1(C)c2ccccc2-c2ccc(N(c3cccc4c3-c3ccccc3C4(C)C)c3cccc4c3C35c6ccccc6-c6ccccc6C3(c3ccccc3-c3ccccc35)c3ccccc3-4)cc21] | 40% |

-continued
| Ex. | Reactants | Product | Yield |
| --- | --- | --- | --- |
| H7 | S100 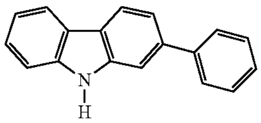 88590-00-5 | 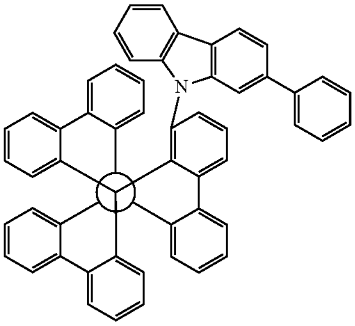 [SMILES: c1ccc(-c2ccc3c4ccccc4n(-c4cccc5c4C46c7ccccc7-c7ccccc7C4(c4ccccc4-c4ccccc46)c4ccccc4-5)c3c2)cc1] | 52% |
| H8 | S100 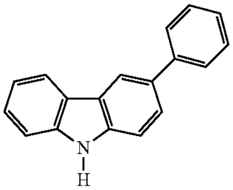 103012-26-6 | 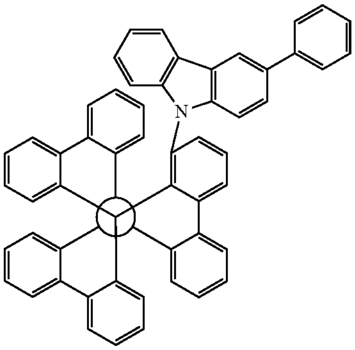 [SMILES: c1ccc(-c2ccc3c(c2)c2ccccc2n3-c2cccc3c2C24c5ccccc5-c5ccccc5C2(c2ccccc2-c2ccccc24)c2ccccc2-3)cc1] | 49% |
| H9 | S101 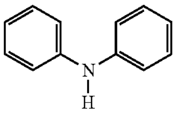 122-39-4 | 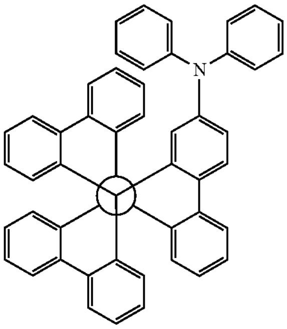 [SMILES: c1ccc(N(c2ccccc2)c2ccc3c(c2)C24c5ccccc5-c5ccccc5C2(c2ccccc2-c2ccccc24)c2ccccc2-3)cc1] | 75% |
| H10 | S101 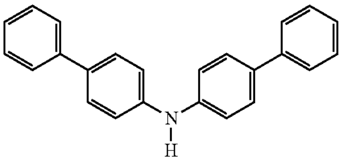 102113-98-4 | 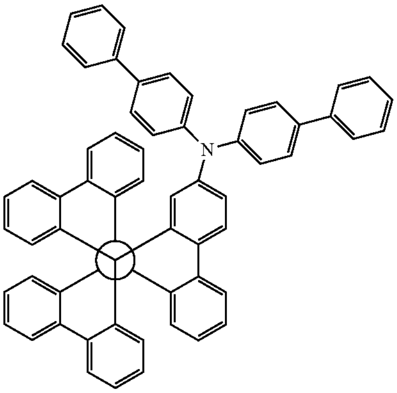 [SMILES: c1ccc(-c2ccc(N(c3ccc(-c4ccccc4)cc3)c3ccc4c(c3)C35c6ccccc6-c6ccccc6C3(c3ccccc3-c3ccccc35)c3ccccc3-4)cc2)cc1] | 73% |

-continued
| Ex. | Reactants | Product | Yield |
|---|---|---|---|
| H11 | S101 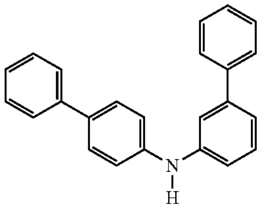 570391-47-8 | 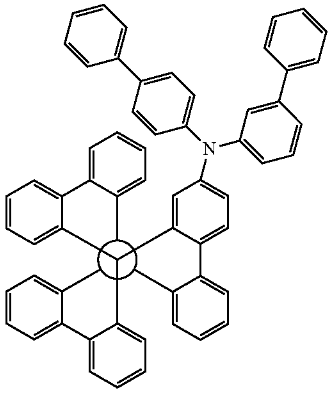 [SMILES: c1ccc(-c2ccc(N(c3cccc(-c4ccccc4)c3)c3ccc4c(c3)C35c6ccccc6-c6ccccc6C3(c3ccccc3-c3ccccc35)c3ccccc3-4)cc2)cc1] | 75% |
| H12 | S101 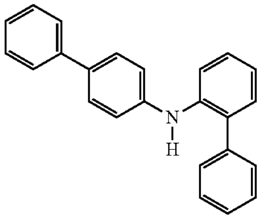 1372775-52-4 | 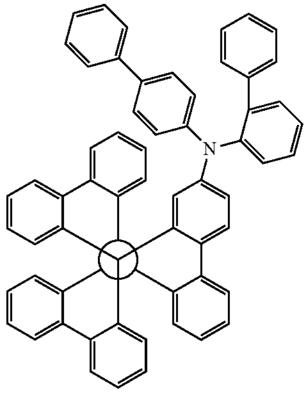 [SMILES: c1ccc(-c2ccc(N(c3ccc4c(c3)C35c6ccccc6-c6ccccc6C3(c3ccccc3-c3ccccc35)c3ccccc3-4)c3ccccc3-c3ccccc3)cc2)cc1] | 70% |
| H13 | S101 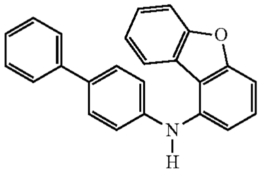 1776057-10-3 | 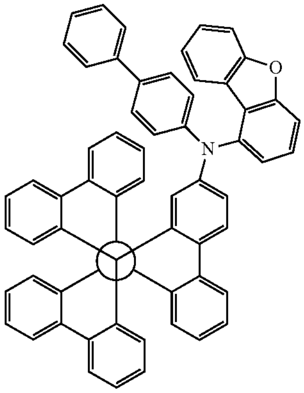 [SMILES: c1ccc(-c2ccc(N(c3ccc4c(c3)C35c6ccccc6-c6ccccc6C3(c3ccccc3-c3ccccc35)c3ccccc3-4)c3cccc4oc5ccccc5c34)cc2)cc1] | 68% |
| H14 | S101 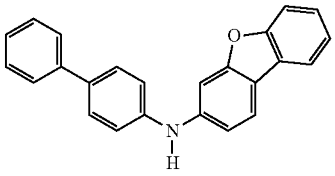 1290039-85-8 | 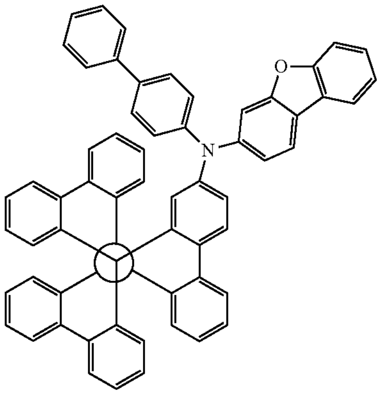 [SMILES: c1ccc(-c2ccc(N(c3ccc4c(c3)C35c6ccccc6-c6ccccc6C3(c3ccccc3-c3ccccc35)c3ccccc3-4)c3ccc4c(c3)oc3ccccc34)cc2)cc1] | 74% |

-continued
| Ex. | Reactants | Product | Yield |
|---|---|---|---|
| H15 | S101<br>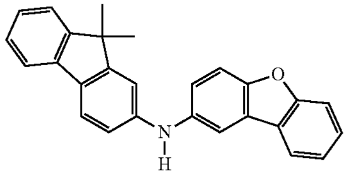<br>1300028-94-7 | 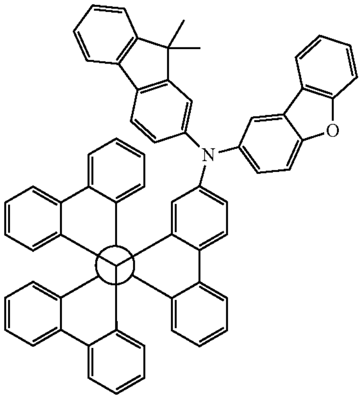 [SMILES: CC1(C)c2ccccc2-c2ccc(N(c3ccc4c(c3)C35c6ccccc6-c6ccccc6C3(c3ccccc3-c3ccccc35)c3ccccc3-4)c3ccc4oc5ccccc5c4c3)cc21] | 70% |
| H16 | S101<br>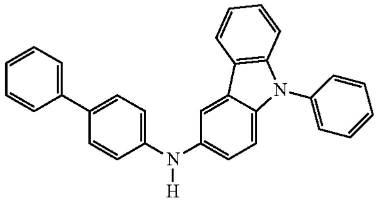<br>1002762-60-8 | 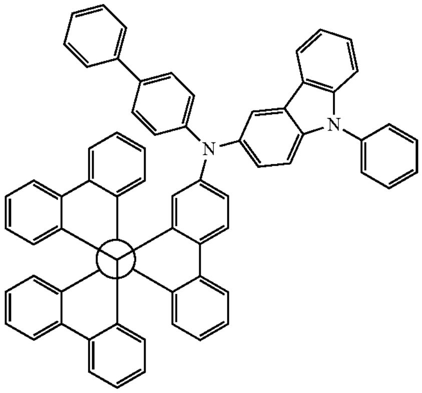 [SMILES: c1ccc(-c2ccc(N(c3ccc4c(c3)C35c6ccccc6-c6ccccc6C3(c3ccccc3-c3ccccc35)c3ccccc3-4)c3ccc4c(c3)c3ccccc3n4-c3ccccc3)cc2)cc1] | 71% |
| H17 | S101<br>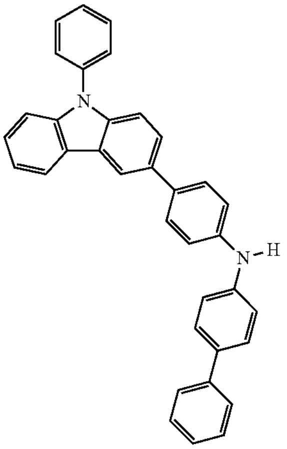<br>1160294-96-1 | 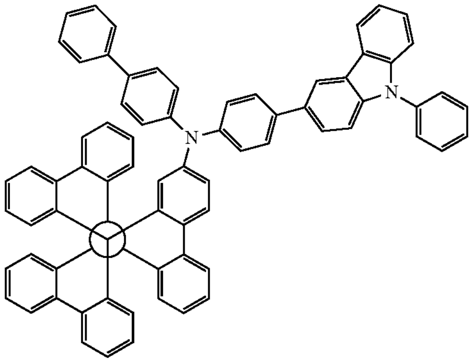 [SMILES: c1ccc(-c2ccc(N(c3ccc(-c4ccc5c(c4)c4ccccc4n5-c4ccccc4)cc3)c3ccc4c(c3)C35c6ccccc6-c6ccccc6C3(c3ccccc3-c3ccccc35)c3ccccc3-4)cc2)cc1] | 69% |

-continued
| Ex. | Reactants | Product | Yield |
| --- | --- | --- | --- |
| H18 | S101<br>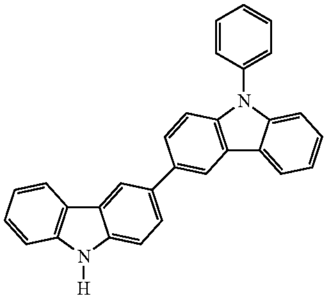<br>1060735-14-9 | 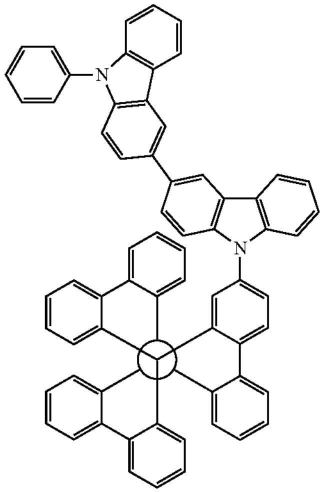 | 76% |
| H19 | S101<br>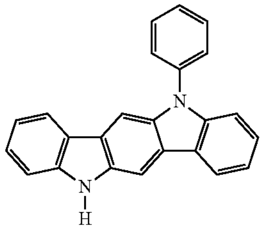<br>1316311-27-9 | 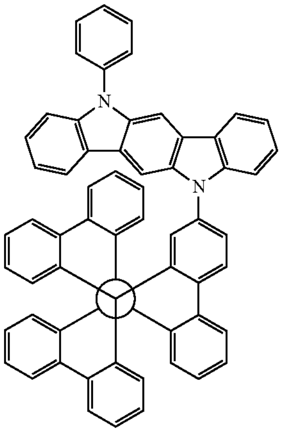 [SMILES: c1ccc(-n2c3ccccc3c3cc4c(cc32)c2ccccc2n4-c2ccc3c(c2)C24c5ccccc5-c5ccccc5C2(c2ccccc2-c2ccccc24)c2ccccc2-3)cc1] | 70% |
| H20 | S102<br>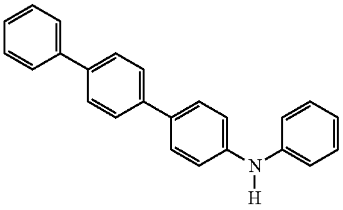<br>897671-81-7 | 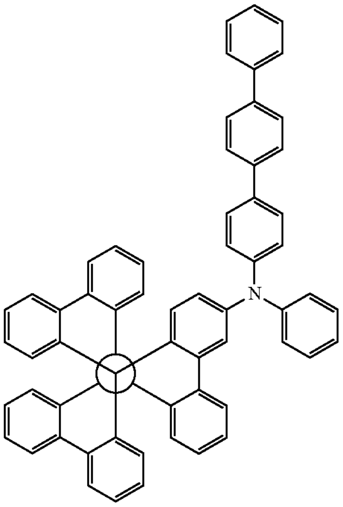 [SMILES: c1ccc(-c2ccc(-c3ccc(N(c4ccccc4)c4ccc5c(c4)-c4ccccc4C46c7ccccc7-c7ccccc7C54c4ccccc4-c4ccccc46)cc3)cc2)cc1] | 78% |

-continued
| Ex. | Reactants | Product | Yield |
|---|---|---|---|
| H21 | S102<br>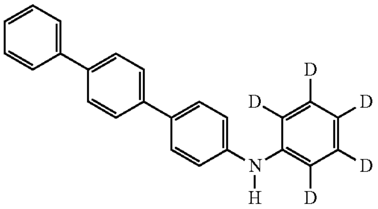<br>1879981-35-7 | 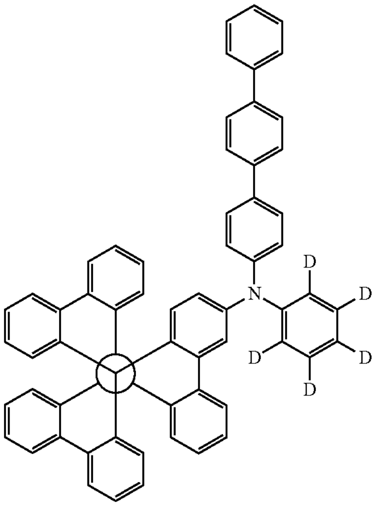 [SMILES: [2H]c1c([2H])c([2H])c(N(c2ccc(-c3ccc(-c4ccccc4)cc3)cc2)c2ccc3c(c2)-c2ccccc2C24c5ccccc5-c5ccccc5C32c2ccccc2-c2ccccc24)c([2H])c1[2H]] | 75% |
| H22 | S102<br>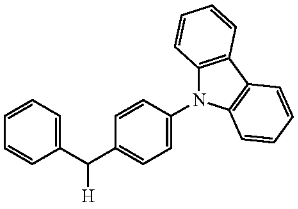<br>858641-06-5 | 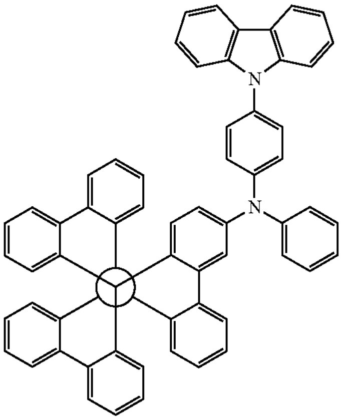 [SMILES: c1ccc(N(c2ccc(-n3c4ccccc4c4ccccc43)cc2)c2ccc3c(c2)-c2ccccc2C24c5ccccc5-c5ccccc5C32c2ccccc2-c2ccccc24)cc1] | 73% |
| H23 | S102<br>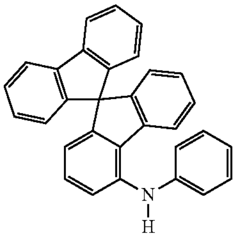<br>1454679-32-3 | 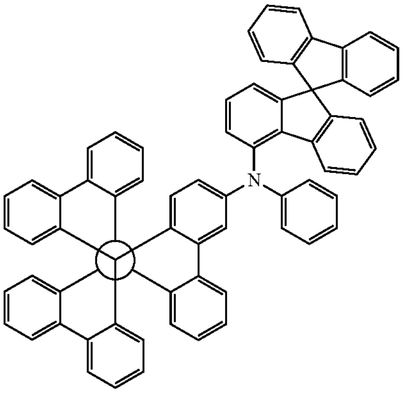 [SMILES: c1ccc(N(c2ccc3c(c2)-c2ccccc2C24c5ccccc5-c5ccccc5C32c2ccccc2-c2ccccc24)c2cccc3c2-c2ccccc2C32c3ccccc3-c3ccccc32)cc1] | 70% |

-continued
| Ex. | Reactants | Product | Yield |
|---|---|---|---|
| H24 | S102 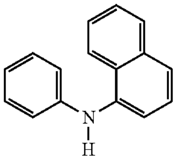 90-30-2 | 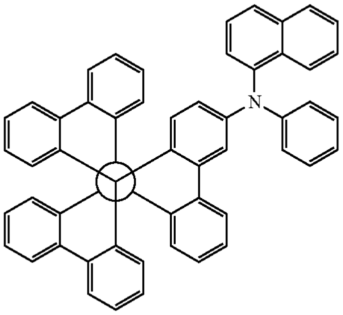 [SMILES: c1ccc(N(c2ccc3c(c2)-c2ccccc2C24c5ccccc5-c5ccccc5C32c2ccccc2-c2ccccc24)c2cccc3ccccc23)cc1] | 74% |
| H25 | S102 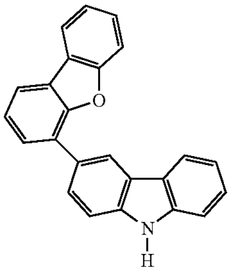 1346669-46-2 | 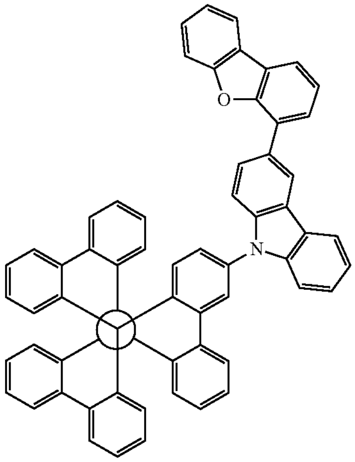 [SMILES: c1ccc2c(c1)-c1ccccc1C13c4ccccc4-c4ccccc4C21c1ccccc1-c1cc(-n2c4ccccc4c4cc(-c5cccc6c5oc5ccccc56)ccc42)ccc13] | 71% |
| H26 | S103 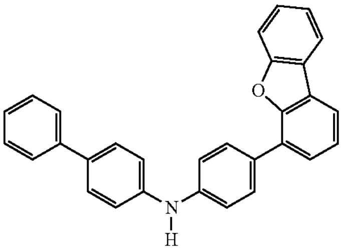 955959-89-4 | 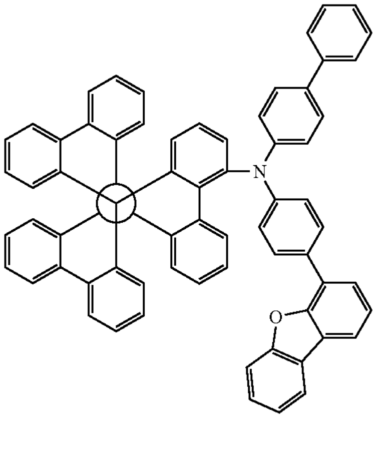 [SMILES: c1ccc(-c2ccc(N(c3ccc(-c4cccc5c4oc4ccccc45)cc3)c3cccc4c3-c3ccccc3C35c6ccccc6-c6ccccc6C43c3ccccc3-c3ccccc35)cc2)cc1] | 68% |

-continued
| Ex. | Reactants | Product | Yield |
|---|---|---|---|
| H27 | S103<br>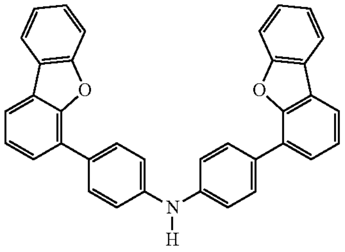<br>955959-91-8 | 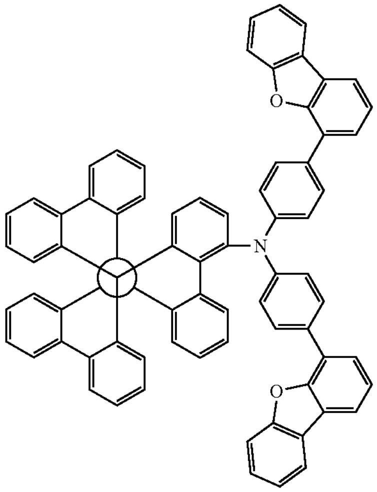 [SMILES: c1ccc2c(c1)-c1ccccc1C13c4ccccc4-c4ccccc4C21c1ccccc1-c1c(N(c2ccc(-c4cccc5c4oc4ccccc45)cc2)c2ccc(-c4cccc5c4oc4ccccc45)cc2)cccc13] | 65% |
| H28 | S103<br>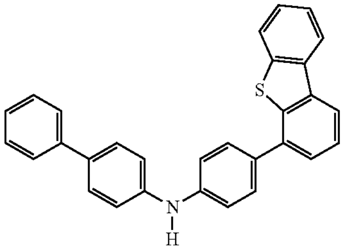<br>1431879-08-1 | 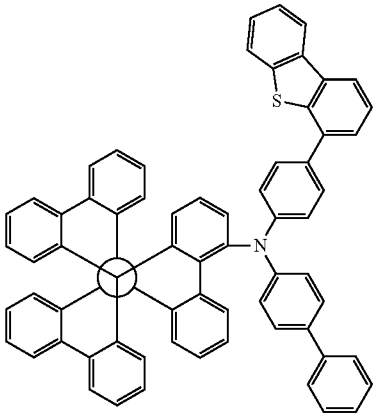 [SMILES: c1ccc(-c2ccc(N(c3ccc(-c4cccc5c4sc4ccccc45)cc3)c3cccc4c3-c3ccccc3C35c6ccccc6-c6ccccc6C43c3ccccc3-c3ccccc35)cc2)cc1] | 67% |
| H29 | S103<br>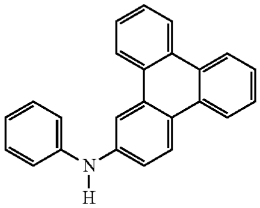<br>1203922-52-4 | 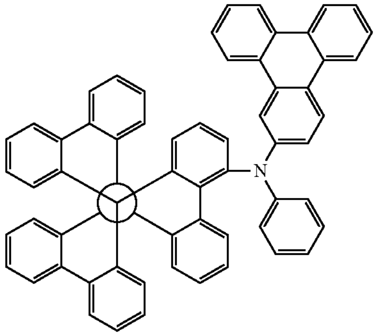 [SMILES: c1ccc(N(c2ccc3c4ccccc4c4ccccc4c3c2)c2cccc3c2-c2ccccc2C24c5ccccc5-c5ccccc5C32c2ccccc2-c2ccccc24)cc1] | 63% |

-continued
| Ex. | Reactants | Product | Yield |
| --- | --- | --- | --- |
| H30 | S103 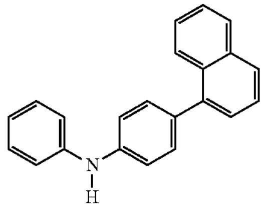 897671-78-2 | 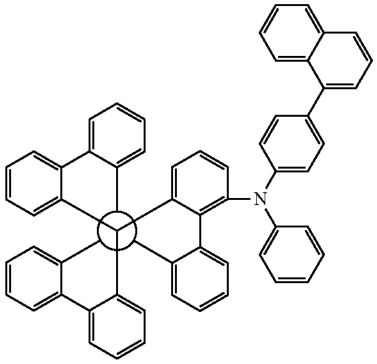 [SMILES: c1ccc(N(c2ccc(-c3cccc4ccccc34)cc2)c2cccc3c2-c2ccccc2C24c5ccccc5-c5ccccc5C32c2ccccc2-c2ccccc24)cc1] | 65% |
| H31 | S103 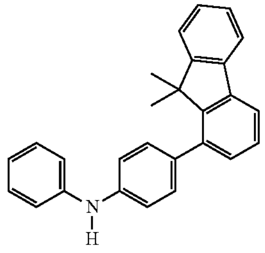 1592942-46-5 | 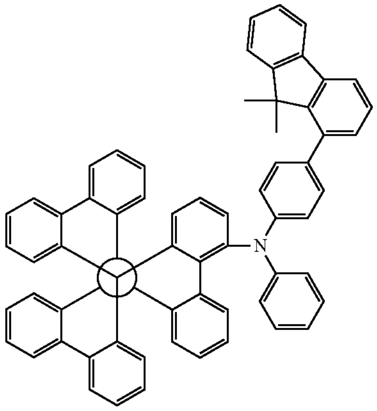 [SMILES: CC1(C)c2ccccc2-c2cccc(-c3ccc(N(c4ccccc4)c4cccc5c4-c4ccccc4C46c7ccccc7-c7ccccc7C54c4ccccc4-c4ccccc46)cc3)c21] | 66% |
| H32 | S103 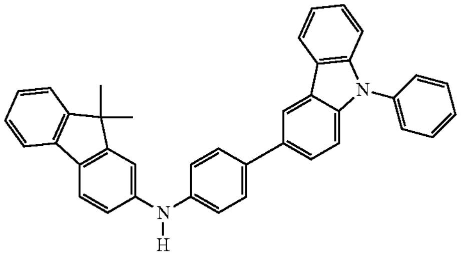 1592942-46-5 | 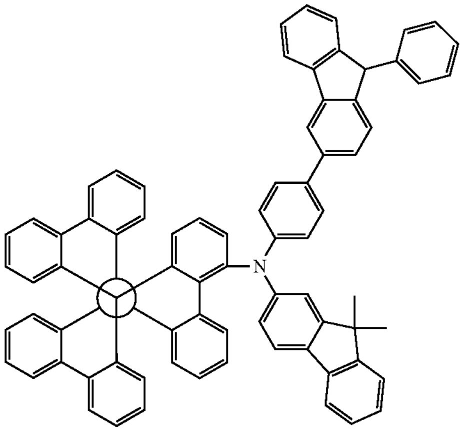 [SMILES: CC1(C)c2ccccc2-c2ccc(N(c3ccc(-c4ccc5c(c4)-c4ccccc4C5c4ccccc4)cc3)c3cccc4c3-c3ccccc3C35c6ccccc6-c6ccccc6C43c3ccccc3-c3ccccc35)cc21] | 65% |
| H33 | S103 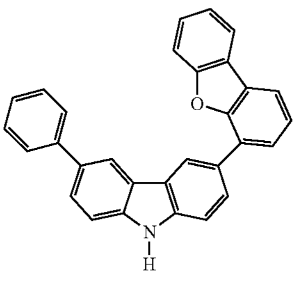 1567814-83-8 | 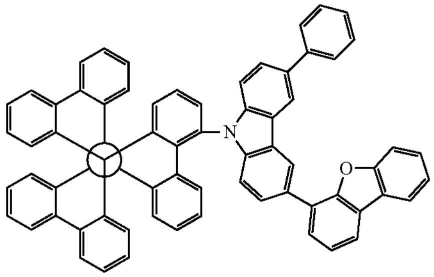 [SMILES: c1ccc(-c2ccc3c(c2)c2cc(-c4cccc5c4oc4ccccc45)ccc2n3-c2cccc3c2-c2ccccc2C24c5ccccc5-c5ccccc5C32c2ccccc2-c2ccccc24)cc1] | 67% |

-continued
| Ex. | Reactants | Product | Yield |
| --- | --- | --- | --- |
| H34 | S103 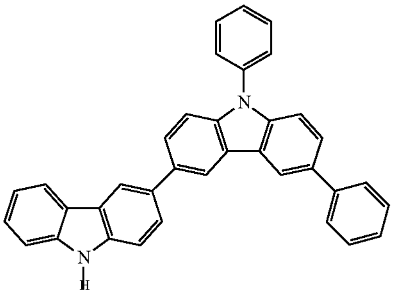 1383628-18-9 | 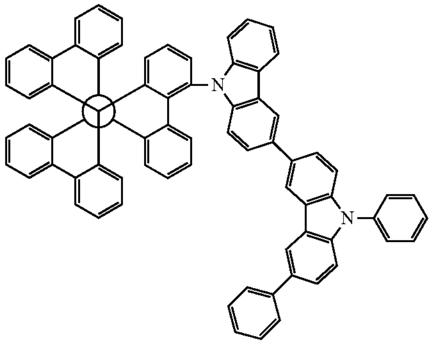 [SMILES: c1ccc(-c2ccc3c(c2)c2cc(-c4ccc5c(c4)c4ccccc4n5-c4cccc5c4-c4ccccc4C46c7ccccc7-c7ccccc7C54c4ccccc4-c4ccccc46)ccc2n3-c2ccccc2)cc1] | 62% |
| H35 | S103 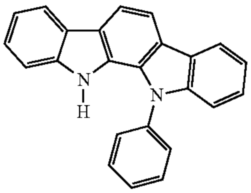 1024598-06-8 | 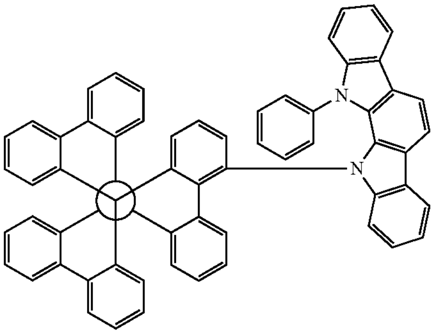 [SMILES: c1ccc(-n2c3ccccc3c3ccc4c5ccccc5n(-c5cccc6c5-c5ccccc5C57c8ccccc8-c8ccccc8C65c5ccccc5-c5ccccc57)c4c32)cc1] | 46% |
| H36 | S104 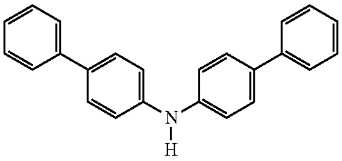 102113-98-4 | 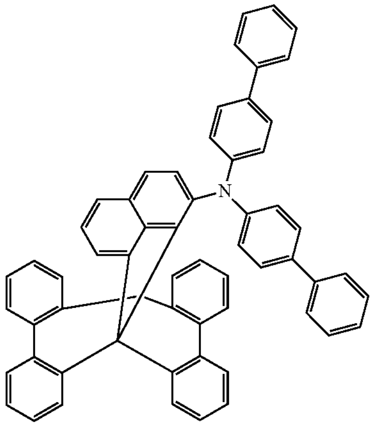 [SMILES: c1ccc(-c2ccc(N(c3ccc(-c4ccccc4)cc3)c3ccc4cccc5c4c3C53c4ccccc4-c4ccccc4Cc4ccccc4-c4ccccc43)cc2)cc1] | 39% |
| H37 | S104 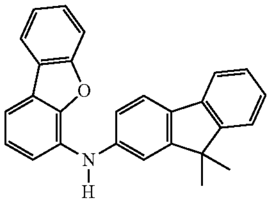 1426933-82-5 | 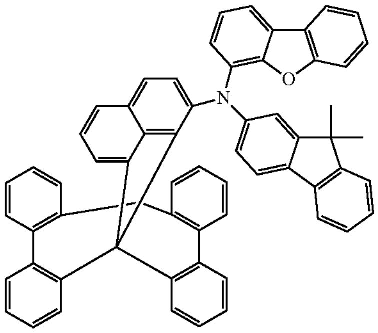 [SMILES: CC1(C)c2ccccc2-c2ccc(N(c3ccc4cccc5c4c3C53c4ccccc4-c4ccccc4Cc4ccccc4-c4ccccc43)c3cccc4c3oc3ccccc34)cc21] | 41% |

-continued
| Ex. | Reactants | Product | Yield |
|---|---|---|---|
| H38 | S105 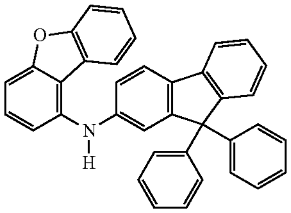 1923735-81-2 | 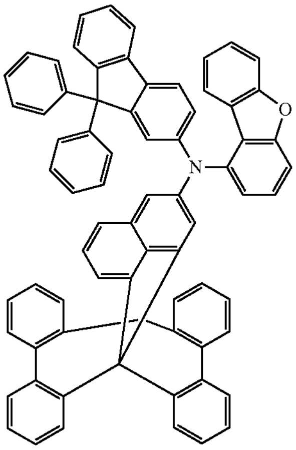 [SMILES: c1ccc(C2(c3ccccc3)c3ccccc3-c3ccc(N(c4cc5c6c(cccc6c4)C54c5ccccc5-c5ccccc5Cc5ccccc5-c5ccccc54)c4cccc5oc6ccccc6c45)cc32)cc1] | 65% |
| H39 | S105 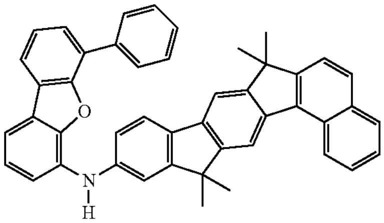 1579281-09-6 | 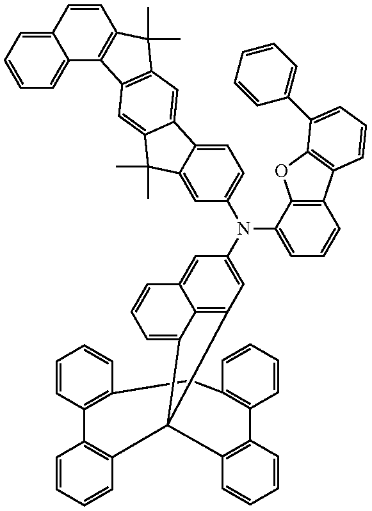 [SMILES: CC1(C)c2cc(N(c3cc4c5c(cccc5c3)C43c4ccccc4-c4ccccc4Cc4ccccc4-c4ccccc43)c3cccc4c3oc3c(-c5ccccc5)cccc34)ccc2-c2cc3c(cc21)-c1c(ccc2ccccc12)C3(C)C] | 69% |
| H40 | S106 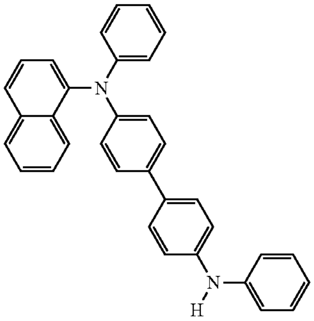 352359-41-2 | 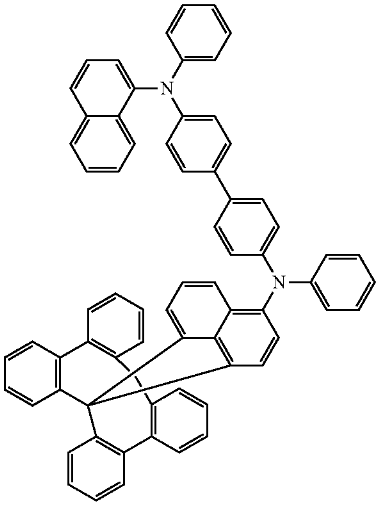 [SMILES: c1ccc(N(c2ccc(-c3ccc(N(c4ccccc4)c4ccc5c6c(cccc46)C54c5ccccc5-c5ccccc5Cc5ccccc5-c5ccccc54)cc3)cc2)c2cccc3ccccc23)cc1] | 65% |

-continued
| Ex. | Reactants | Product | Yield |
|---|---|---|---|
| H41 | S106 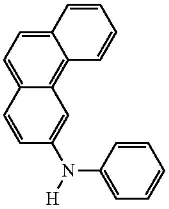 1357009-66-5 | 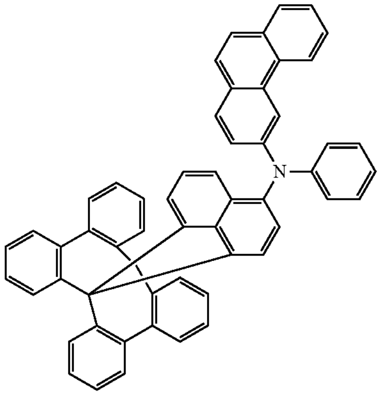 [SMILES: c1ccc(N(c2ccc3ccc4ccccc4c3c2)c2ccc3c4c(cccc24)C32c3ccccc3-c3ccccc3Cc3ccccc3-c3ccccc32)cc1] | 62% |
| H42 | S106 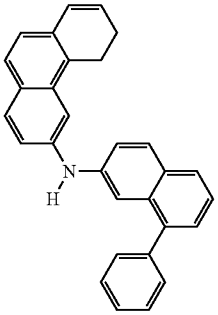 1592942-92-1 | 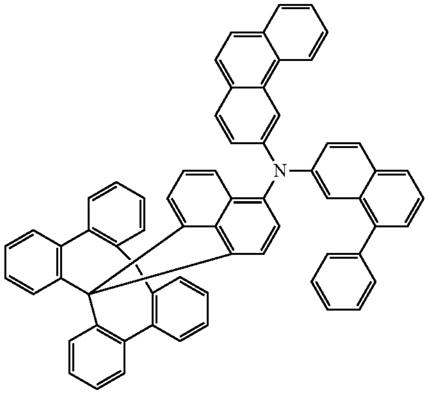 [SMILES: c1ccc(-c2cccc3ccc(N(c4ccc5ccc6ccccc6c5c4)c4ccc5c6c(cccc46)C54c5ccccc5-c5ccccc5Cc5ccccc5-c5ccccc54)cc23)cc1] | 68% |
| H43 | S106 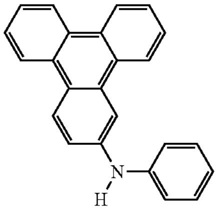 1203922-52-4 | 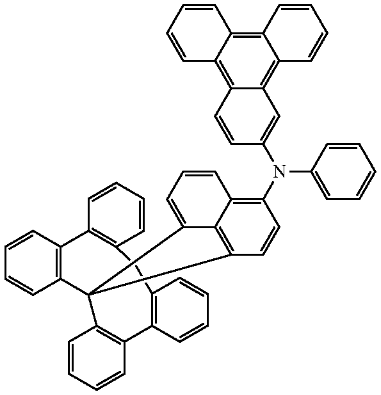 [SMILES: c1ccc(N(c2ccc3c4ccccc4c4ccccc4c3c2)c2ccc3c4c(cccc24)C32c3ccccc3-c3ccccc3Cc3ccccc3-c3ccccc32)cc1] | 67% |
| H44 | S106 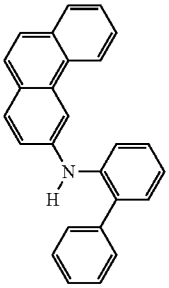 1505471-50-0 | 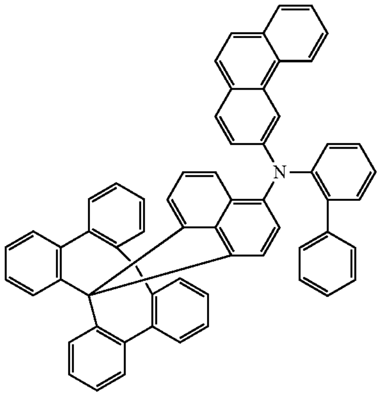 [SMILES: c1ccc(-c2ccccc2N(c2ccc3ccc4ccccc4c3c2)c2ccc3c4c(cccc24)C32c3ccccc3-c3ccccc3Cc3ccccc3-c3ccccc32)cc1] | 69% |

-continued
| Ex. | Reactants | Product | Yield |
|---|---|---|---|
| H45 | S107<br>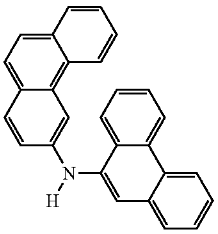<br>1592944-07-4 | 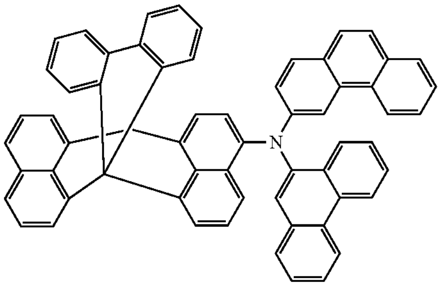 [SMILES: c1ccc2c(c1)-c1ccccc1C21c2cccc3cccc(c23)Cc2ccc(N(c3ccc4ccc5ccccc5c4c3)c3cc4ccccc4c4ccccc34)c3cccc1c23] | 66% |
| H46 | S107<br>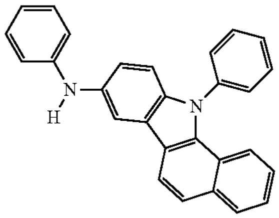<br>1642566-93-5 | 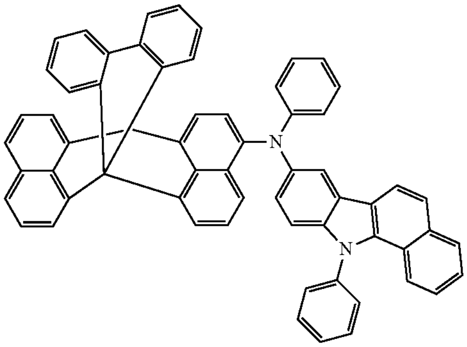 [SMILES: c1ccc(N(c2ccc3c(c2)c2ccc4ccccc4c2n3-c2ccccc2)c2ccc3c4c(cccc24)C2(c4ccccc4-c4ccccc42)c2cccc4cccc(c24)C3)cc1] | 67% |
| H47 | S107<br>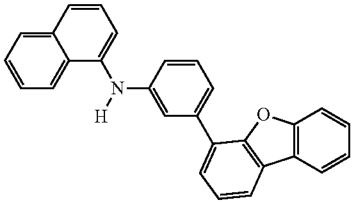<br>955959-90-7 | 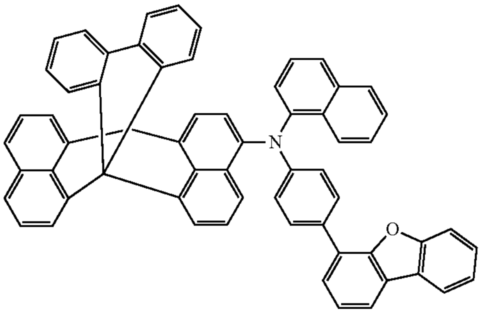 [SMILES: c1ccc2c(c1)-c1ccccc1C21c2cccc3cccc(c23)Cc2ccc(N(c3ccc(-c4cccc5c4oc4ccccc45)cc3)c3cccc4ccccc34)c3cccc1c23] | 65% |
| H48 | S150<br>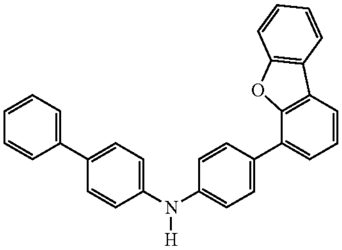<br>955959-89-4 | 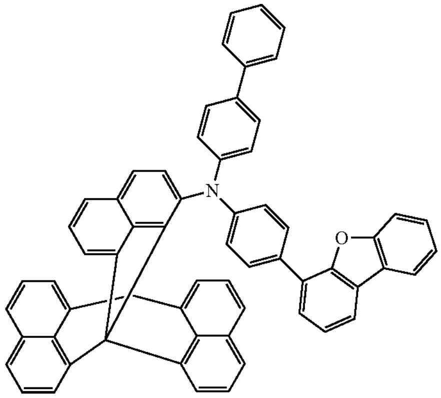 [SMILES: c1ccc(-c2ccc(N(c3ccc(-c4cccc5c4oc4ccccc45)cc3)c3ccc4cccc5c4c3C53c4cccc5cccc(c45)Cc4cccc5cccc3c45)cc2)cc1] | 40% |

-continued
| Ex. | Reactants | Product | Yield |
|---|---|---|---|
| H49 | S150 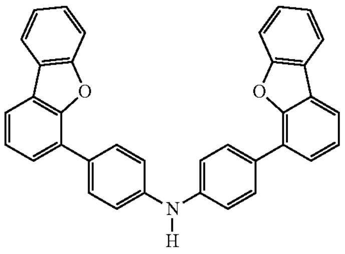 955959-91-8 | 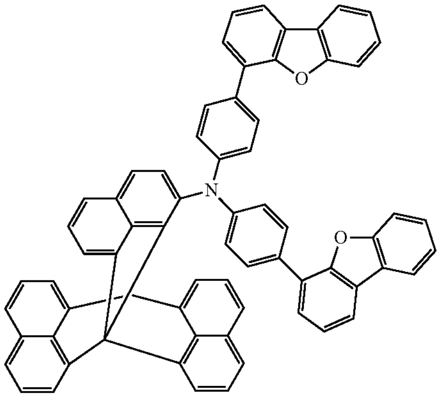 [SMILES: c1cc2c3c(cccc3c1)C1(c3cccc4cccc(c34)C2)c2cccc3ccc(N(c4ccc(-c5cccc6c5oc5ccccc56)cc4)c4ccc(-c5cccc6c5oc5ccccc56)cc4)c1c23] | 39% |
| H50 | S150 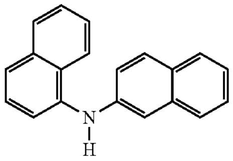 4669-06-1 | 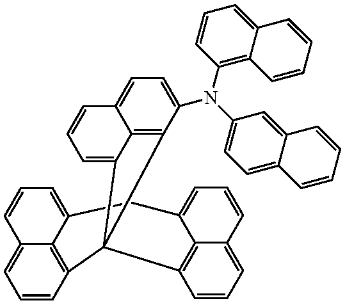 [SMILES: c1ccc2cc(N(c3ccc4cccc5c4c3C53c4cccc5cccc(c45)Cc4cccc5cccc3c45)c3cccc4ccccc34)ccc2c1] | 42% |
| H51 | S151 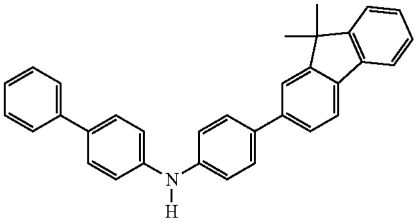 1159425-90-7 | 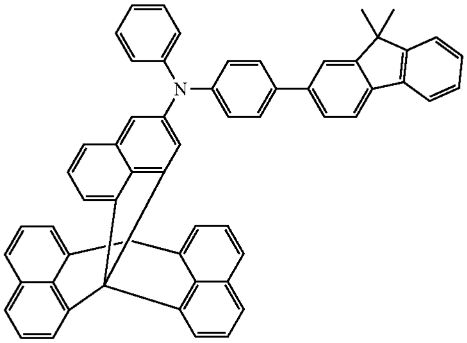 [SMILES: CC1(C)c2ccccc2-c2ccc(-c3ccc(N(c4ccccc4)c4cc5c6c(cccc6c4)C54c5cccc6cccc(c56)Cc5cccc6cccc4c56)cc3)cc21] | 68% |
| H52 | S151 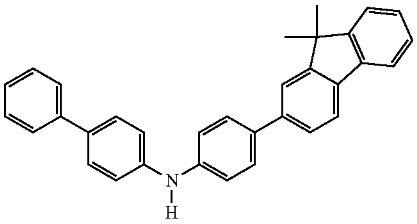 1267247-99-3 | 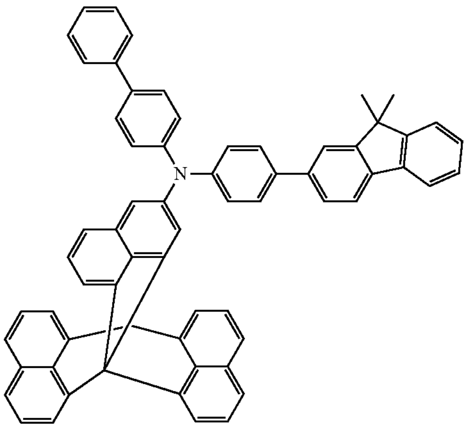 [SMILES: CC1(C)c2ccccc2-c2ccc(-c3ccc(N(c4ccc(-c5ccccc5)cc4)c4cc5c6c(cccc6c4)C54c5cccc6cccc(c56)Cc5cccc6cccc4c56)cc3)cc21] | 72% |

-continued
| Ex. | Reactants | Product | Yield |
|---|---|---|---|
| H53 | S151<br>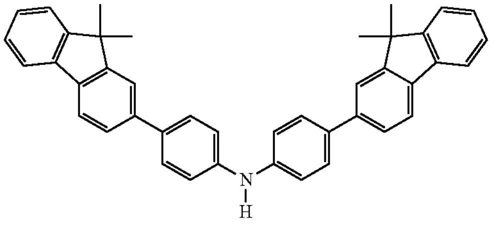<br>1221237-92-8 | 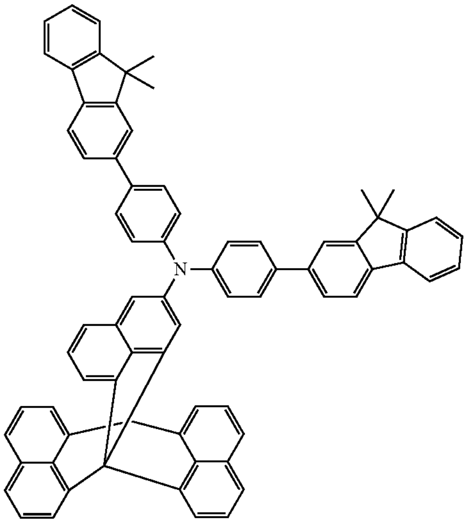 [SMILES: CC1(C)c2ccccc2-c2ccc(-c3ccc(N(c4ccc(-c5ccc6c(c5)C(C)(C)c5ccccc5-6)cc4)c4cc5c6c(cccc6c4)C54c5cccc6cccc(c56)Cc5cccc6cccc4c56)cc3)cc21] | 70% |
| H54 | S152<br>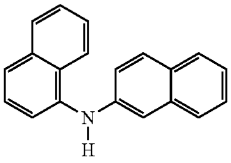<br>4669-06-1 | 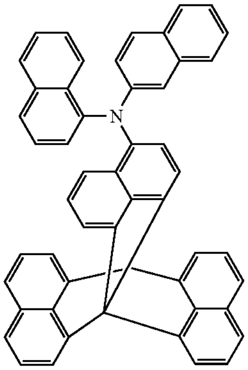 [SMILES: c1ccc2cc(N(c3cccc4ccccc34)c3ccc4c5c(cccc35)C43c4cccc5cccc(c45)Cc4cccc5cccc3c45)ccc2c1] | 67% |
| H55 | S152<br>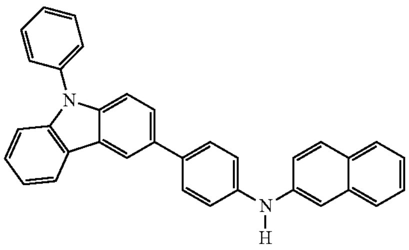<br>1370034-52-8 | 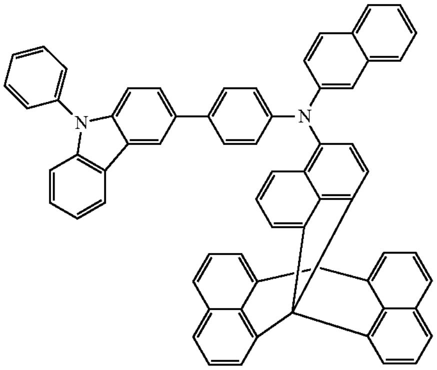 [SMILES: c1ccc(-n2c3ccccc3c3cc(-c4ccc(N(c5ccc6ccccc6c5)c5ccc6c7c(cccc57)C65c6cccc7cccc(c67)Cc6cccc7cccc5c67)cc4)ccc32)cc1] | 65% |

-continued
| Ex. | Reactants | Product | Yield |
|---|---|---|---|
| H56 | S152<br>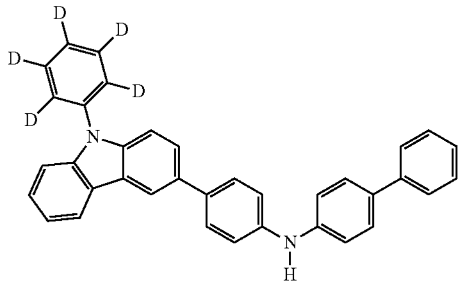<br>1345615-05-5 | 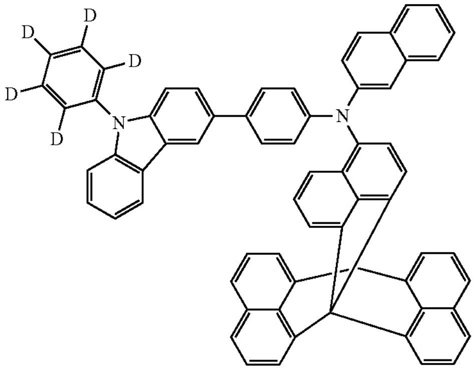 [SMILES: [2H]c1c([2H])c([2H])c(-n2c3ccccc3c3cc(-c4ccc(N(c5ccc6ccccc6c5)c5ccc6c7c(cccc57)C65c6cccc7cccc(c67)Cc6cccc7cccc5c67)cc4)ccc32)c([2H])c1[2H]] | 65% |
| H57 | S152<br>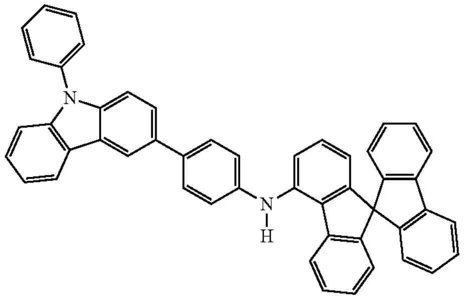<br>1933454-52-4 | 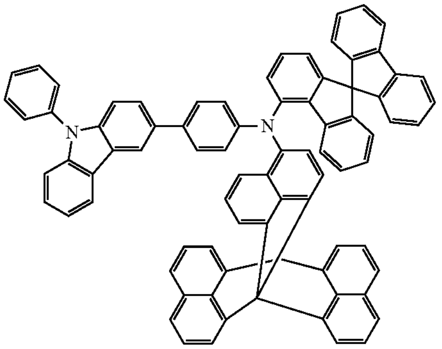 [SMILES: c1ccc(-n2c3ccccc3c3cc(-c4ccc(N(c5cccc6c5-c5ccccc5C65c6ccccc6-c6ccccc65)c5ccc6c7c(cccc57)C65c6cccc7cccc(c67)Cc6cccc7cccc5c67)cc4)ccc32)cc1] | 53% |
| H58 | S153<br>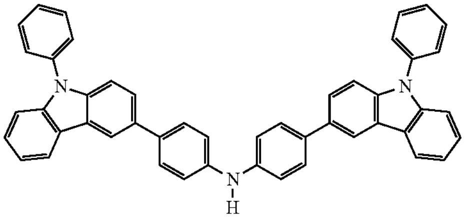<br>1245524-59-7 | 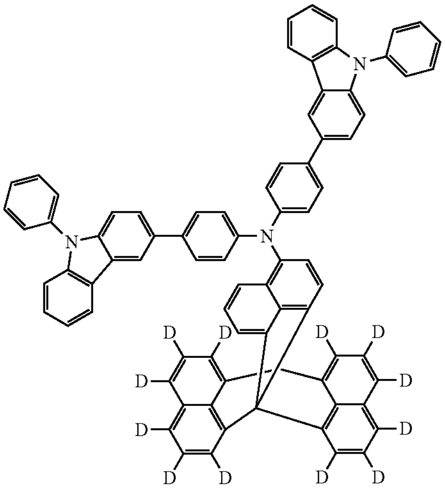 [SMILES: [2H]c1c([2H])c2c3c(c([2H])c([2H])c([2H])c3c1[2H])C1(c3cccc4c(N(c5ccc(-c6ccc7c(c6)c6ccccc6n7-c6ccccc6)cc5)c5ccc(-c6ccc7c(c6)c6ccccc6n7-c6ccccc6)cc5)ccc1c34)c1c([2H])c([2H])c([2H])c3c([2H])c([2H])c([2H])c(c13)C2] | 68% |

-continued
| Ex. | Reactants | Product | Yield |
| --- | --- | --- | --- |
| H59 | S153 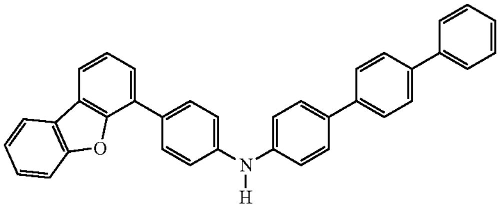 1228468-73-2 | 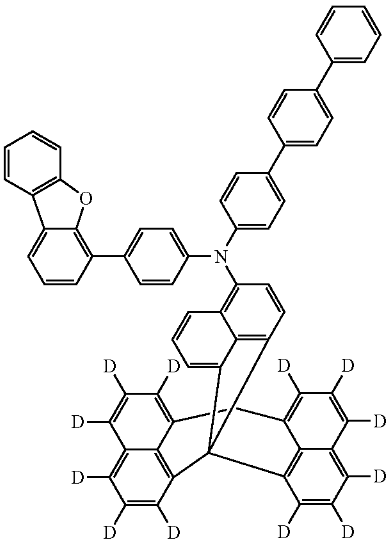 [SMILES: [2H]c1c([2H])c2c3c(c([2H])c([2H])c([2H])c3c1[2H])C1(c3cccc4c(N(c5ccc(-c6ccc(-c7ccccc7)cc6)cc5)c5ccc(-c6cccc7c6oc6ccccc67)cc5)ccc1c34)c1c([2H])c([2H])c([2H])c3c([2H])c([2H])c([2H])c(c13)C2] | 67% |
| H60 | S108 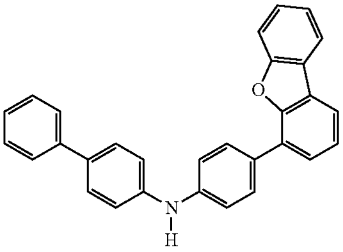 955959-89-4 | 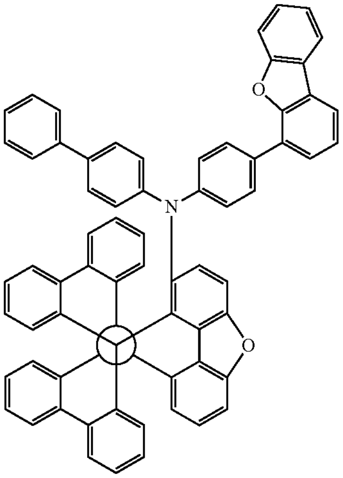 [SMILES: c1ccc(-c2ccc(N(c3ccc(-c4cccc5c4oc4ccccc45)cc3)c3ccc4oc5cccc6c5c4c3C34c5ccccc5-c5ccccc5C63c3ccccc3-c3ccccc34)cc2)cc1] | 37% |
| H61 | S109 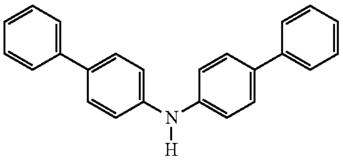 102113-98-4 | 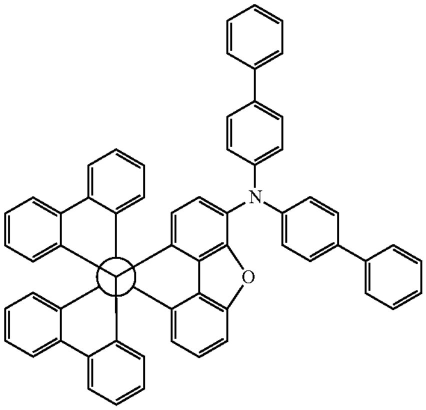 [SMILES: c1ccc(-c2ccc(N(c3ccc(-c4ccccc4)cc3)c3ccc4c5c3oc3cccc(c35)C35c6ccccc6-c6ccccc6C43c3ccccc3-c3ccccc35)cc2)cc1] | 87% |

Example H100

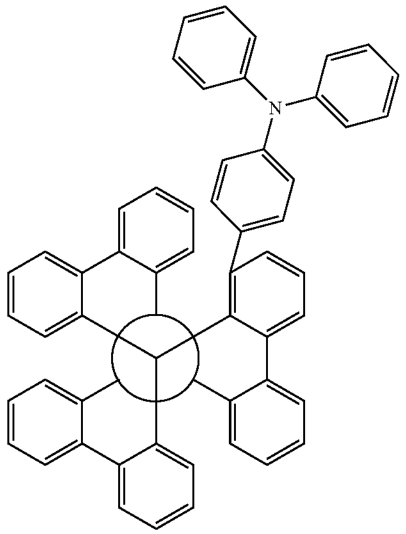 [SMILES: Cc1ccccc1-c1ccccc1C(c1ccccc1-c1ccccc1C)c1c(-c2ccc(N(c3ccccc3)c3ccccc3)cc2)cccc1-c1ccccc1C]

A mixture of 62.8 g (100 mmol) of S100, 37.1 g (110 mmol) of N,N-diphenylamino-4-(4,4,5,5-tetramethyl-1,3,2-dioxaborolan-2-yl)benzene [267221-88-5], 63.7 g (300 mmol) of tripotassium phosphate, 820 mg (2 mmol) of SPhos, 225 mg (1 mmol) of palladium acetate, 400 ml of toluene, 200 ml of dioxane and 400 ml of water is heated under reflux for 20 h. 1 ml of hydrazine hydrate is added and the mixture is heated under reflux for 1 h. The mixture is left to cool to 60° C., the aqueous phase is separated off, and the organic phase is washed twice with 300 ml each time of water and once with 300 ml of saturated sodium chloride solution, and filtered while still hot through a Celite bed in the form of a toluene slurry. The filtrate is concentrated to about 100 ml and then 200 ml of methanol are added to the filtrate while hot with good stirring. The mixture is left to cool while stirring, and the crystallized product is filtered off and washed three times with 100 ml each time of methanol. Further purification is effected by hot extraction five times with butyl acetate (amount initially charged 250 ml) and subsequent double fractional sublimation under reduced pressure (T about 310° C., p about $10^{-5}$ mbar). Yield: 31.9 g (44 mmol), 44%; purity: about 99.9% by HPLC.

In an analogous manner, it is possible to prepare the following compounds:

| Ex. | Reactants | Product | Yield |
| --- | --- | --- | --- |
| H101 | S100 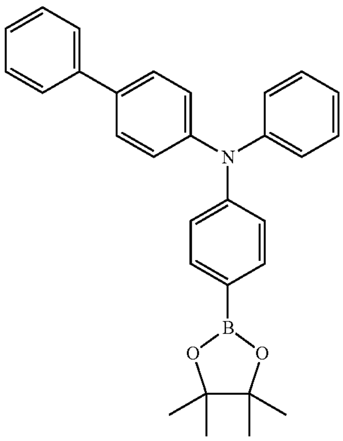 1338803-75-0 | 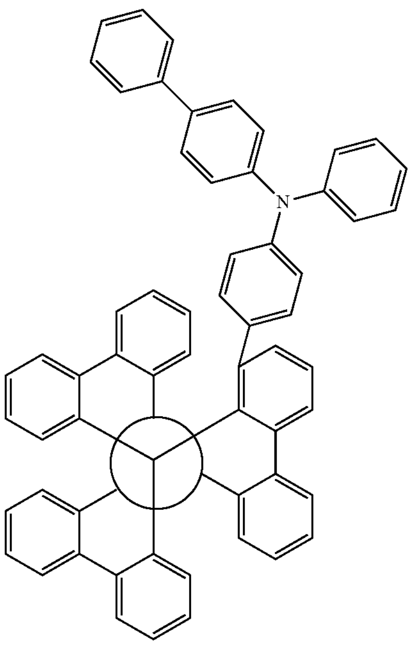 [SMILES: Cc1ccccc1-c1ccccc1C(c1ccccc1-c1ccccc1C)c1c(-c2ccc(N(c3ccccc3)c3ccc(-c4ccccc4)cc3)cc2)cccc1-c1ccccc1C] | 40% |

-continued
| Ex. | Reactants | Product | Yield |
| --- | --- | --- | --- |
| H102 | S100 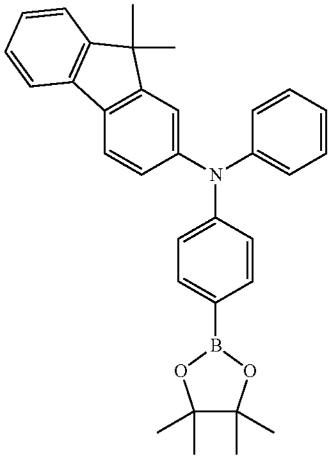 950986-07-9 | 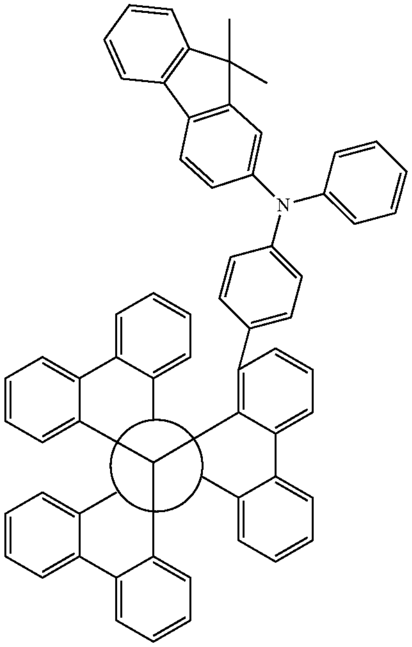 [SMILES: Cc1ccccc1-c1ccccc1C(c1ccccc1-c1ccccc1C)c1c(-c2ccc(N(c3ccccc3)c3ccc4c(c3)C(C)(C)c3ccccc3-4)cc2)cccc1-c1ccccc1C] | 45% |
| H103 | S101 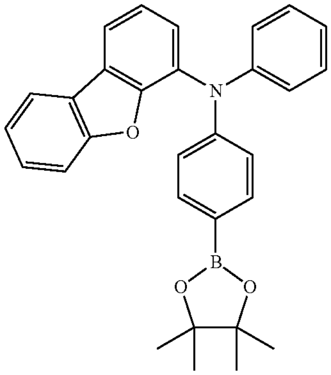 1640132-91-7 | 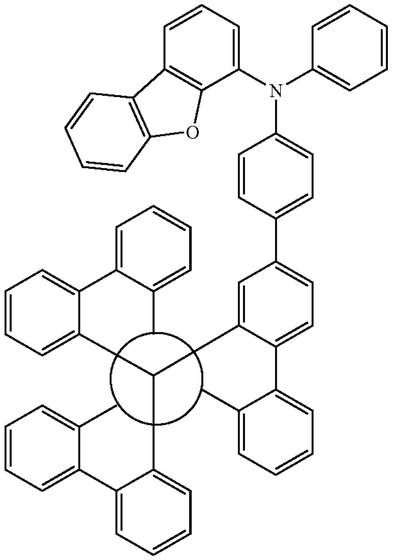 [SMILES: Cc1ccccc1-c1ccccc1C(c1ccccc1-c1ccccc1C)c1cc(-c2ccc(N(c3ccccc3)c3cccc4c3oc3ccccc34)cc2)ccc1-c1ccccc1C] | 73% |

-continued
| Ex. | Reactants | Product | Yield |
|---|---|---|---|
| H104 | S101<br>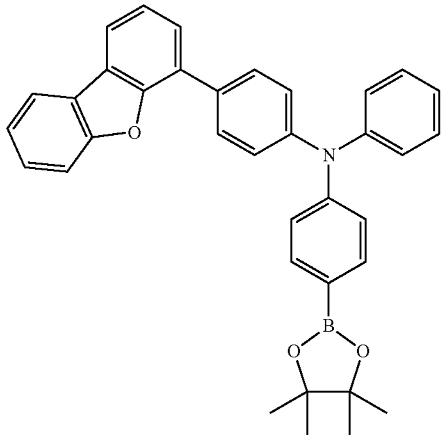<br>1848986-77-5 | 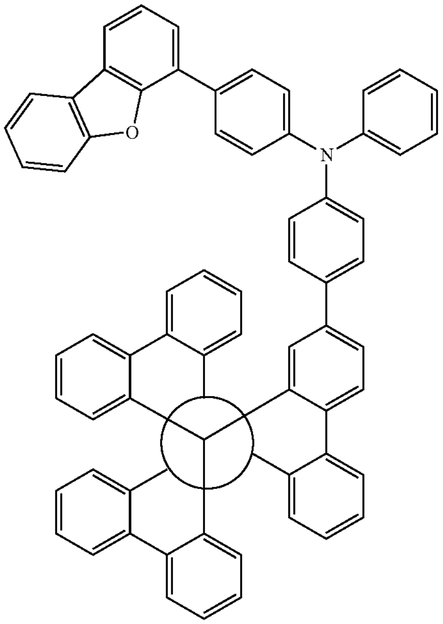 [SMILES: Cc1ccccc1-c1ccccc1C(c1ccccc1-c1ccccc1C)c1cc(-c2ccc(N(c3ccccc3)c3ccc(-c4cccc5c4oc4ccccc45)cc3)cc2)ccc1-c1ccccc1C] | 70% |
| H105 | S101<br>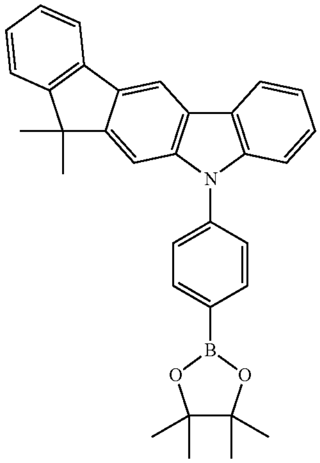<br>1809075-56-6 | 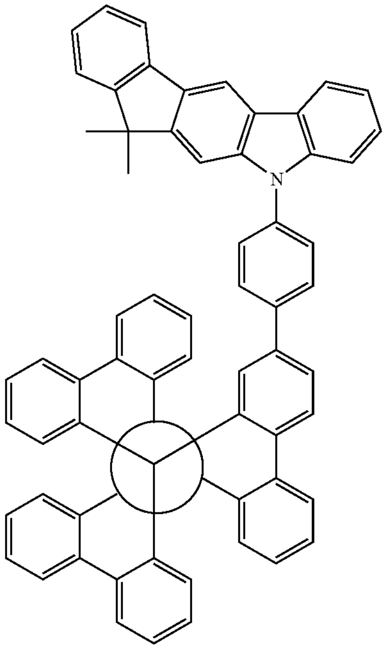 [SMILES: Cc1ccccc1-c1ccccc1C(c1ccccc1-c1ccccc1C)c1cc(-c2ccc(-n3c4ccccc4c4cc5c(cc43)C(C)(C)c3ccccc3-5)cc2)ccc1-c1ccccc1C] | 70% |

-continued
| Ex. | Reactants | Product | Yield |
|---|---|---|---|
| H106 | S102 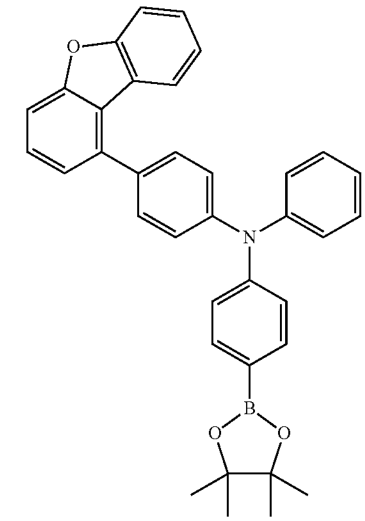 1644394-88-6 | 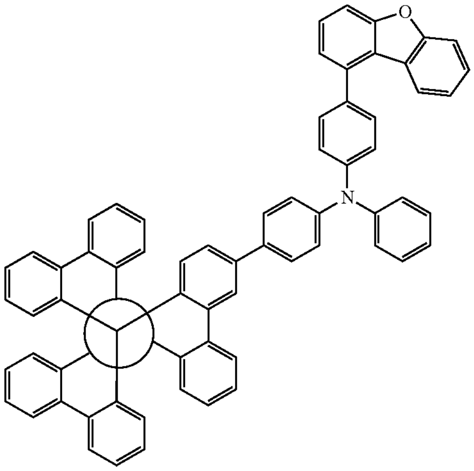 [SMILES: Cc1ccccc1-c1ccccc1C(c1ccccc1-c1ccccc1C)c1ccc(-c2ccc(N(c3ccccc3)c3ccc(-c4cccc5oc6ccccc6c45)cc3)cc2)cc1-c1ccccc1C] | 74% |
| H107 | S102 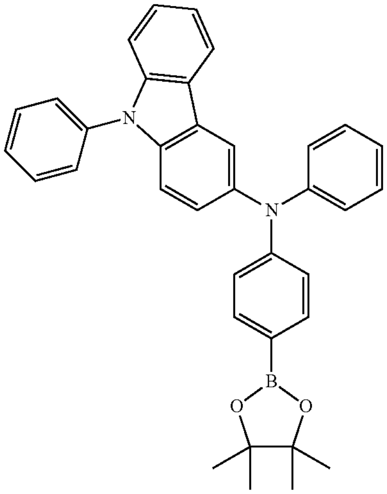 1325614-27-4 | 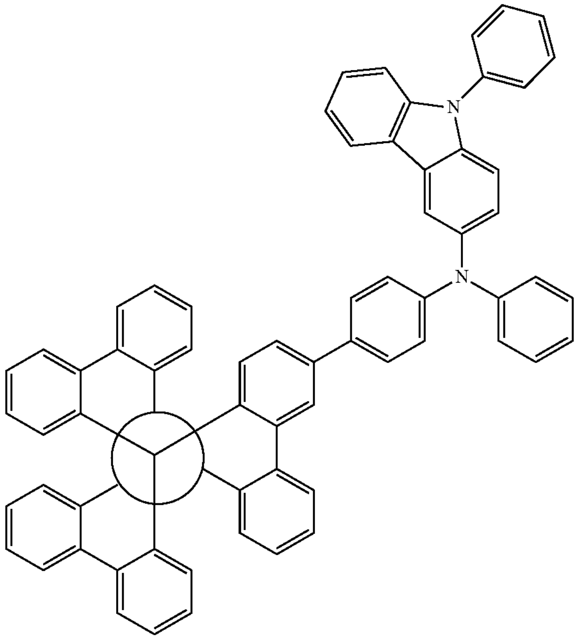 [SMILES: Cc1ccccc1-c1ccccc1C(c1ccccc1-c1ccccc1C)c1ccc(-c2ccc(N(c3ccccc3)c3ccc4c(c3)c3ccccc3n4-c3ccccc3)cc2)cc1-c1ccccc1C] | 72% |

-continued
| Ex. | Reactants | Product | Yield |
| --- | --- | --- | --- |
| H108 | S102<br>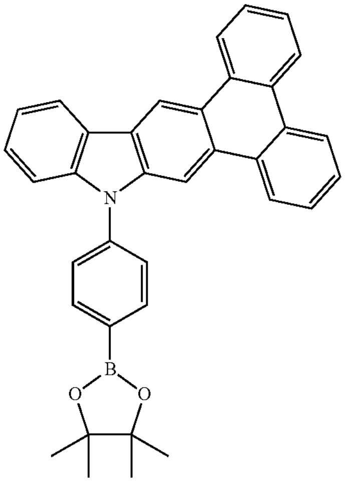<br>1819346-61-6 | 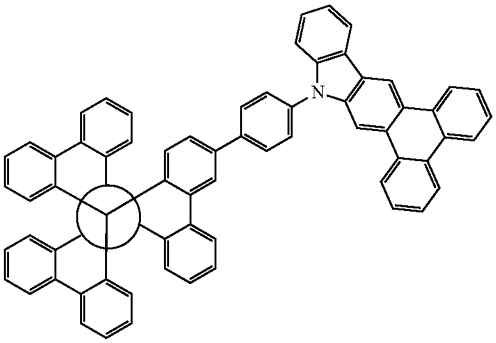 [SMILES: Cc1ccccc1-c1ccccc1C(c1ccccc1-c1ccccc1C)c1ccc(-c2ccc(-n3c4ccccc4c4cc5c6ccccc6c6ccccc6c5cc43)cc2)cc1-c1ccccc1C] | 70% |
| H109 | S103<br>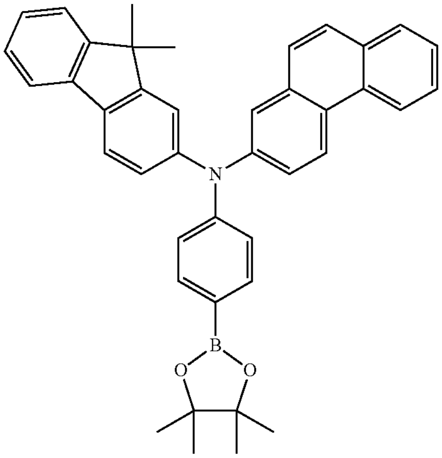<br>1818202-45-7 | 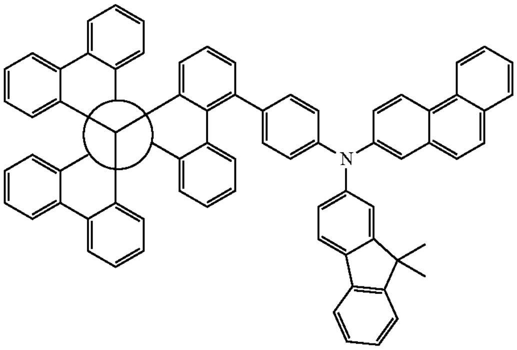 [SMILES: Cc1ccccc1-c1ccccc1C(c1ccccc1-c1ccccc1C)c1cccc(-c2ccc(N(c3ccc4c(c3)C(C)(C)c3ccccc3-4)c3ccc4c(ccc5ccccc54)c3)cc2)c1-c1ccccc1C] | 58% |
| H110 | S103<br>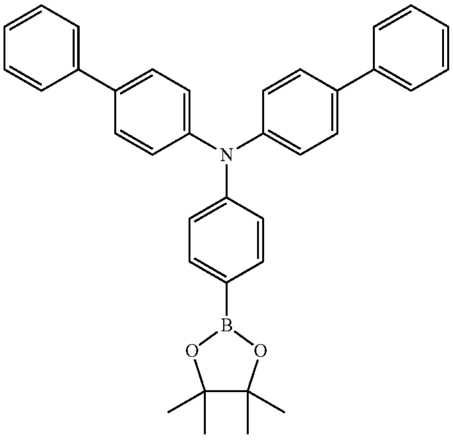<br>952431-30-0 | 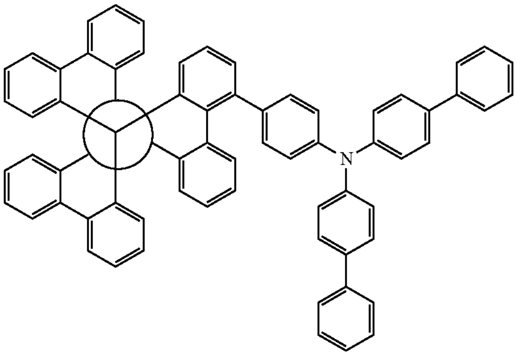 [SMILES: Cc1ccccc1-c1ccccc1C(c1ccccc1-c1ccccc1C)c1cccc(-c2ccc(N(c3ccc(-c4ccccc4)cc3)c3ccc(-c4ccccc4)cc3)cc2)c1-c1ccccc1C] | 63% |

-continued
| Ex. | Reactants | Product | Yield |
| --- | --- | --- | --- |
| H111 | S103 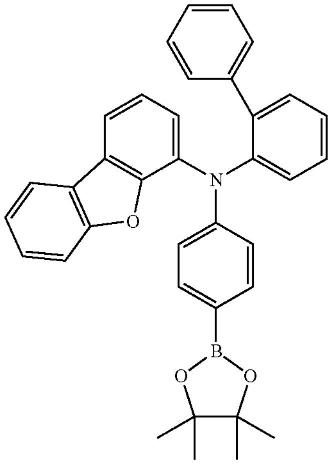 1809185-82-7 | 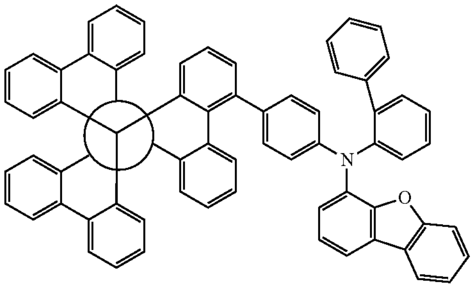 [SMILES: Cc1ccccc1-c1ccccc1C(c1ccccc1-c1ccccc1C)c1cccc(-c2ccc(N(c3ccccc3-c3ccccc3)c3cccc4c3oc3ccccc34)cc2)c1-c1ccccc1C] | 60% |
| H112 | S103 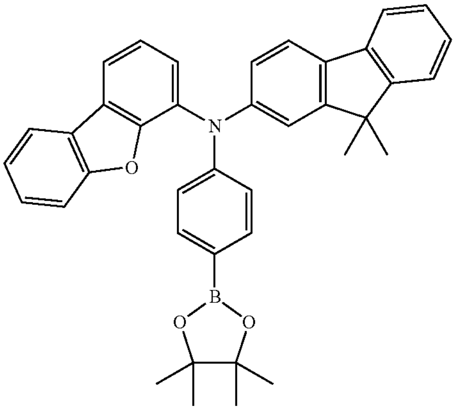 1228149-60-7 | 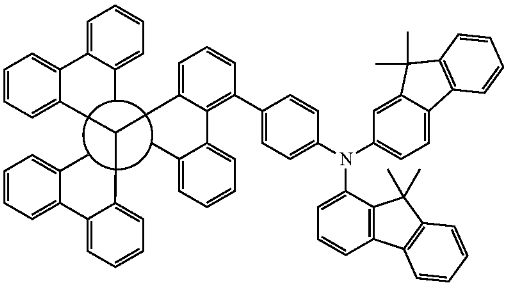 [SMILES: Cc1ccccc1-c1ccccc1C(c1ccccc1-c1ccccc1C)c1cccc(-c2ccc(N(c3ccc4c(c3)C(C)(C)c3ccccc3-4)c3cccc4c3C(C)(C)c3ccccc3-4)cc2)c1-c1ccccc1C] | 61% |
| H113 | S103 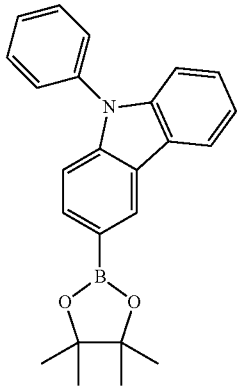 1126522-69-7 | 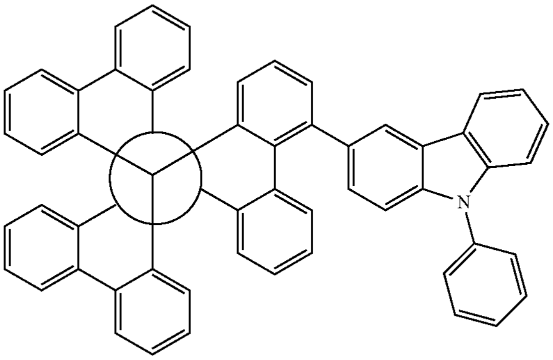 [SMILES: Cc1ccccc1-c1ccccc1C(c1ccccc1-c1ccccc1C)c1cccc(-c2ccc3c(c2)c2ccccc2n3-c2ccccc2)c1-c1ccccc1C] | 66% |

-continued
| Ex. | Reactants | Product | Yield |
| --- | --- | --- | --- |
| H114 | S103<br>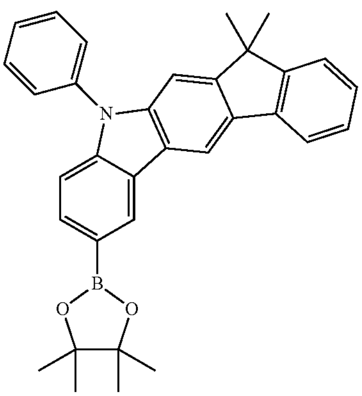<br>1357150-79-8 | 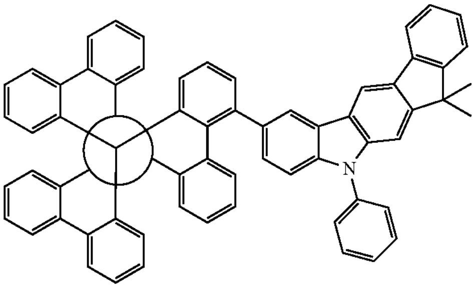 [SMILES: Cc1ccccc1-c1ccccc1C(c1ccccc1-c1ccccc1C)c1cccc(-c2ccc3c(c2)c2cc4c(cc2n3-c2ccccc2)C(C)(C)c2ccccc2-4)c1-c1ccccc1C] | 63% |
| H115 | S103<br>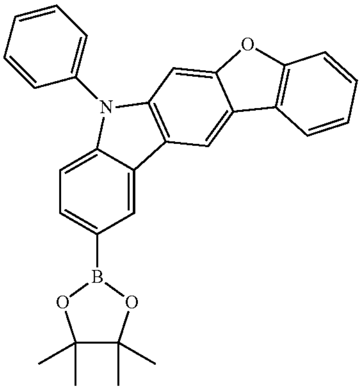<br>1993414-80-4 | 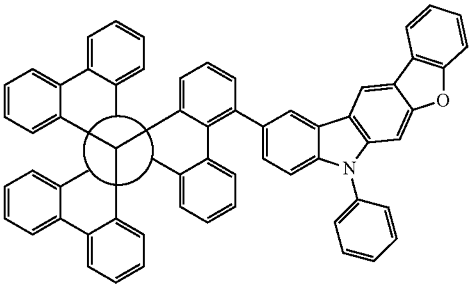 [SMILES: Cc1ccccc1-c1ccccc1C(c1ccccc1-c1ccccc1C)c1cccc(-c2ccc3c(c2)c2cc4c(cc2n3-c2ccccc2)oc2ccccc24)c1-c1ccccc1C] | 58% |
| H116 | S103<br>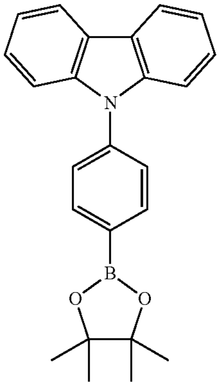<br>785051-54-9 | 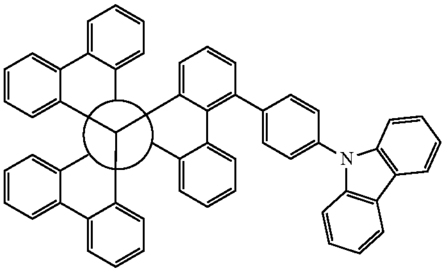 [SMILES: Cc1ccccc1-c1ccccc1C(c1ccccc1-c1ccccc1C)c1cccc(-c2ccc(-n3c4ccccc4c4ccccc43)cc2)c1-c1ccccc1C] | 68% |

-continued
| Ex. | Reactants | Product | Yield |
| --- | --- | --- | --- |
| H117 | S103<br>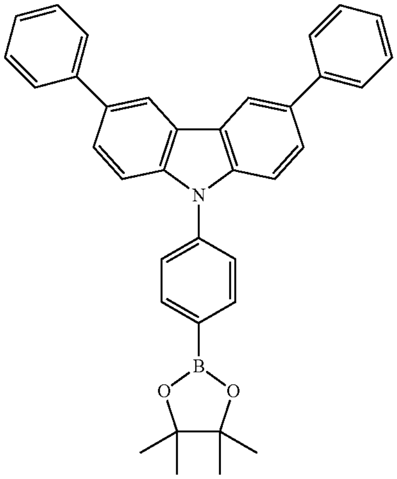<br>1149804-38-5 | 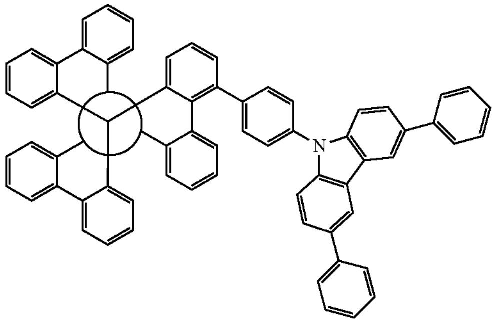 [SMILES: Cc1ccccc1-c1ccccc1C(c1ccccc1-c1ccccc1C)c1cccc(-c2ccc(-n3c4ccc(-c5ccccc5)cc4c4cc(-c5ccccc5)ccc43)cc2)c1-c1ccccc1C] | 65% |
| H118 | S103<br>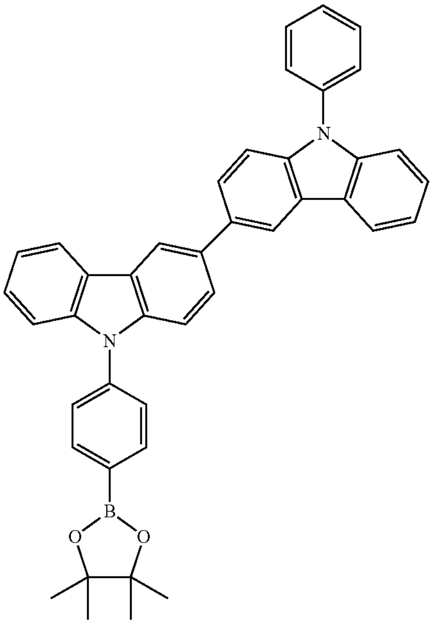<br>1637465-85-0 | 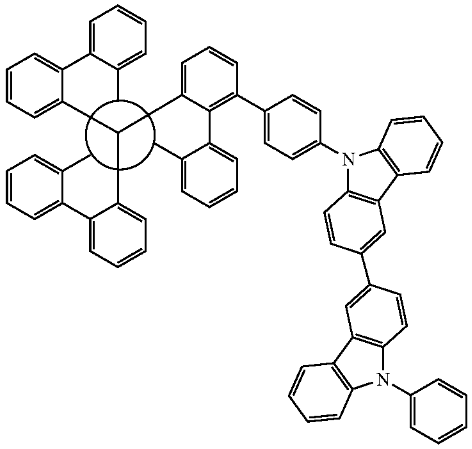 [SMILES: Cc1ccccc1-c1ccccc1C(c1ccccc1-c1ccccc1C)c1cccc(-c2ccc(-n3c4ccccc4c4cc(-c5ccc6c(c5)c5ccccc5n6-c5ccccc5)ccc43)cc2)c1-c1ccccc1C] | 66% |

-continued
| Ex. | Reactants | Product | Yield |
| --- | --- | --- | --- |
| H119 | S103 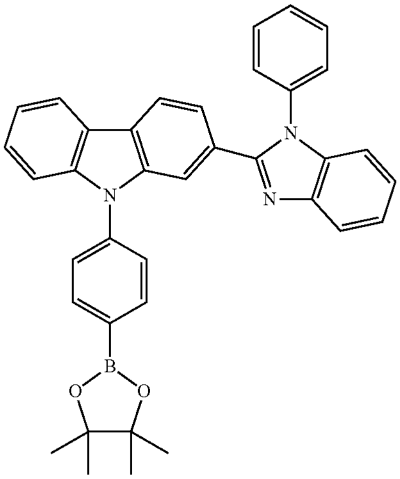 1254376-01-6 | 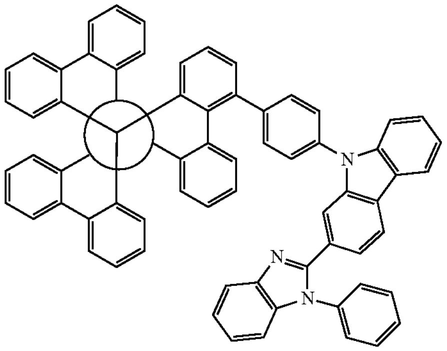 [SMILES: Cc1ccccc1-c1ccccc1C(c1ccccc1-c1ccccc1C)c1cccc(-c2ccc(-n3c4ccccc4c4ccc(-c5nc6ccccc6n5-c5ccccc5)cc43)cc2)c1-c1ccccc1C] | 64% |
| H120 | S104 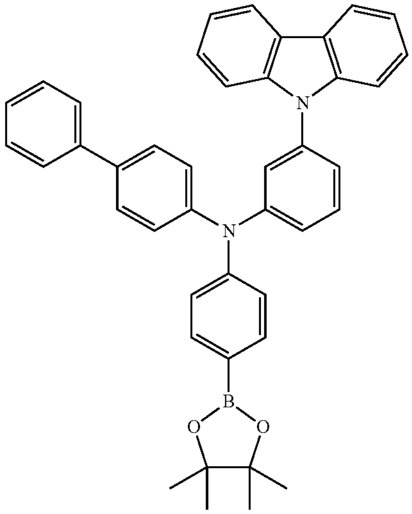 1228149-60-7 | 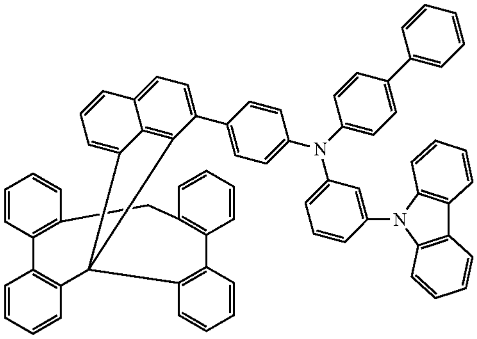 [SMILES: c1ccc(-c2ccc(N(c3ccc(-c4ccc5cccc6c5c4C64c5ccccc5-c5ccccc5Cc5ccccc5-c5ccccc54)cc3)c3cccc(-n4c5ccccc5c5ccccc54)c3)cc2)cc1] | 38% |

-continued
| Ex. | Reactants | Product | Yield |
| --- | --- | --- | --- |
| H121 | S104<br>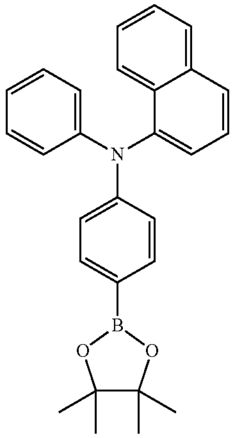<br>528610-01-7 | 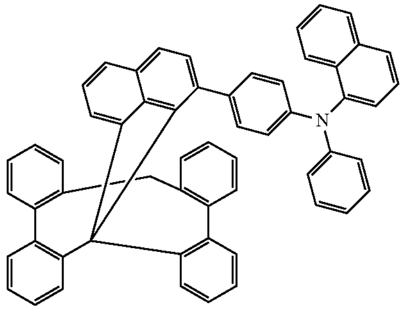 [SMILES: c1ccc(N(c2ccc(-c3ccc4cccc5c4c3C53c4ccccc4-c4ccccc4Cc4ccccc4-c4ccccc43)cc2)c2cccc3ccccc23)cc1] | 41% |
| H122 | S105<br>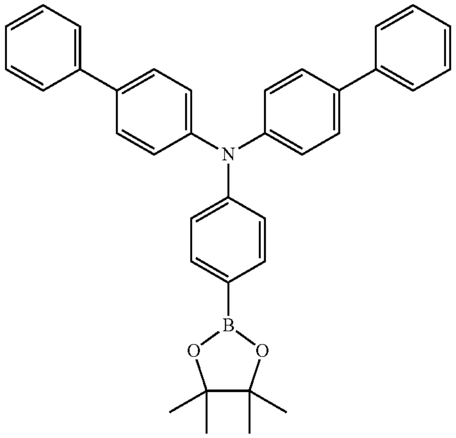<br>952431-30-0 | 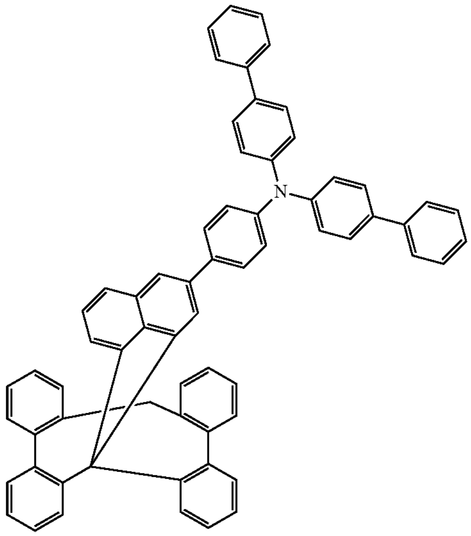 [SMILES: c1ccc(-c2ccc(N(c3ccc(-c4ccccc4)cc3)c3ccc(-c4cc5c6c(cccc6c4)C54c5ccccc5-c5ccccc5Cc5ccccc5-c5ccccc54)cc3)cc2)cc1] | 70% |
| H123 | S105<br>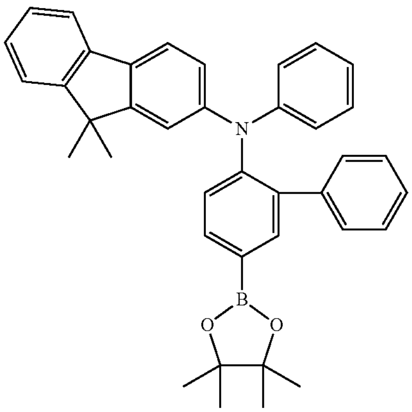<br>1877345-82-8 | 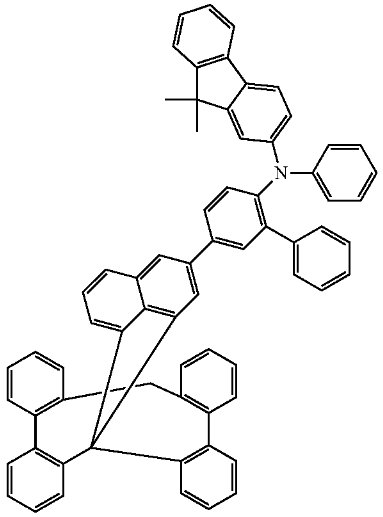 [SMILES: CC1(C)c2ccccc2-c2ccc(N(c3ccccc3)c3ccc(-c4cc5c6c(cccc6c4)C54c5ccccc5-c5ccccc5Cc5ccccc5-c5ccccc54)cc3-c3ccccc3)cc21] | 68% |

-continued
| Ex. | Reactants | Product | Yield |
|---|---|---|---|
| H124 | S106<br>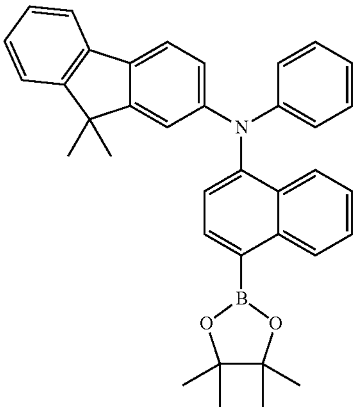<br>1639460-55-1 | 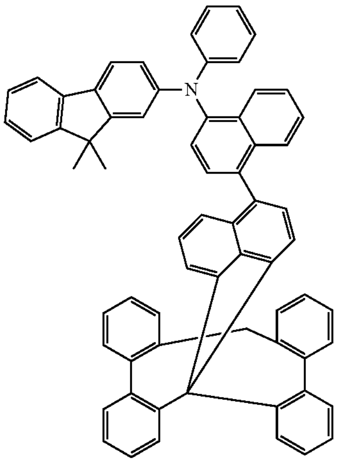 [SMILES: CC1(C)c2ccccc2-c2ccc(N(c3ccccc3)c3ccc(-c4ccc5c6c(cccc46)C54c5ccccc5-c5ccccc5Cc5ccccc5-c5ccccc54)c4ccccc34)cc21] | 73% |
| H125 | S106<br>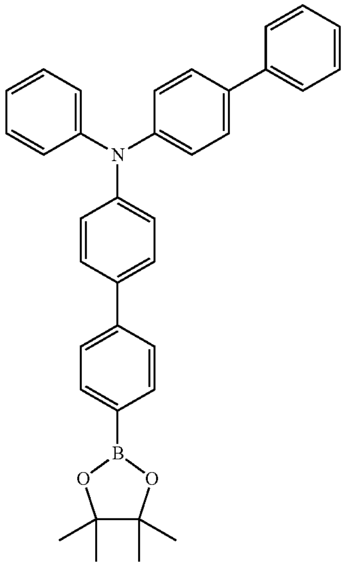<br>1268622-36-1 | 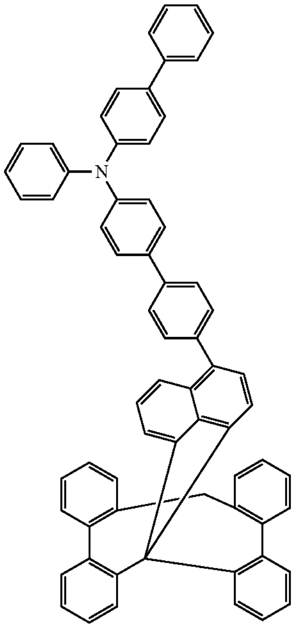 [SMILES: c1ccc(-c2ccc(N(c3ccccc3)c3ccc(-c4ccc(-c5ccc6c7c(cccc57)C65c6ccccc6-c6ccccc6Cc6ccccc6-c6ccccc65)cc4)cc3)cc2)cc1] | 70% |

-continued
| Ex. | Reactants | Product | Yield |
|---|---|---|---|
| H126 | S107<br>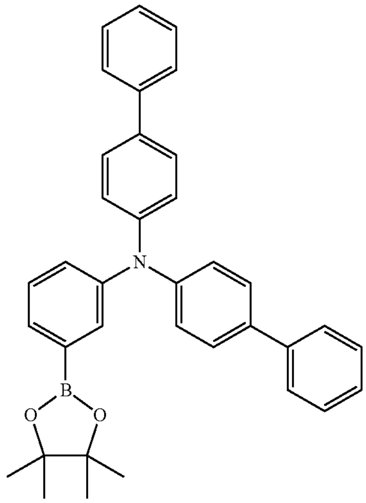<br>952431-32-2 | 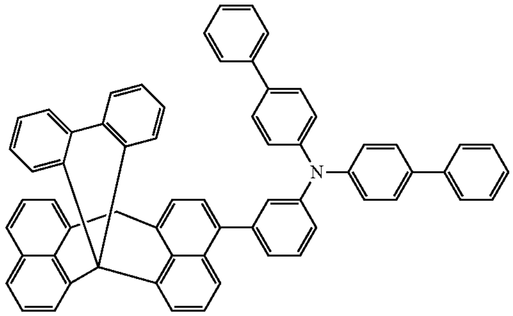 [SMILES: c1ccc(-c2ccc(N(c3ccc(-c4ccccc4)cc3)c3cccc(-c4ccc5c6c(cccc46)C4(c6ccccc6-c6ccccc64)c4cccc6cccc(c46)C5)c3)cc2)cc1] | 67% |
| H127 | S151<br>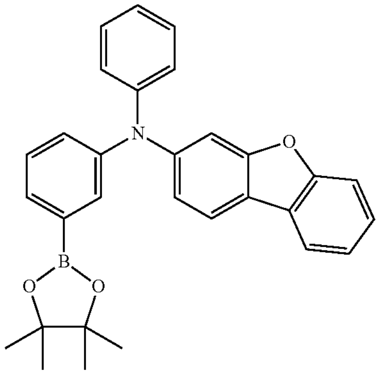<br>1877345-91-9 | 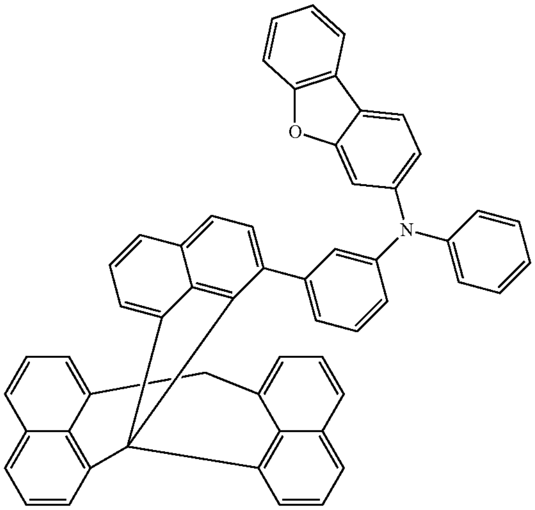 [SMILES: c1ccc(N(c2cccc(-c3ccc4cccc5c4c3C53c4cccc5cccc(c45)Cc4cccc5cccc3c45)c2)c2ccc3c(c2)oc2ccccc23)cc1] | 65% |

-continued
| Ex. | Reactants | Product | Yield |
|---|---|---|---|
| H128 | S152<br>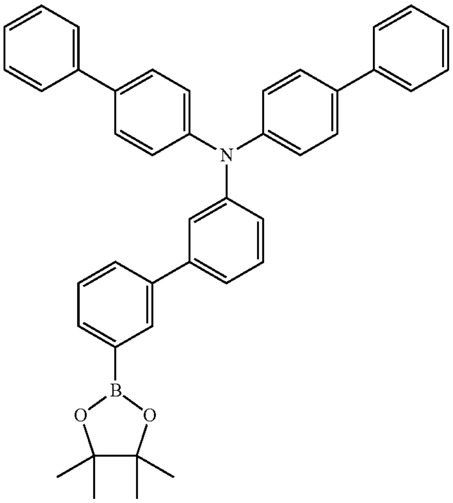<br>1644054-58-9 | 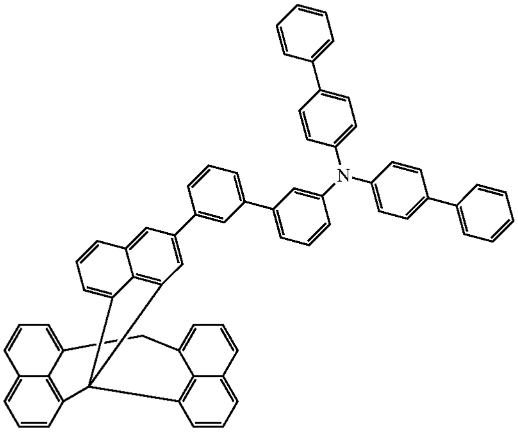 [SMILES: c1ccc(-c2ccc(N(c3ccc(-c4ccccc4)cc3)c3cccc(-c4cccc(-c5cc6c7c(cccc7c5)C65c6cccc7cccc(c67)Cc6cccc7cccc5c67)c4)c3)cc2)cc1] | 69% |
| H129 | S153<br>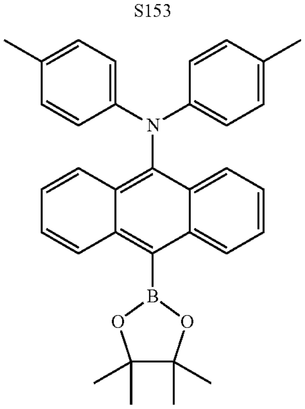<br>922519-00-4 | 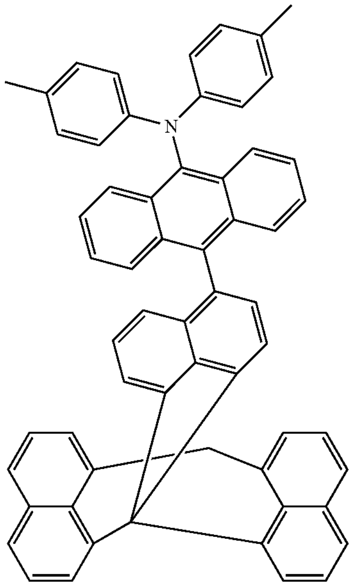 [SMILES: Cc1ccc(N(c2ccc(C)cc2)c2c3ccccc3c(-c3ccc4c5c(cccc35)C43c4cccc5cccc(c45)Cc4cccc5cccc3c45)c3ccccc23)cc1] | 49% |

-continued
| Ex. | Reactants | Product | Yield |
| --- | --- | --- | --- |
| H130 | S108<br>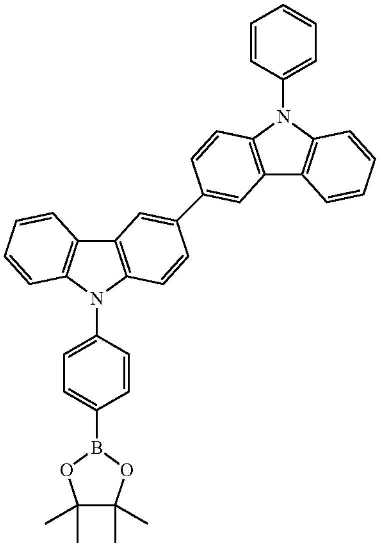<br>1637465-85-0 | 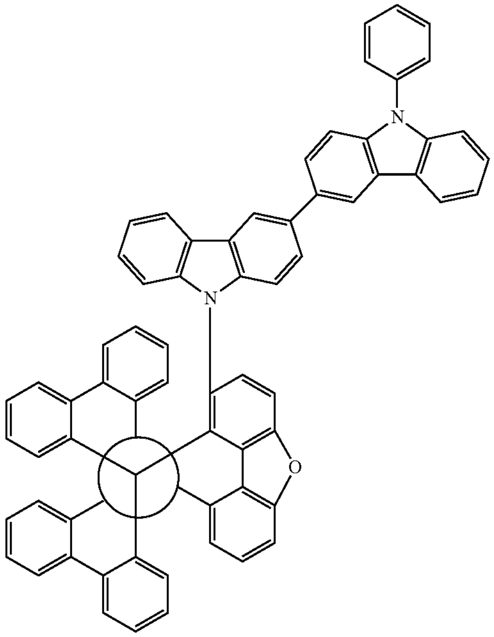 [SMILES: Cc1ccccc1-c1ccccc1C(c1ccccc1-c1ccccc1C)c1c(-n2c3ccccc3c3cc(-c4ccc5c(c4)c4ccccc4n5-c4ccccc4)ccc32)ccc2oc3cccc(C)c3c12] | 33% |
| H131 | S109<br>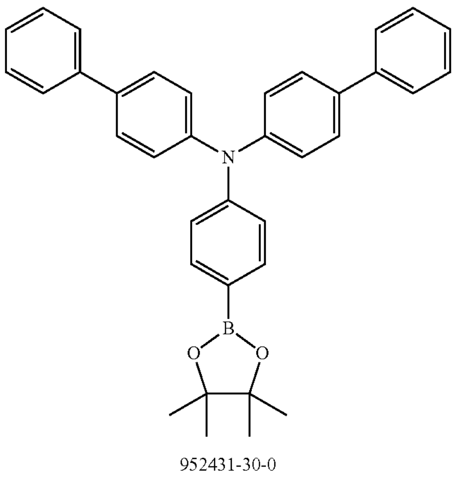<br>952431-30-0 | 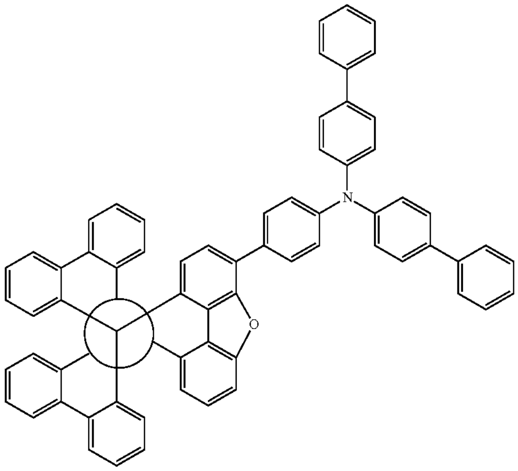 [SMILES: Cc1ccccc1-c1ccccc1C(c1ccccc1-c1ccccc1C)c1ccc(-c2ccc(N(c3ccc(-c4ccccc4)cc3)c3ccc(-c4ccccc4)cc3)cc2)c2oc3cccc(C)c3c12] | 71% |

Example E1

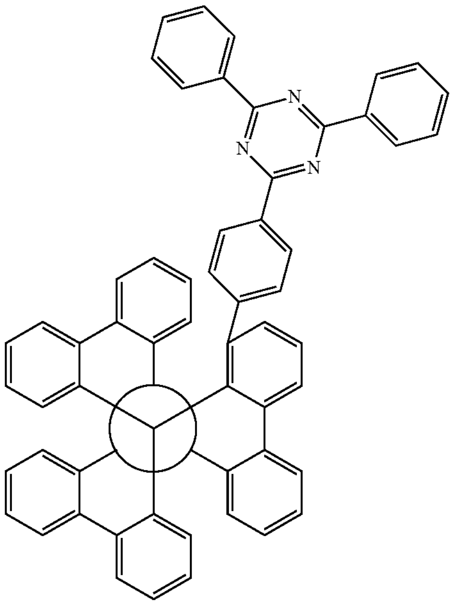 [SMILES: Cc1ccccc1-c1ccccc1C(c1ccccc1-c1ccccc1C)c1c(-c2ccc(-c3nc(-c4ccccc4)nc(-c4ccccc4)n3)cc2)cccc1-c1ccccc1C]

A mixture of 62.8 g (100 mmol) of S100, 47.9 g (110 mmol) of 2,4-diphenyl-6-[4-(4,4,5,5-tetramethyl-1,3,2-dioxaborolan-2-yl)phenyl]-1,3,5-triazine [1219956-23-6], 63.7 g (300 mmol) of tripotassium phosphate, 820 mg (2 mmol) of SPhos, 225 mg (1 mmol) of palladium acetate, 400 ml of toluene, 200 ml of dioxane and 400 ml of water is heated under reflux for 20 h. The mixture is left to cool to 60° C., the aqueous phase is separated off, and the organic phase is washed twice with 300 ml each time of water and once with 300 ml of saturated sodium chloride solution, and filtered while still hot through a Celite bed in the form of a toluene slurry. The filtrate is concentrated to about 100 ml and then 200 ml of methanol are added to the filtrate while hot with good stirring. The mixture is left to cool while stirring, and the crystallized product is filtered off and washed three times with 100 ml each time of methanol. Further purification is effected by hot extraction five times with toluene (amount initially charged 250 ml) and subsequent double fractional sublimation under reduced pressure (T about 320° C., p about $10^{-5}$ mbar). Yield: 38.6 g (49 mmol), 49%; purity: about 99.9% by HPLC.

In an analogous manner, its possible to pre are the following compounds:

| Ex | Reactants | Product | Yield |
|---|---|---|---|
| E2 | S100 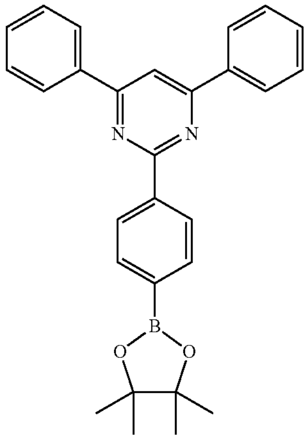 1613163-88-4 | 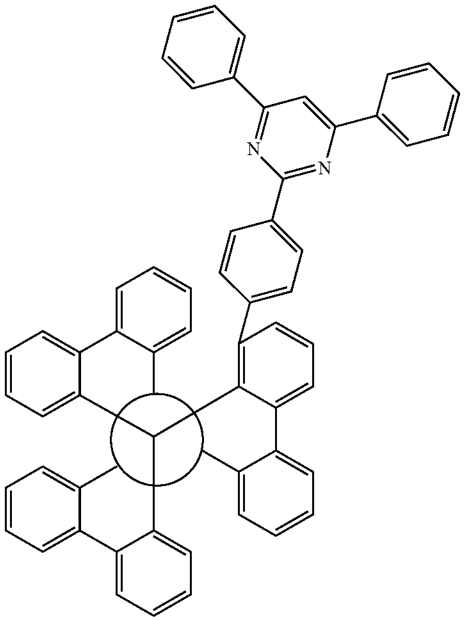 [SMILES: Cc1ccccc1-c1ccccc1C(c1ccccc1-c1ccccc1C)c1c(-c2ccc(-c3nc(-c4ccccc4)cc(-c4ccccc4)n3)cc2)cccc1-c1ccccc1C] | 46% |

-continued
| Ex | Reactants | Product | Yield |
| --- | --- | --- | --- |
| E3 | S101<br>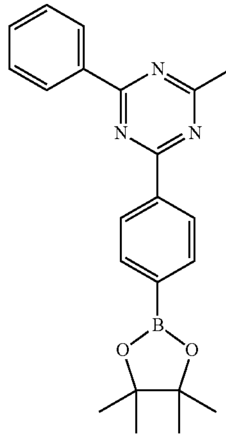<br>1219956-23-6 | 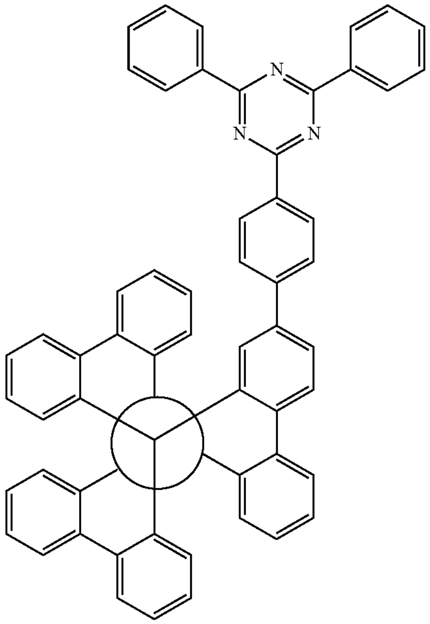 [SMILES: Cc1ccccc1-c1ccccc1C(c1ccccc1-c1ccccc1C)c1cc(-c2ccc(-c3nc(-c4ccccc4)nc(-c4ccccc4)n3)cc2)ccc1-c1ccccc1C] | 72% |
| E4 | S101<br>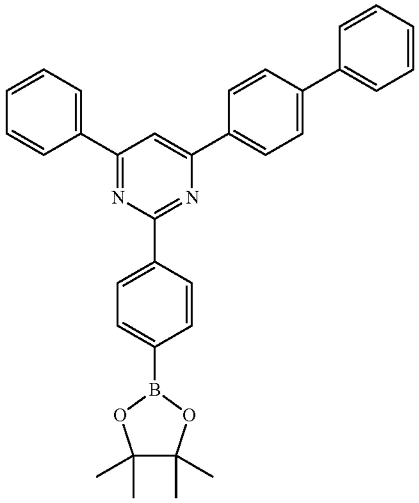<br>1689538-49-5 | 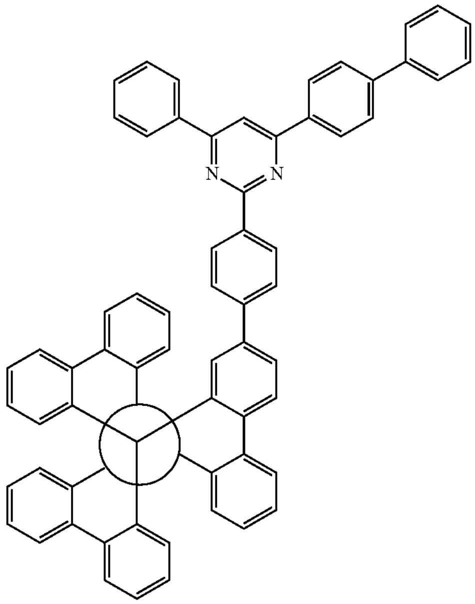 [SMILES: Cc1ccccc1-c1ccccc1C(c1ccccc1-c1ccccc1C)c1cc(-c2ccc(-c3nc(-c4ccccc4)cc(-c4ccc(-c5ccccc5)cc4)n3)cc2)ccc1-c1ccccc1C] | 70% |

-continued
| Ex | Reactants | Product | Yield |
|---|---|---|---|
| E5 | S101<br>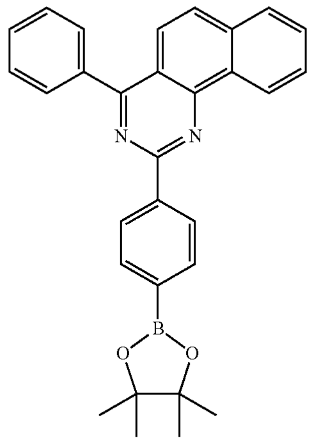<br>1616841-80-5 | 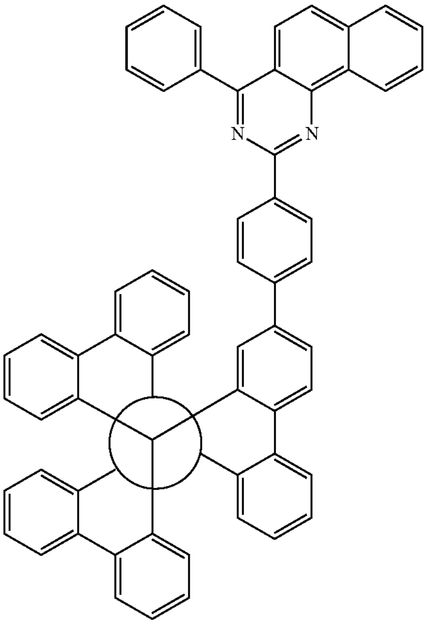 [SMILES: Cc1ccccc1-c1ccccc1C(c1ccccc1-c1ccccc1C)c1cc(-c2ccc(-c3nc(-c4ccccc4)c4ccc5ccccc5c4n3)cc2)ccc1-c1ccccc1C] | 68% |
| E6 | S102<br>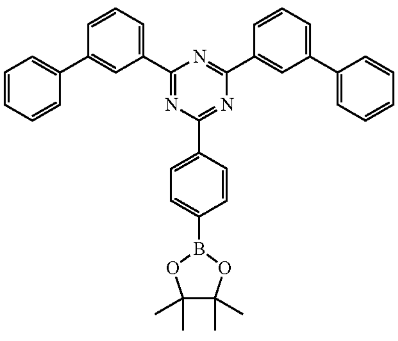<br>1835206-27-3 | 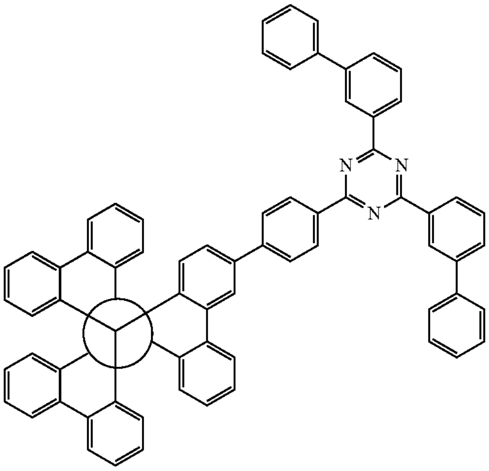 [SMILES: Cc1ccccc1-c1ccccc1C(c1ccccc1-c1ccccc1C)c1ccc(-c2ccc(-c3nc(-c4cccc(-c5ccccc5)c4)nc(-c4cccc(-c5ccccc5)c4)n3)cc2)cc1-c1ccccc1C] | 75% |

-continued
| Ex | Reactants | Product | Yield |
|---|---|---|---|
| E7 | S102<br>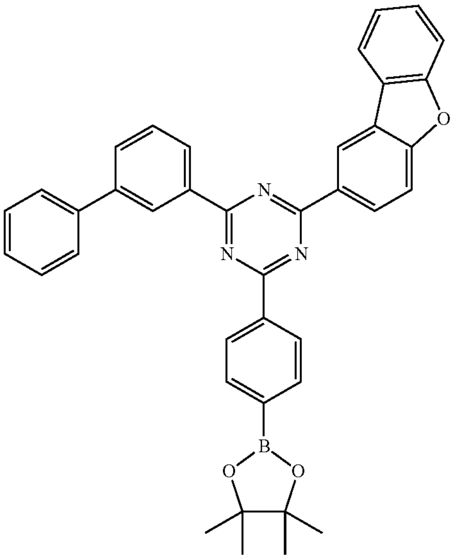<br>1835206-50-2 | 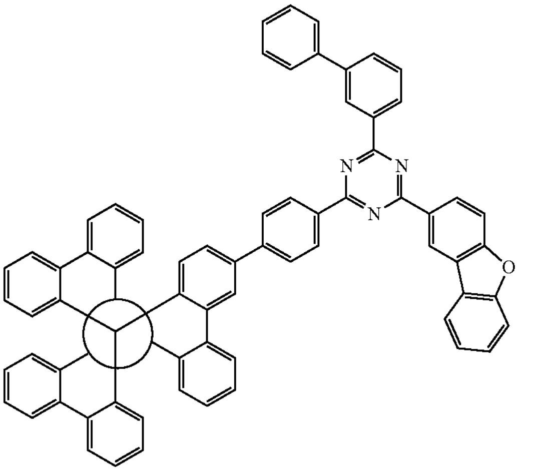 [SMILES: Cc1ccccc1-c1ccccc1C(c1ccccc1-c1ccccc1C)c1ccc(-c2ccc(-c3nc(-c4cccc(-c5ccccc5)c4)nc(-c4ccc5oc6ccccc6c5c4)n3)cc2)cc1-c1ccccc1C] | 77 & |
| E8 | S103<br>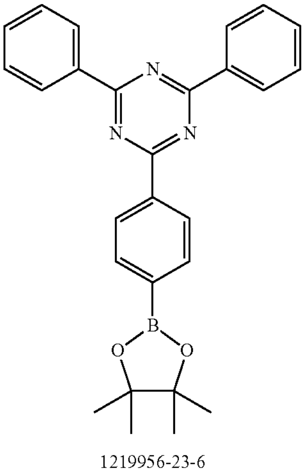<br>1219956-23-6 | 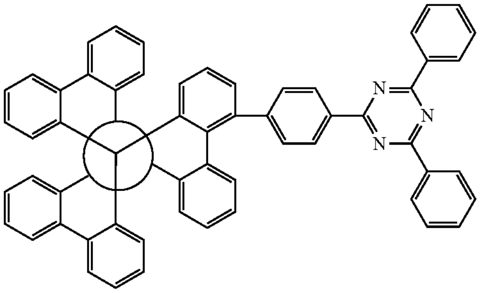 [SMILES: Cc1ccccc1-c1ccccc1C(c1ccccc1-c1ccccc1C)c1cccc(-c2ccc(-c3nc(-c4ccccc4)nc(-c4ccccc4)n3)cc2)c1-c1ccccc1C] | 64% |

-continued
| Ex | Reactants | Product | Yield |
| --- | --- | --- | --- |
| E9 | S103 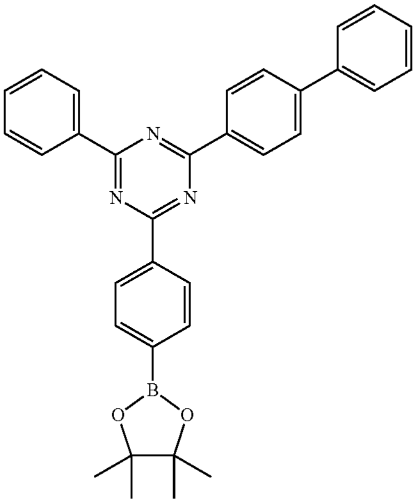 1689538-49-5 | 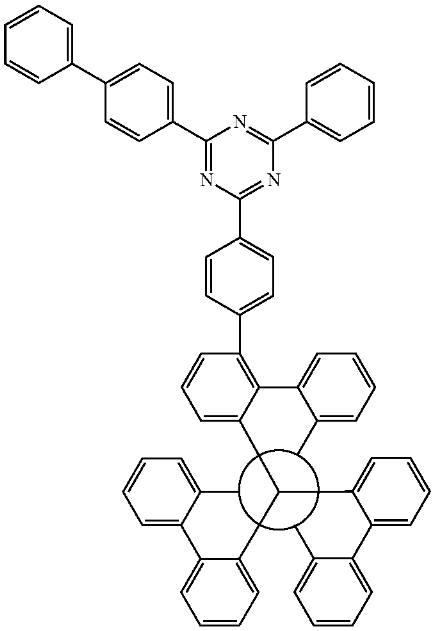 [SMILES: Cc1ccccc1-c1ccccc1C(c1ccccc1-c1ccccc1C)c1cccc(-c2ccc(-c3nc(-c4ccccc4)nc(-c4ccc(-c5ccccc5)cc4)n3)cc2)c1-c1ccccc1C] | 67% |
| E10 | S103 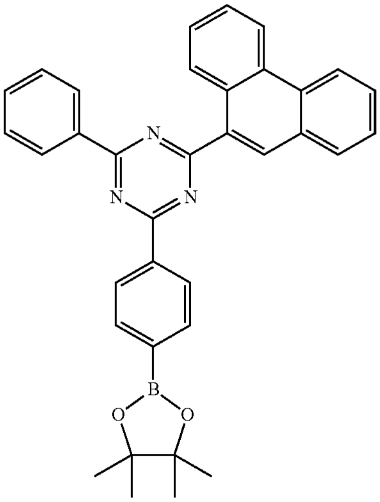 1835206-26-2 | 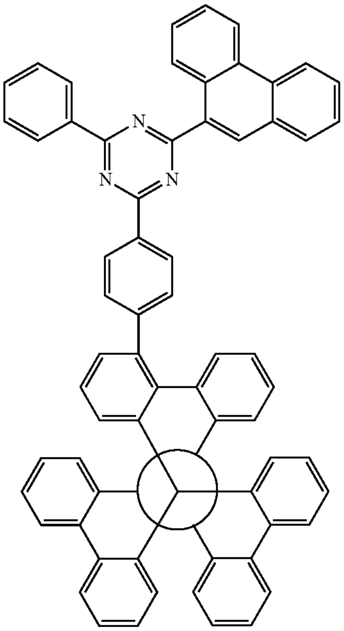 [SMILES: Cc1ccccc1-c1ccccc1C(c1ccccc1-c1ccccc1C)c1cccc(-c2ccc(-c3nc(-c4ccccc4)nc(-c4cc5ccccc5c5ccccc45)n3)cc2)c1-c1ccccc1C] | 63% |

-continued
| Ex | Reactants | Product | Yield |
| --- | --- | --- | --- |
| E11 | S103 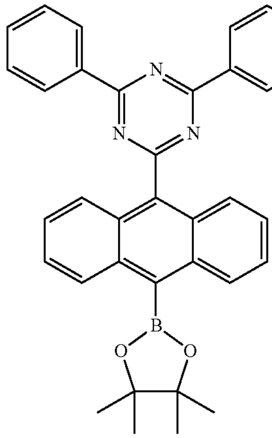 1510788-86-9 | 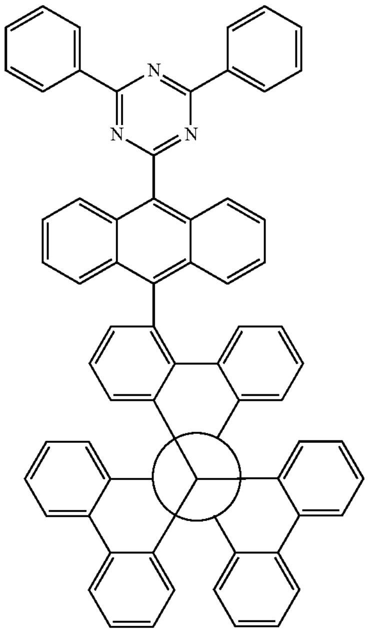 [SMILES: Cc1ccccc1-c1ccccc1C(c1ccccc1-c1ccccc1C)c1cccc(-c2c3ccccc3c(-c3nc(-c4ccccc4)nc(-c4ccccc4)n3)c3ccccc23)c1-c1ccccc1C] | 60% |
| E12 | S103 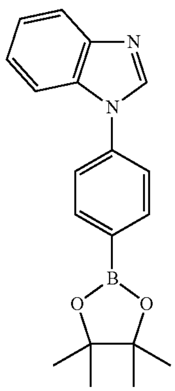 1104736-29-9 | 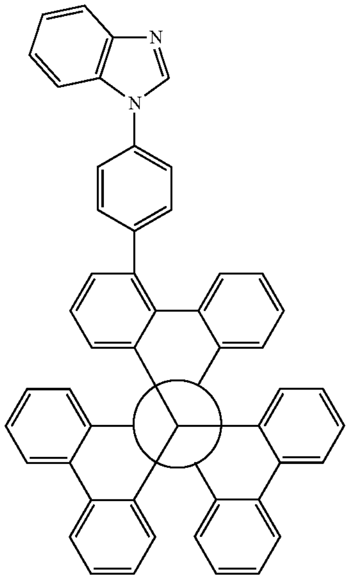 [SMILES: Cc1ccccc1-c1ccccc1C(c1ccccc1-c1ccccc1C)c1cccc(-c2ccc(-n3cnc4ccccc43)cc2)c1-c1ccccc1C] | 63% |

-continued
| Ex | Reactants | Product | Yield |
|---|---|---|---|
| E13 | S103<br>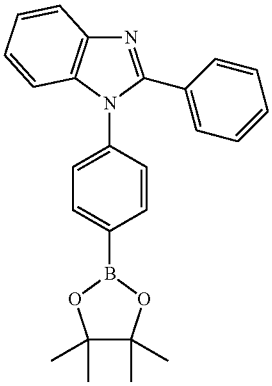<br>1169709-19-6 | 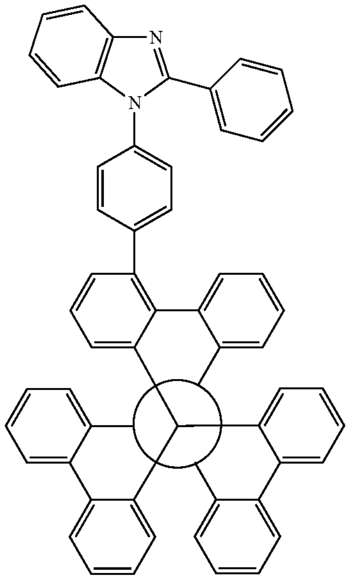 [SMILES: Cc1ccccc1-c1ccccc1C(c1ccccc1-c1ccccc1C)c1cccc(-c2ccc(-n3c(-c4ccccc4)nc4ccccc43)cc2)c1-c1ccccc1C] | 61% |
| E14 | S103<br>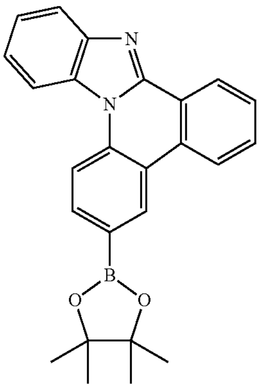<br>1228267-03-5 | 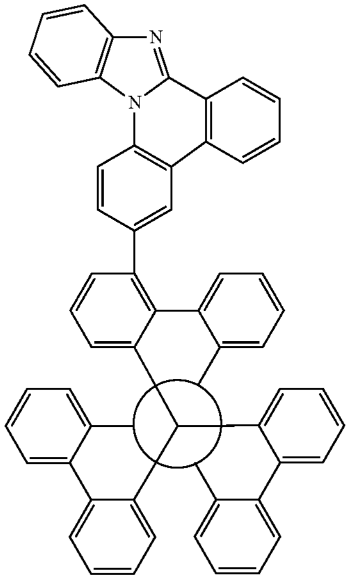 [SMILES: Cc1ccccc1-c1ccccc1C(c1ccccc1-c1ccccc1C)c1cccc(-c2ccc3c(c2)c2ccccc2c2nc4ccccc4n32)c1-c1ccccc1C] | 67% |

-continued
| Ex | Reactants | Product | Yield |
|---|---|---|---|
| E15 | S103<br>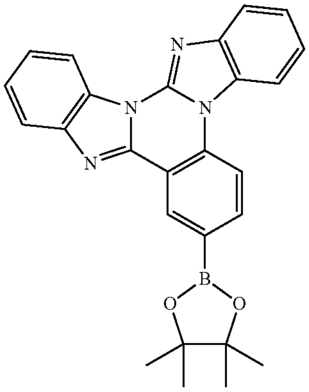<br>1246297-58-4 | 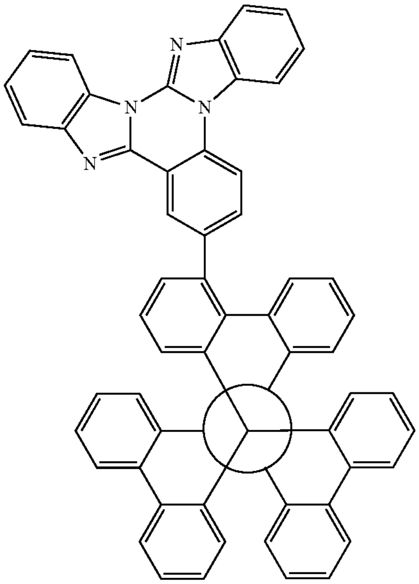 [SMILES: Cc1ccccc1-c1ccccc1C(c1ccccc1-c1ccccc1C)c1cccc(-c2ccc3c(c2)c2nc4ccccc4n2c2nc4ccccc4n32)c1-c1ccccc1C] | 65% |
| E16 | S108<br>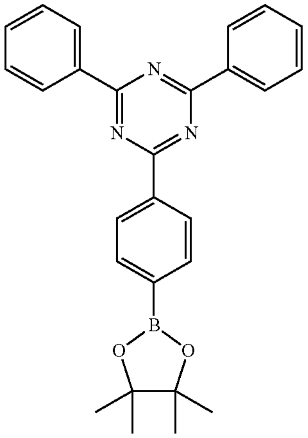<br>1219956-23-6 | 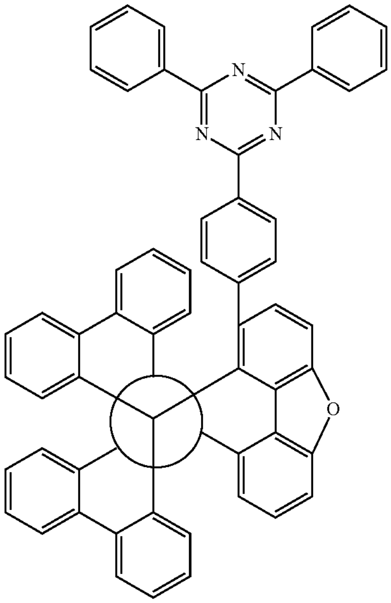 [SMILES: Cc1ccccc1-c1ccccc1C(c1ccccc1-c1ccccc1C)c1c(-c2ccc(-c3nc(-c4ccccc4)nc(-c4ccccc4)n3)cc2)ccc2oc3cccc(C)c3c12] | 38% |

-continued

| Ex | Reactants | Product | Yield |
|---|---|---|---|
| E17 | S109<br>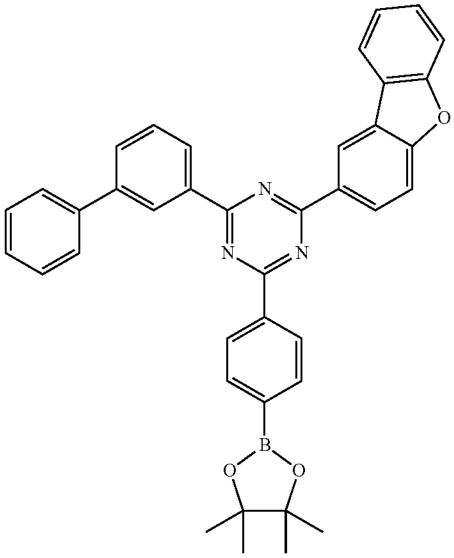<br>1835206-50-2 | 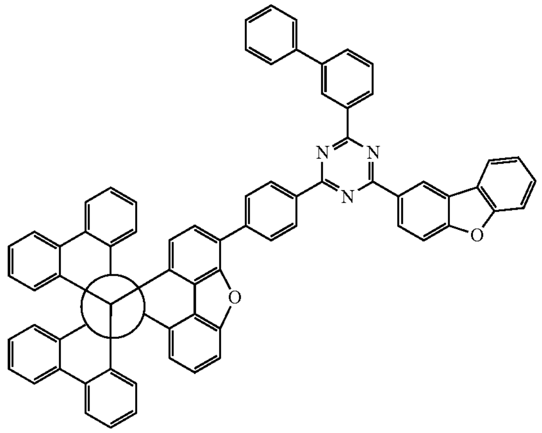 [SMILES: Cc1ccccc1-c1ccccc1C(c1ccccc1-c1ccccc1C)c1ccc(-c2ccc(-c3nc(-c4cccc(-c5ccccc5)c4)nc(-c4ccc5oc6ccccc6c5c4)n3)cc2)c2oc3cccc(C)c3c12] | 69% |

B) Device Examples

1) General Description of the Production and Analysis of the OLEDs

In the examples which follow, the production and device data of various OLEDs are presented.

The OLEDs can be produced as follows: Cleaned glass plaques (cleaning in Miele laboratory glass washer, Merck Extran detergent) coated with structured ITO (indium tin oxide) of thickness 50 nm are pretreated with UV ozone for 25 minutes (PR-100 UV ozone generator from UVP) and, within 30 min, for improved processing, coated with 25 nm of PEDOT:PSS (purchased as CLEVIOS™ P VP Al 4083 from Heraeus Precious Metals GmbH Deutschland, spun on from aqueous solution), and then baked at 180° C. for 10 min. These coated glass plaques form the substrates to which the OLEDs are applied.

The OLEDs have the following layer structure: substrate/hole transport layer 1 (HTL1) consisting of the compound HTM (see table 3) doped with 5% NDP-9 (commercially available from Novaled), 20 nm/hole transport layer 2 (HTL2)/optional electron blocker layer (EBL)/emission layer (EML)/hole blocker layer (HBL)/electron transport layer (ETL) and finally a cathode. The cathode is formed by an aluminum layer of thickness 100 nm. The exact composition of layers HTL1, EBL (if present), EML, HBL and ETL is shown in the tables which follow.

For production of the OLEDs, the materials used correspondingly in one layer are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as M1:M2:Ir1 (55%:35%:10%) mean here that the material M1 is present in the layer in a proportion by volume of 55%, M2 in a proportion of 35% and Ir1 in a proportion of 10%. Analogously, the electron transport layer may also consist of a mixture of two materials. The exact structure of the OLEDs can be found in table 1. The materials used for production of the OLEDs are shown in table 3.

The OLEDs are characterized in a standard manner. For this purpose, the electroluminescence spectra, the external quantum efficiency (EQE, measured in percent) as a function of luminance, calculated from current-voltage-luminance characteristics (IUL characteristics) assuming Lambertian radiation characteristics, and the lifetime are determined. The electroluminescence spectra are determined at a luminance of 1000 cd/$m^2$, and the CIE 1931 x and y color coordinates are calculated therefrom. The parameter U1000 in table 2 refers to the voltage which is required for a luminance of 1000 cd/$m^2$. EQE1000 refers to the external quantum efficiency at an operating luminance of 1000 cd/$m^2$.

The lifetime LD80 is defined as the time after which the luminance drops to 80% of the starting luminance in the course of operation with a constant current of 40 mA/$cm^2$.

2) Use of the Compounds of the Invention in a Hole Transport Layer

The examples which follow show that the compounds of the invention can be used as hole transport materials in a hole transport layer.

In examples D1 to D11 and D14, the inventive compounds H3, H5, H6, H9, H10, H13, H26 and H104 are used as hole transport materials in green-emitting triplet OLEDs (emitter Ir1 or Ir2 in each case).

In examples D18 to D24, the inventive compounds H9, H37, H47, H49 and H131 are used as hole transport materials in yellow-emitting triplet OLEDs (emitter Ir3 or Ir4 in each case).

| Ex. | HTL2 thickness | EML thickness | HBL thickness | ETL thickness |
|---|---|---|---|---|
| D1 | H9<br>40 nm | M1:Ir1<br>(85%:15%)<br>30 nm | ETM1<br>10 nm | ETM1:ETM2<br>(50%:50%)<br>30 nm |
| D2 | " | M1:Ir2<br>(85%:15%)<br>30 nm | " | " |
| D3 | " | M1:M2:Ir1<br>(45%:45%:10%)<br>30 nm | " | " |
| D4 | " | M1:M2:Ir2<br>(45%:45%:10%)<br>30 nm | " | " |
| D5 | H3<br>40 nm | M1:M2:Ir1<br>(45%:45%:10%)<br>30 nm | " | " |
| D6 | H5<br>40 nm | " | " | " |
| D7 | H6<br>40 nm | " | " | " |
| D8 | H10<br>40 nm | M1:M2:Ir1<br>(35%:55%:10%)<br>30 nm | " | " |
| D9 | H13<br>40 nm | M1:M2:Ir1<br>(45%:40%:15%)<br>30 nm | " | " |
| D10 | H20<br>40 nm | M1:M2:Ir2<br>(40%:45%:15%)<br>30 nm | " | " |
| D11 | H26<br>40 nm | " | " | " |
| D14 | H104<br>40 nm | " | " | " |
| D18 | H9<br>40 nm | M1:Ir3<br>(80%:20%)<br>30 nm | " | " |
| D19 | " | M1:Ir4<br>(85%:15%)<br>30 nm | " | " |
| D20 | H131<br>40 nm | M1:Ir3<br>(80%:20%)<br>30 nm | " | " |
| D22 | H37<br>40 nm | M1:Ir4<br>(85%:15%)<br>30 nm | " | " |
| D23 | H47<br>40 nm | M1:Ir4<br>(85%:15%)<br>30 nm | " | " |
| D24 | H49<br>40 nm | M1:Ir4<br>(85%:15%)<br>30 nm | " | " |

Excellent performance data are measured for the OLEDs in question, which are shown below:

| Ex. | EQE1000 (%) | U1000 (V) | CIE x/y | LT80 (h) |
|---|---|---|---|---|
| D1 | 20.3 | 3.1 | 0.33/0.64 | 120 |
| D2 | 19.2 | 3.1 | 0.36/0.62 | 150 |
| D3 | 20.5 | 3.0 | 0.33/0.64 | 140 |
| D4 | 19.5 | 3.0 | 0.36/0.62 | 180 |
| D5 | 20.7 | 3.0 | 0.33/0.64 | 240 |
| D6 | 20.4 | 2.9 | 0.33/0.64 | 230 |
| D7 | 20.9 | 3.0 | 0.33/0.64 | 210 |
| D8 | 20.5 | 3.0 | 0.33/0.64 | 240 |
| D9 | 20.1 | 3.1 | 0.33/0.63 | 260 |

-continued

| Ex. | EQE1000 (%) | U1000 (V) | CIE x/y | LT80 (h) |
|---|---|---|---|---|
| D10 | 19.3 | 3.0 | 0.36/0.62 | 430 |
| D11 | 19.7 | 3.0 | 0.36/0.62 | 470 |
| D14 | 19.7 | 3.1 | 0.37/0.62 | 460 |
| D18 | 17.0 | 2.9 | 0.39/0.59 | 300 |
| D19 | 19.1 | 3.0 | 0.46/0.53 | 360 |
| D20 | 17.6 | 3.0 | 0.40/0.58 | 520 |
| D22 | 19.0 | 2.8 | 0.46/0.52 | 380 |
| D23 | 19.5 | 2.9 | 0.46/0.53 | 370 |
| D24 | 19.7 | 2.9 | 0.46/0.53 | 410 |

3) Use of the Compounds of the Invention in a Hole Transport Layer and as Matrix Material in an Emitting Layer The examples which follow show that the compounds of the invention can be used as hole transport materials in a hole transport layer and additionally, in the same OLED, also as matrix materials in an emitting layer.

In each of examples D12 and D13, the inventive compound H26 is used. In addition, the inventive compound H32 or H34 is present in the emitting layer as co-host (h-type TMM) together with the further matrix material M1. The triplet emitter used in each case is the green emitter Ir-2.

| Ex. | HTL2 thickness | EML thickness | HBL thickness | ETL thickness |
|---|---|---|---|---|
| D12 | H26<br>40 nm | M1:H32:Ir2<br>(40%:45%:15%)<br>30 nm | ETM1<br>10 nm | ETM1:ETM2<br>(50%:50%)<br>30 nm |
| D13 | " | M1:H34:Ir2<br>(40%:45%:15%)<br>30 nm | " | " |

Excellent performance data are measured for the OLEDs in question, which are shown below:

| Ex. | EQE1000 (%) | U1000 (V) | CIE x/y | LT80 (h) |
|---|---|---|---|---|
| D12 | 19.8 | 2.9 | 0.37/0.62 | 450 |
| D13 | 19.4 | 3.1 | 0.36/0.62 | 480 |

4) Use of the Compounds of the Invention in the Hole Blocker Layer and the Electron Transport Layer, and in Some Cases Additionally Also in the Emitting Layer, the Electron Blocker Layer and the Hole Transport Layer Example D15 shows that the compounds of the invention can be used as materials in the hole blocker layer and additionally, in the same OLED, also as materials in the electron transport layer.

In example D15, the inventive compound E3 is used as hole blocker material in each case. In addition, the same compound E3 is present in the electron transport layer in a mixture with the further electron transport material ETM2. The triplet emitter used is the green emitter Ir-2.

| Ex. | HTL2 thickness | EBL thickness | EML thickness | HBL thickness | ETL thickness |
|---|---|---|---|---|---|
| D15 | HTM 40 nm | — | M1:M2:Ir2 (45%:45%:10%) 30 nm | E3 10 nm | E3:ETM2 (50%:50%) 30 nm |

Excellent performance data are measured for the OLED in question, which are shown below:

| Ex. | EQE1000 (%) | U1000 (V) | CIE x/y | LT80 (h) |
|---|---|---|---|---|
| D15 | 19.9 | 2.9 | 0.37/0.62 | 390 |

In examples D16, D17 and D21, inventive compounds are additionally used in the hole transport layer (D16, D17). In example D21, inventive compounds are actually present in all layers of the OLED from HTL to ETL:

| EX. | HTL2 thickness | EBL thickness | EML thickness | HBL thickness | ETL thickness |
|---|---|---|---|---|---|
| D16 | H26 40 nm | — | M1:M2:Ir2 (45%:45%:10%) 30 nm | E3 10 nm | E3:ETM2 (50%:50%) 30 nm |
| D17 | H26 40 nm | — | M1:M2:Ir2 (45%:45%:10%) 30 nm | E8 10 nm | E8:ETM2 (50%:50%) 30 nm |
| D21 | H26 30 nm | H131 10 nm | M1:H34:Ir3 (40%:50%:10%) 30 nm | E8 10 nm | E8:ETM2 (50%:50%) 30 nm |

Excellent performance data are measured for the OLED in question, which are shown below:

| Ex. | EQE1000 (%) | U1000 (V) | CIE x/y | LT80 (h) |
|---|---|---|---|---|
| D16 | 19.5 | 3.0 | 0.37/0.62 | 430 |
| D17 | 19.6 | 3.1 | 0.36/0.62 | 450 |
| D21 | 18.2 | 3.0 | 0.40/0.58 | 550 |

6) Comparison of the Inventive Compounds H9 with the Compound HTM-Ref

The performance of OLEDs comprising the material H9 is compared with reference OLEDs comprising the material HTM-Ref in various device constructions.

Six different device constructions a) to f) are used:

a) D-Ref1 vs. D1
b) D-Ref2 vs. D2
c) D-Ref3 vs. D3
e) D-Ref4 vs. D4
e) D-Ref5 vs. D18
f) D-Ref6 vs. D19

The exact device constructions comprising constructions with different triplet emitters and different matrix materials are as follows:

| Ex. | HTL2 thickness | EML thickness | HBL thickness | ETL thickness |
|---|---|---|---|---|
| D-Ref1 | HTM-Ref 40 nm | M1:Ir1 (85%:15%) 30 nm | ETM1 10 nm | ETM1:ETM2 (50%:50%) 30 nm |
| D1 | H9 40 nm | " | " | " |
| D-Ref2 | HTM-Ref 40 nm | M1:Ir2 (85%:15%) 30 nm | " | " |
| D2 | H9 40 nm | " | " | " |
| D-Ref3 | HTM-Ref 40 nm | M1:M2:Ir1 (45%:45%:10%) 30 nm | " | " |
| D3 | H9 40 nm | " | " | " |
| D-Ref4 | HTM-Ref 40 nm | M1:M2:Ir1 (45%:45%:10%) 30 nm | " | " |
| D4 | H9 40 nm | " | " | " |
| D-Ref5 | HTM-Ref 40 nm | M1:Ir3 (80%:20%) 30 nm | " | " |
| D18 | H9 40 nm | " | " | " |
| D-Ref6 | HTM-Ref 40 nm | M1:Ir4 (85%:15%) 30 nm | " | " |
| D19 | H9 40 nm | " | " | " |

The measurement data obtained for efficiency and lifetime inter alia are shown in the following table:

| Ex. | EQE1000 (%) | U1000 (V) | CIE x/y | LT80 (h) |
|---|---|---|---|---|
| D-Ref1 | 19.2 | 3.0 | 0.33/0.63 | 70 |
| D1 | 20.3 | 3.1 | 0.33/0.64 | 120 |
| D-Ref2 | 18.7 | 3.1 | 0.36/0.62 | 95 |
| D2 | 19.2 | 3.1 | 0.36/0.62 | 150 |
| D-Ref3 | 19.4 | 3,0 | 0.33/0.63 | 90 |
| D3 | 20.5 | 3.0 | 0.33/0.64 | 140 |
| D-Ref4 | 19.0 | 2.9 | 0.36/0.62 | 130 |
| D4 | 19.5 | 3.0 | 0.36/0.62 | 180 |
| D-Ref5 | 16.7 | 2.9 | 0.40/0.58 | 130 |
| D18 | 17.0 | 2.9 | 0.39/0.59 | 300 |
| D-Ref6 | 18.8 | 3.0 | 0.46/0.53 | 160 |
| D19 | 19.1 | 3.0 | 0.46/0.53 | 360 |

As apparent from the measurement data, in all direct comparisons between H9 and HTM-Ref, lifetime and efficiency are greatly improved, with comparable CIE coordinates and voltage.

TABLE 3
| Structural formulae of the materials used and CAS numbers |
| --- |
| HTM<br>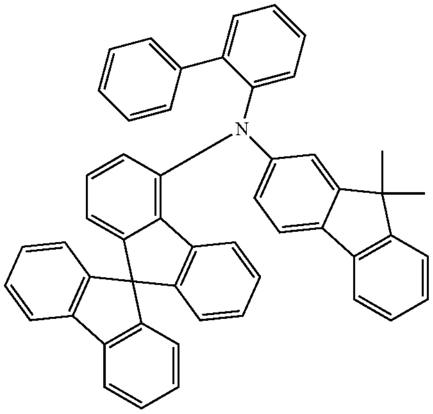<br>1450933-44-4 |
| M1<br>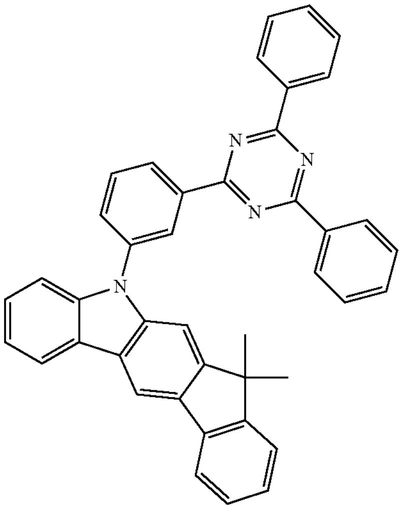<br>1257248-13-7 |
| M2<br>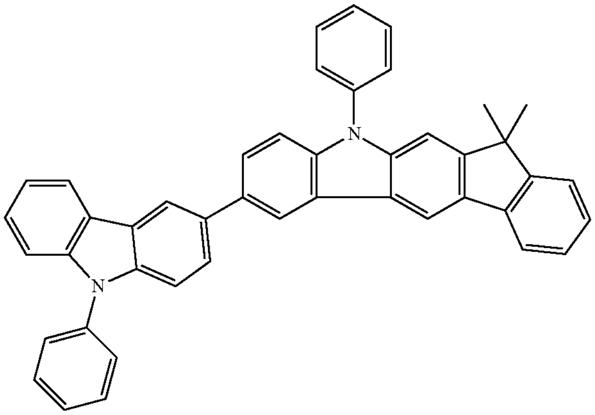<br>1357150-54-9 |

TABLE 3-continued
| Structural formulae of the materials used and CAS numbers |
| --- |
| ETM1 |
| 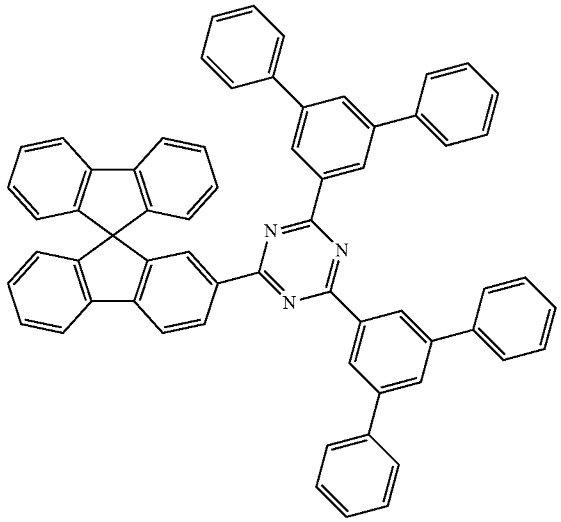 |
| 1233200-52-6 |
| ETM2 |
| 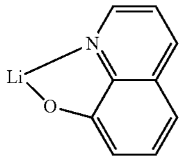 |
| 25387-93-3 |
| Ir1 |
| 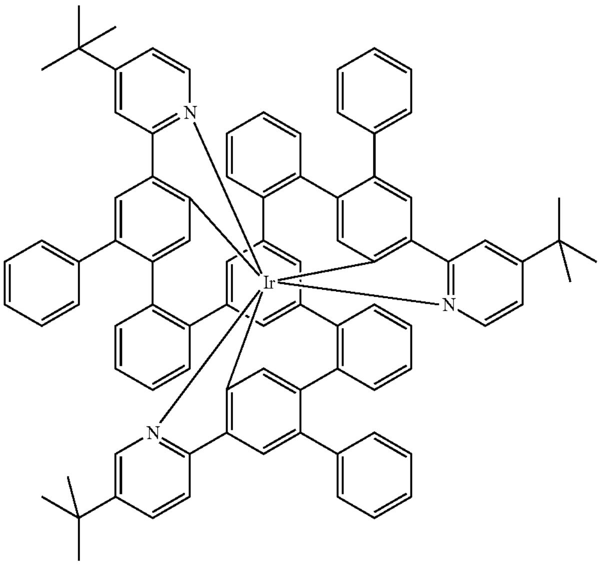 |
| 1989601-95-7 |

TABLE 3-continued
| Structural formulae of the materials used and CAS numbers |
|---|
| Ir2<br>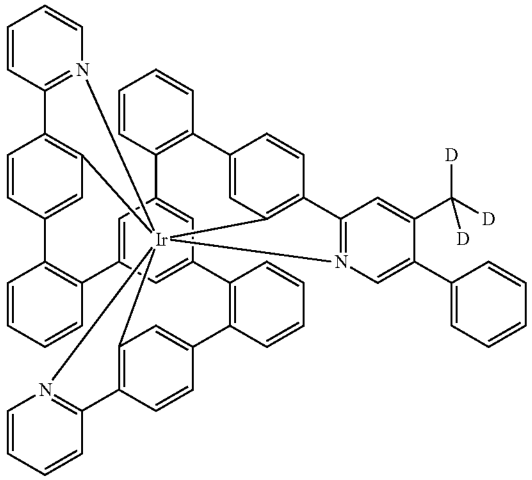<br>1989602-79-0 |
| Ir3<br>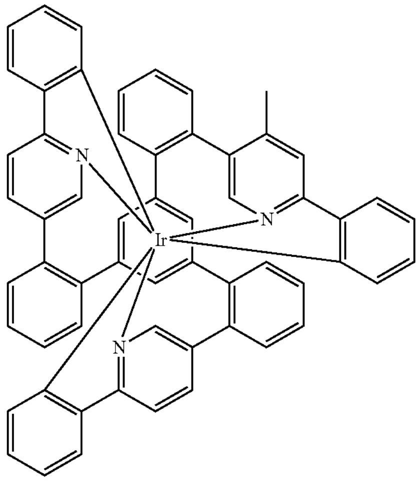<br>1989605-56-2 |
| Ir4<br>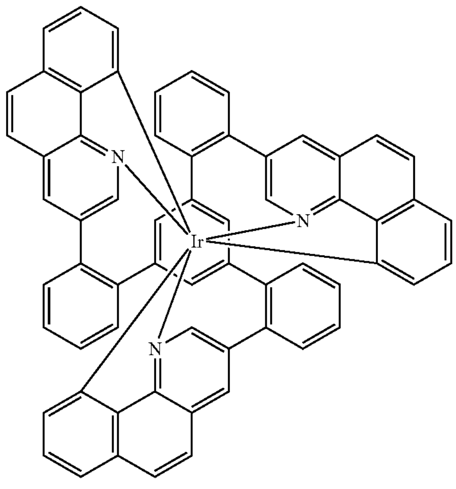<br>1989605-29-9 |

TABLE 3-continued

| Structural formulae of the materials used and CAS numbers |
|---|
| 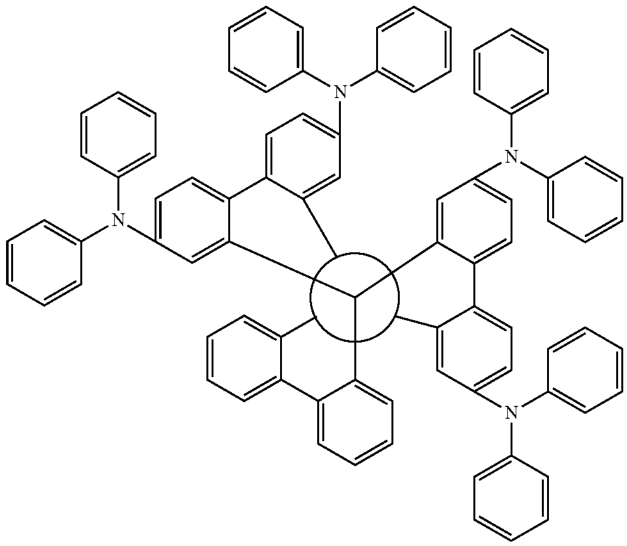 HTM-Ref<br>267884-23-1 |

The invention claimed is:

1. A compound of Formula (I),

Formula (I)

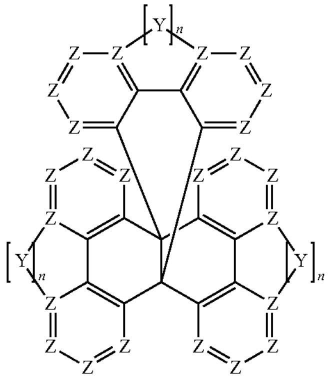

where the variables that occur are as follows:

Z is $CR^1$;

Y is not present;

n is 0;

$R^1$ is the same or different at each instance and are selected from H, D, F, CN, $Si(R^3)_3$, straight-chain alkyl groups having 1 to 20 carbon atoms, branched or cyclic alkyl groups having 3 to 20 carbon atoms, and aromatic ring systems having 6 to 40 aromatic ring atoms; where the alkyl groups and the aromatic ring system mentioned may each be substituted by one or more $R^3$ radicals; and with the proviso that two or more $R^1$ radicals may not be joined to one another and may not form a ring;

$R^3$ is the same or different at each instance and is selected from H, D, F, CN, $Si(R^4)_3$, straight-chain alkyl groups having 1 to 20 carbon atoms, branched or cyclic alkyl groups having 3 to 20 carbon atoms, and aromatic ring systems having 6 to 40 aromatic ring atoms; where two or more $R^3$ radicals may be joined to one another and may form a ring; where the alkyl groups mentioned and the aromatic ring systems mentioned may each be substituted by one or more $R^4$ radicals;

$R^4$ is the same or different at each instance and is selected from H, D, F, CN, alkyl groups having 1 to 20 carbon atoms, and aromatic ring systems having 6 to 40 aromatic ring atoms; where two or more $R^4$ radicals may be joined to one another and may form a ring; and where the alkyl groups and the aromatic ring systems mentioned may be substituted by F or CN;

characterized in that only one $R^1$ group per formula (I) is replaced by a group of Formula (A) or a group of Formula (H)

Formula (A)

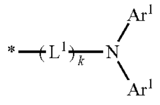

Formula (H)

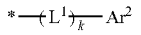

where:

$L^1$ is the same or different at each instance and is an aromatic ring system having 6 to 24 aromatic ring atoms or a heteroaromatic ring system having 5 to 24 aromatic ring atoms, each of which may be substituted by one or more $R^5$ radicals;

k is 0, 1, 2 or 3;

$Ar^1$ is the same or different at each instance and is an aromatic ring system having 6 to 24 aromatic ring atoms or a heteroaromatic ring system having 5 to 24 aromatic ring atoms, which may be substituted by one or more $R^5$ radicals;

$Ar^2$ is a triazinyl group which may be substituted by one or more $R^5$ radicals;

$R^5$ is the same or different at each instance and is selected from H, D, F, CN, $Si(R^6)_3$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring system mentioned may each be substituted by one or more $R^6$ radicals;

$R^6$ is the same or different at each instance and is selected from H, D, F, CN, alkyl groups having 1 to 20 carbon atoms, aromatic ring systems having 6 to 40 aromatic ring atoms and heteroaromatic ring systems having 5 to 40 aromatic ring atoms; where the alkyl groups, aromatic ring systems and heteroaromatic ring systems may be substituted by F or CN;

where the group of the Formula (A) or the group of the Formula (H) is bonded via the bond marked *.

2. A compound as claimed in claim 1, characterized in that Formula (I) is represented by one of Formulae (I-H-1) to (I-H-4) and (I-A-1) to (I-A-4)

Formula (I-H-1)

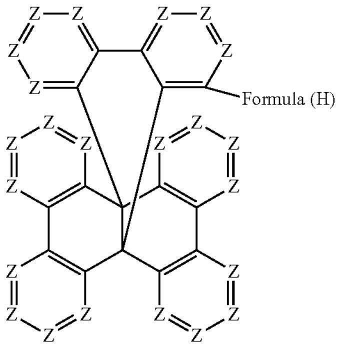

Formula (I-H-2)

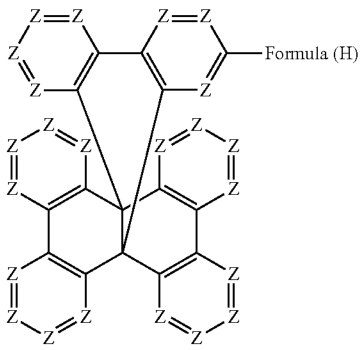

-continued

Formula (I-H-3)

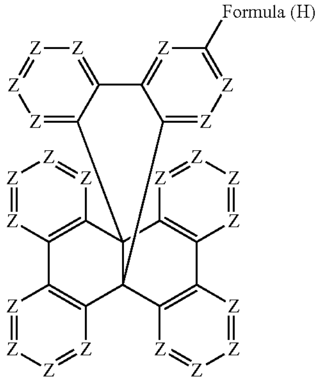

Formula (I-H-4)

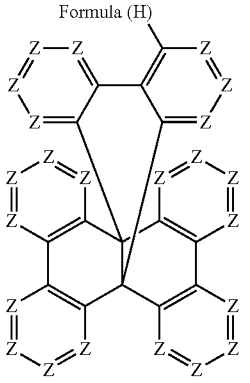

Formula (I-A-1)

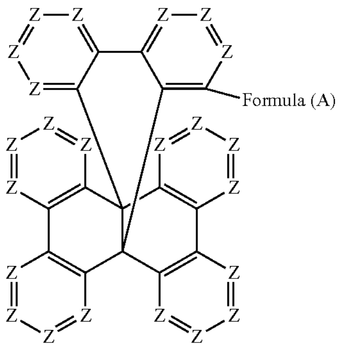

Formula (I-A-2)

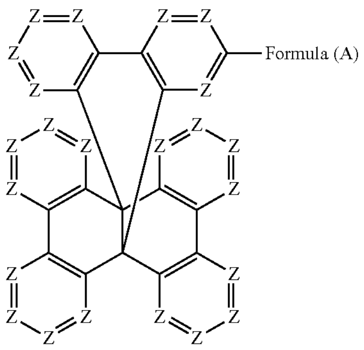

-continued

Formula (I-A-3)

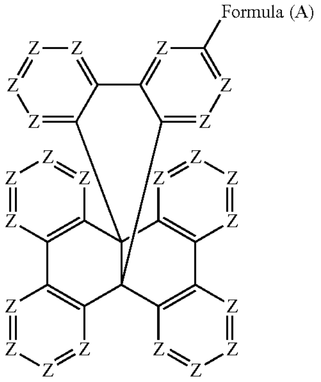

Formula (I-A-4)

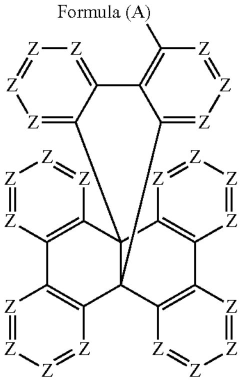

where the groups that occur are as defined in claim 1, and where "Formula (A)" is a group of the Formula (A) as defined in claim 1, and where "Formula (H)" is a group of the Formula (H) as defined in claim 1.

3. The compound as claimed in claim 1, wherein $R^1$ is the same or different at each instance and is selected from H, D, straight-chain or branched alkyl groups having up to 12 carbon atoms, and aromatic ring systems having 6 to 24 aromatic ring atoms; where the alkyl groups mentioned and the aromatic ring systems mentioned may each be substituted by one or more $R^3$ radicals.

4. The compound as claimed in claim 1, wherein $R^3$ is the same or different at each instance and is selected from H, D, F, CN, straight-chain alkyl groups having 1 to 12 carbon atoms, branched or cyclic alkyl groups having 3 to 12 carbon atoms, and aromatic ring systems having 6 to 24 aromatic ring atoms; where the alkyl groups mentioned and the aromatic ring systems mentioned may each be substituted by one or more $R^4$ radicals.

5. The compound as claimed in claim 1, wherein $R^4$ is the same or different at each instance and is selected from H, D, F, CN, straight-chain alkyl groups having 1 to 12 carbon atoms, branched or cyclic alkyl groups having 3 to 12 carbon atoms, and aromatic ring systems having 6 to 24 aromatic ring atoms; where the alkyl groups mentioned and the aromatic ring systems mentioned may be substituted by F or CN.

6. The compound as claimed in claim 1, wherein only one $R^1$ group per Formula (I) is replaced by a group of Formula (A).

7. The compound as claimed in claim 1, wherein $L^1$ is a divalent group selected from phenylene, biphenylene, terphenylene, naphthylene, dibenzofuran, dibenzothiophene, carbazole and fluorene, where the divalent group may be substituted by one or more $R^5$ radicals.

8. The compound as claimed in claim 1, wherein $Ar^1$ is the same or different at each instance and is selected from phenyl, biphenyl, terphenyl, fluorenyl, naphthyl, spirobifluorenyl, pyridyl, pyrimidyl, triazinyl, dibenzofuranyl, benzofused dibenzofuranyl, dibenzothiophenyl, benzofused dibenzothiophenyl, carbazolyl, and benzofused carbazolyl, and combinations of two, three or four of these groups, where the groups mentioned may each be substituted by one or more $R^5$ radicals.

9. A process for preparing the compound as claimed in claim 1 which comprises first preparing the alkoxy-substituted base skeleton and then converting the alkoxy-substituted base skeleton in a further step to a reactive compound, preferably to a triflate derivative, which is converted in a further step by transition metal-catalyzed coupling reaction.

10. An oligomer, polymer or dendrimer containing one or more compounds as claimed in claim 1, wherein the bond(s) to the polymer, oligomer or dendrimer may be localized at any desired positions substituted by $R^1$ or $R^5$.

11. A formulation comprising one or more compounds as claimed claim 1 and at least one solvent.

12. An electronic device selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs), comprising at least one compound as claimed in claim 1.

13. The device as claimed in claim 12, wherein the device is an electroluminescent device comprising anode, cathode and at least one organic layer, wherein the compound is present in a hole-transporting layer, as matrix material in an emitting layer, or in an electron-transporting layer.

14. The compound as claimed in claim 1, wherein $R^1$ is selected, identically or differently, from H and D.

15. The compound as claimed in claim 1, wherein only one $R^1$ group in Formula (I) is replaced by a group of the Formula (H).

16. The compound as claimed in claim 1, characterized in that only one $R^1$ group in Formula (I) is replaced by a group of the Formula (A), and further characterized in that index k=0, and further characterized in that $R^1$ is selected, identically or differently, from H and D.

17. The compound as claimed in claim 1, characterized in that Formula (I) is represented by one of the Formulae (I-H-1), (I-H-3), (I-H-4), (I-A-1), (I-A-3) and (I-A-4)

Formula (I-H-1)

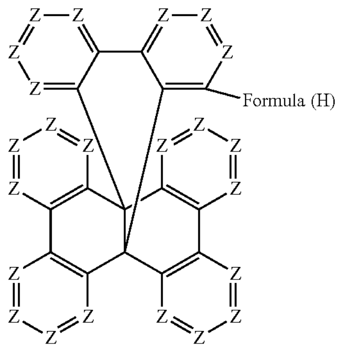

-continued

Formula (I-H-3)

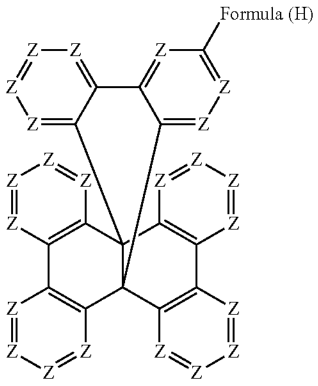

Formula (I-H-4)

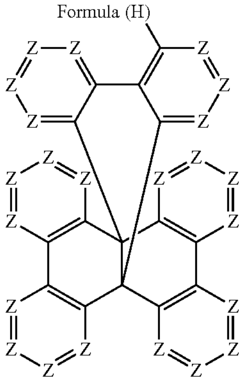

Formula (I-A-1)

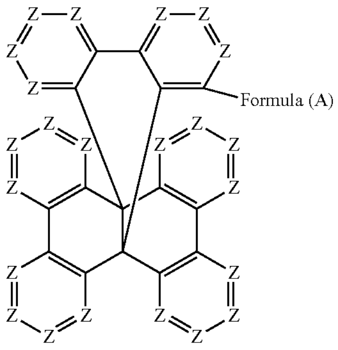

Formula (I-A-3)

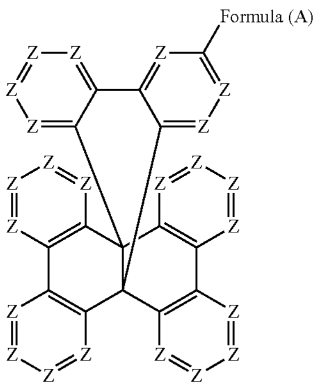

-continued

Formula (I-A-4)

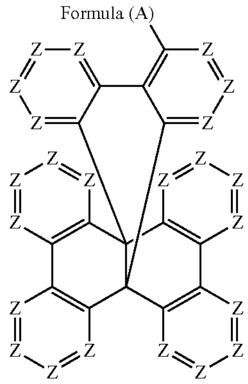

where the groups that occur are as defined in claim 1, and where "Formula (A)" is a group of the Formula (A) as defined in claim 1, and where "Formula (H)" is a group of the Formula (H) as defined in claim 1, and wherein $R^1$ is selected, identically or differently, from H and D.

18. The compound as claimed in claim 1, characterized in that Formula (I) is represented by one of Formulae (I-H-1), (I-H-3) and (I-H-4), Formula (I-H-I)

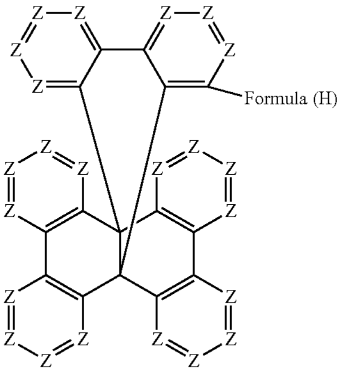

Formula (I-H-3)

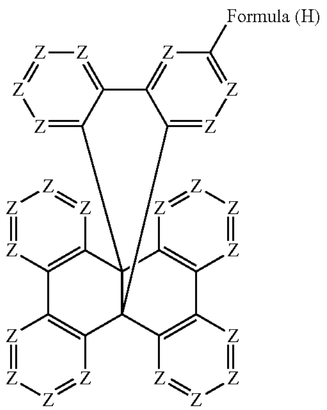

-continued
Formula (I-H-4)
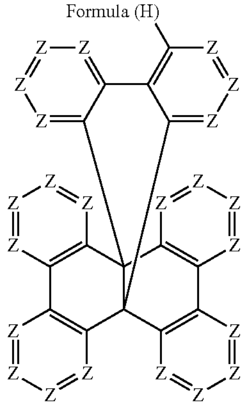
where index k is 0, and wherein $R^1$ is selected, identically or differently, from H and D.
* * * * *